United States Patent
Brown et al.

(10) Patent No.: US 7,340,794 B2
(45) Date of Patent: Mar. 11, 2008

(54) MULTI-MOTION TOOTHBRUSH

(75) Inventors: Patrick W. Brown, Mantua, OH (US); Douglas A. Gall, Strongsville, OH (US)

(73) Assignee: The Procter & Gamble Company, Cincinnati, OH (US)

( * ) Notice: Subject to any disclaimer, the term of this patent is extended or adjusted under 35 U.S.C. 154(b) by 0 days.

(21) Appl. No.: 11/414,908

(22) Filed: May 1, 2006

(65) Prior Publication Data
US 2006/0191085 A1     Aug. 31, 2006

Related U.S. Application Data

(63) Continuation of application No. 11/252,442, filed on Oct. 18, 2005, now abandoned, which is a continuation of application No. 10/128,018, filed on Apr. 22, 2002, now abandoned, which is a continuation-in-part of application No. 10/114,780, filed on Apr. 3, 2002, now abandoned, which is a continuation-in-part of application No. 10/027,594, filed on Dec. 21, 2001, now abandoned, which is a continuation-in-part of application No. 09/993,167, filed on Nov. 6, 2001, now Pat. No. 6,725,490, and application No. 10/036,613, Nov. 7, 2001, now abandoned.

(51) Int. Cl.
*A61C 17/22* (2006.01)
(52) U.S. Cl. .................. 15/22.1; 15/22.2; 15/22.4; 15/28
(58) Field of Classification Search .......... 15/22.1, 15/22.2, 22.4, 28, 29, 201
See application file for complete search history.

(56) References Cited

U.S. PATENT DOCUMENTS

| | | | |
|---|---|---|---|
| 1,557,244 A | 10/1925 | Dominique | |
| 2,140,307 A * | 12/1938 | Belaschk et al. | 15/28 |
| 2,215,031 A | 9/1940 | Elmore | |
| 3,129,449 A | 4/1964 | Cyzer | |
| 3,159,859 A * | 12/1964 | Rasmussen | 15/22.1 |
| 3,233,265 A * | 2/1966 | Hartmann | 15/22.1 |
| 3,240,077 A | 3/1966 | Smith | |
| 3,242,516 A | 3/1966 | Cantor | |
| 3,592,188 A * | 7/1971 | Barnett | 601/142 |
| 4,274,173 A | 6/1981 | Cohen | |
| 4,374,354 A | 2/1983 | Petrovic | |
| 4,766,630 A | 8/1988 | Hegemann | |
| 4,845,795 A | 7/1989 | Crawford et al. | |
| 4,989,287 A | 2/1991 | Scherer | |
| 5,020,179 A | 6/1991 | Scherer | |

(Continued)

FOREIGN PATENT DOCUMENTS

CA     1082408     7/1980

(Continued)

*Primary Examiner*—Mark Spisich
(74) *Attorney, Agent, or Firm*—Vladimir Vitenberg; Kathleen Y. Carter; Richard L. Alexander

(57) ABSTRACT

An electric toothbrush is disclosed. The electric toothbrush includes a body having an interior hollow region for retaining one or more motors, batteries, and drive mechanisms. The toothbrush includes multiple bristle carriers. Each of the bristle carriers undergoes some type of movement and is driven by the one or more motors and drive mechanisms. Various combinations of movement of the bristle carriers are described. And, numerous drive train mechanisms are disclosed for achieving the noted motions.

6 Claims, 33 Drawing Sheets

U.S. PATENT DOCUMENTS

| | | | |
|---|---|---|---|
| 5,033,150 A * | 7/1991 | Gross et al. | 15/22.1 |
| 5,035,020 A | 7/1991 | Winiewski | |
| 5,068,939 A | 12/1991 | Holland | |
| 5,070,567 A | 12/1991 | Holland | |
| 5,088,145 A | 2/1992 | Whitefield | |
| 5,120,225 A | 6/1992 | Amit | |
| 5,142,723 A | 9/1992 | Lustig et al. | |
| 5,170,525 A | 12/1992 | Cafaro | |
| 5,177,826 A | 1/1993 | Vrignaud et al. | |
| 5,186,627 A | 2/1993 | Amit et al. | |
| 5,226,206 A | 7/1993 | Davidovitz et al. | |
| 5,253,382 A | 10/1993 | Beny | |
| 5,259,083 A | 11/1993 | Stansbury, Jr. | |
| 5,274,870 A | 1/1994 | Stollman | |
| 5,276,932 A | 1/1994 | Byrd | |
| 5,321,866 A * | 6/1994 | Klupt | 15/22.1 |
| 5,353,460 A | 10/1994 | Bauman | |
| 5,359,747 A | 11/1994 | Amakasu | |
| 5,383,242 A | 1/1995 | Bigler et al. | |
| 5,416,942 A | 5/1995 | Baldacci et al. | |
| 5,435,032 A | 7/1995 | McDougall | |
| 5,435,034 A | 7/1995 | Bigler et al. | |
| 5,465,444 A | 11/1995 | Bigler et al. | |
| 5,481,775 A * | 1/1996 | Gentile et al. | 15/22.1 |
| 5,500,970 A | 3/1996 | Maurer et al. | |
| 5,504,959 A | 4/1996 | Yukawa et al. | |
| 5,524,312 A | 6/1996 | Tan et al. | |
| 5,528,786 A * | 6/1996 | Porat et al. | 15/22.1 |
| 5,577,285 A | 11/1996 | Drossler | |
| 5,617,601 A | 4/1997 | McDougall | |
| 5,617,603 A | 4/1997 | Mei | |
| 5,625,916 A | 5/1997 | McDougall | |
| 5,679,991 A | 10/1997 | Wolf | |
| 5,732,432 A | 3/1998 | Hui | |
| 5,732,433 A | 3/1998 | Gocking et al. | |
| 5,784,743 A | 7/1998 | Shek | |
| 5,836,030 A | 11/1998 | Hazeu et al. | |
| 5,842,245 A | 12/1998 | Pai | |
| 5,850,655 A | 12/1998 | Gocking et al. | |
| 5,862,558 A | 1/1999 | Hilfinger et al. | |
| 5,867,856 A | 2/1999 | Herzog | |
| 5,876,206 A | 3/1999 | Maurer | |
| 5,901,397 A | 5/1999 | Hafele et al. | |
| 5,974,613 A | 11/1999 | Herzog | |
| 5,974,615 A | 11/1999 | Schwarz-Hartmann et al. | |
| 5,996,157 A | 12/1999 | Smith et al. | |
| 6,000,083 A | 12/1999 | Blaustein et al. | |
| 6,021,538 A | 2/2000 | Kressner et al. | |
| 6,032,313 A | 3/2000 | Tsang | |
| 6,138,310 A | 10/2000 | Porper et al. | |
| 6,178,579 B1 | 1/2001 | Blaustein et al. | |
| 6,189,693 B1 | 2/2001 | Blaustein et al. | |
| 6,195,828 B1 | 3/2001 | Fritsch | |
| 6,209,164 B1 | 4/2001 | Sato | |
| 6,230,717 B1 | 5/2001 | Marx et al. | |
| 6,237,178 B1 | 5/2001 | Krammer et al. | |
| 6,308,358 B2 * | 10/2001 | Gruber et al. | 15/22.1 |
| 6,308,359 B2 | 10/2001 | Fritsch et al. | |
| 6,311,837 B1 | 11/2001 | Blaustein et al. | |
| 6,347,425 B1 * | 2/2002 | Fattori et al. | 15/22.1 |
| 6,360,395 B2 | 3/2002 | Blaustein et al. | |
| 6,408,473 B1 | 6/2002 | Kessler | |
| 6,446,294 B1 | 9/2002 | Specht | |
| 2001/0020314 A1 | 9/2001 | Calabrese | |

FOREIGN PATENT DOCUMENTS

| | | | |
|---|---|---|---|
| CA | 1330383 | | 6/1994 |
| CN | 2236827 Y | | 10/1996 |
| CN | 2271352 Y | | 12/1997 |
| CN | 2271353 Y | | 12/1997 |
| CN | 2274947 Y | | 2/1998 |
| CN | 2324988 | | 6/1999 |
| DE | 2736286 | | 7/1978 |
| DE | 8426426 | | 3/1985 |
| DE | 3406112 | | 8/1985 |
| DE | 29618755 | | 3/1997 |
| DE | 29517610 | | 4/1997 |
| DE | 19701964 | * | 7/1998 |
| DE | 19701964 | | 8/1998 |
| DE | 29809977 | | 2/1999 |
| EP | 254397 | | 1/1988 |
| EP | 259648 | | 3/1988 |
| EP | 208401 | | 5/1991 |
| EP | 537465 | | 4/1993 |
| EP | 546203 | * | 6/1993 |
| EP | 546203 | | 8/1996 |
| EP | 0 758 857 B1 | | 2/1997 |
| EP | 1053721 | | 11/2000 |
| FR | 1250455 | | 10/1959 |
| FR | 2337524 | | 8/1977 |
| FR | 2616306 | * | 12/1988 |
| GB | 1488628 | | 12/1976 |
| GB | 1583558 | | 1/1981 |
| GB | 2228861 | | 9/1990 |
| GB | 2247297 | * | 2/1992 |
| GB | 2290224 | | 12/1995 |
| GB | 2319170 | | 5/1998 |
| JP | 57-89810 | | 6/1982 |
| JP | U4-133733 | | 7/1991 |
| JP | 5146314 | | 11/1991 |
| JP | 05-146313 A | | 6/1993 |
| JP | 5-146314 | * | 6/1993 |
| JP | 5-161509 | | 6/1993 |
| JP | 5146314 | | 6/1993 |
| JP | 5-199917 | | 8/1993 |
| JP | 5-269023 | | 10/1993 |
| JP | 6-189822 | | 7/1994 |
| JP | 7-116024 | | 5/1995 |
| JP | 8-322641 | | 10/1996 |
| JP | 8-322641 | * | 12/1996 |
| JP | 2804940 | | 7/1998 |
| JP | 10-211221 | * | 8/1998 |
| JP | 2811246 | | 8/1998 |
| JP | 10-211221 | | 11/1998 |
| KR | 1986-0001137 | | 6/1986 |
| KR | 143460 | | 1/1998 |
| KR | 183429 | | 3/2000 |
| TW | 135303 | | 10/1976 |
| TW | 154730 | | 3/1979 |
| TW | 248031 | | 12/1982 |
| TW | 137856 | | 7/1990 |
| TW | 212909 | | 9/1993 |
| TW | 239963 | | 2/1995 |
| TW | 239964 | | 2/1995 |
| TW | 311444 | | 12/1996 |
| TW | 330410 | | 12/1996 |
| TW | 406557 | | 5/1998 |
| WO | WO 94/03125 | | 2/1994 |
| WO | 94/28823 | * | 12/1994 |
| WO | WO 94/28823 | | 12/1994 |
| WO | 96/31171 | * | 10/1996 |
| WO | WO 96/31171 | | 10/1996 |
| WO | 99/12492 | * | 3/1999 |
| WO | WO 99/12492 | | 3/1999 |
| WO | WO 03/071979 A1 | | 9/2003 |

* cited by examiner

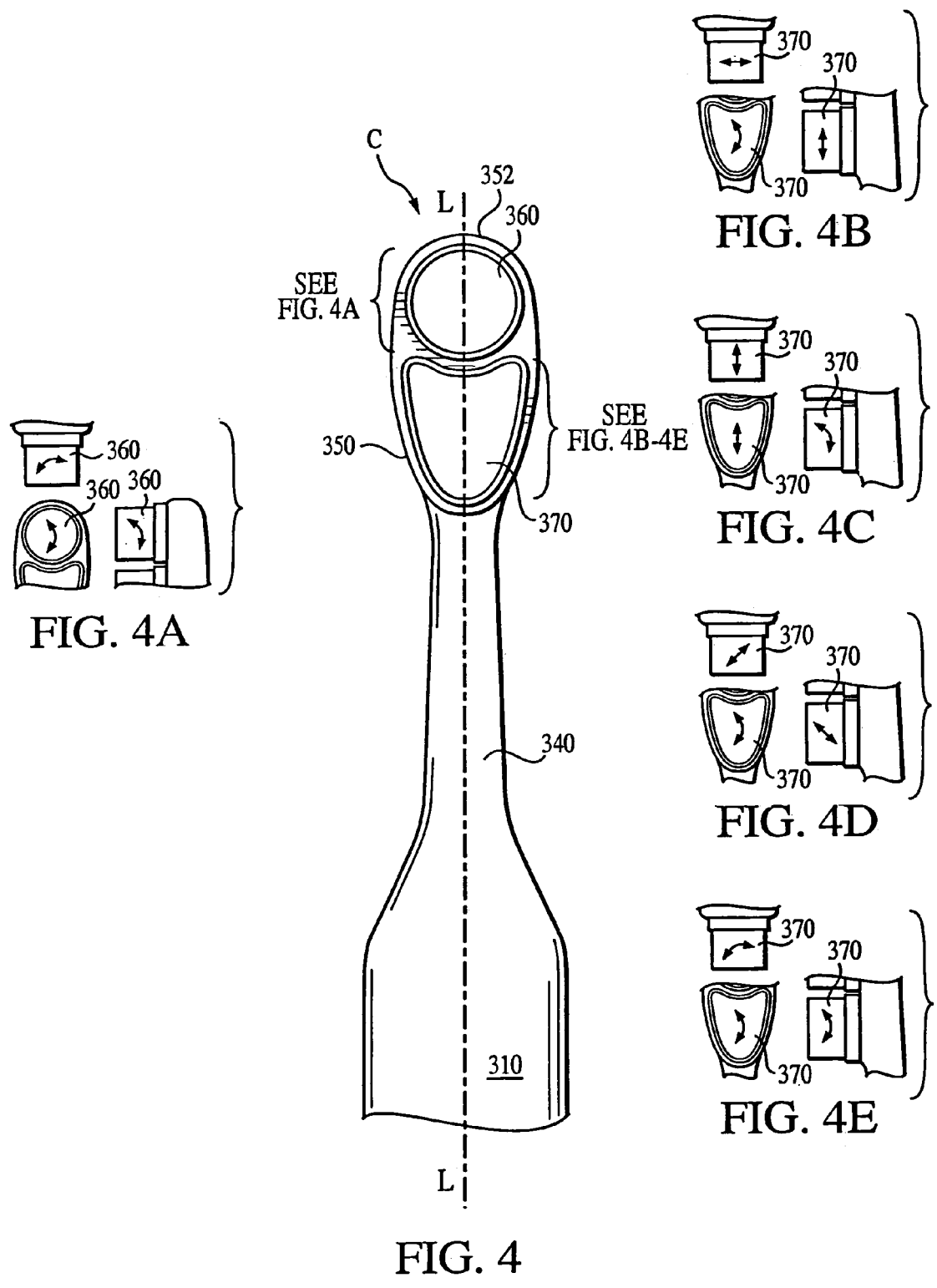

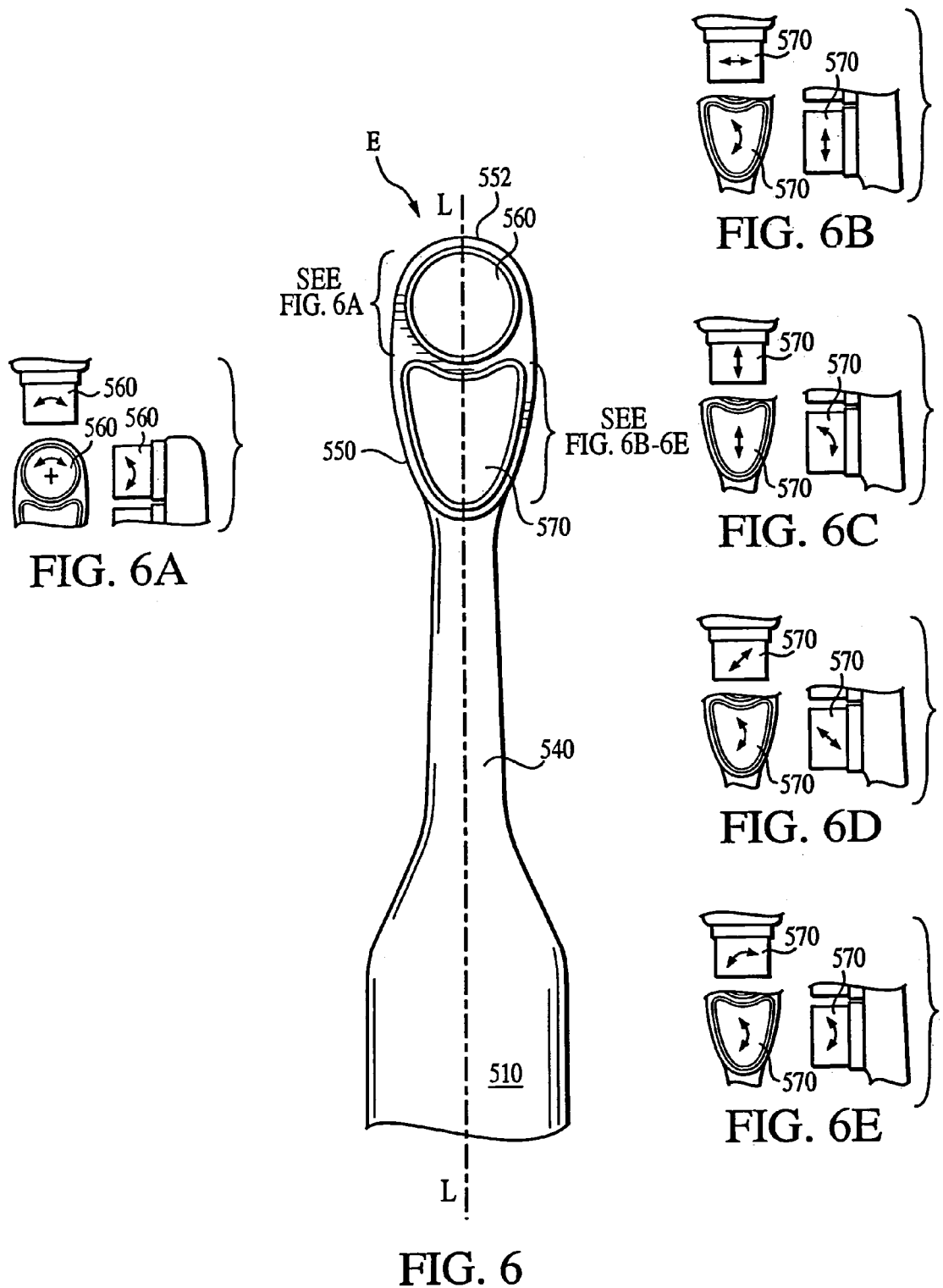

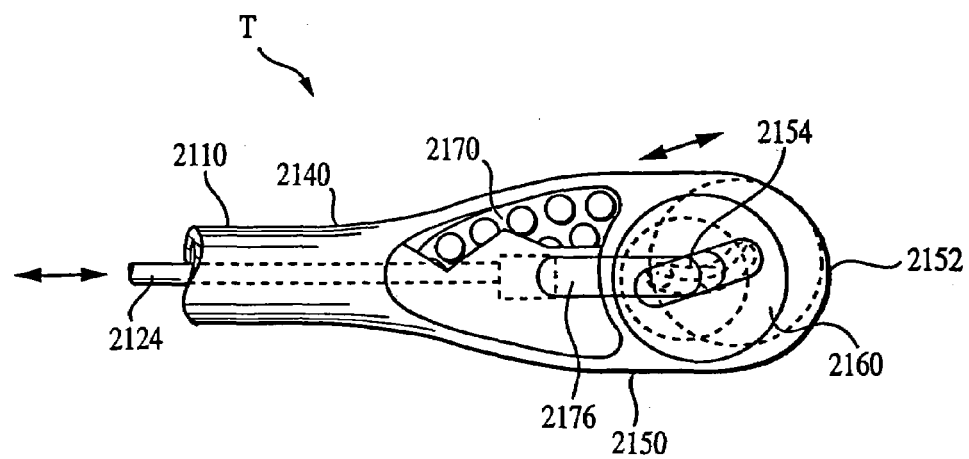
FIG. 15D
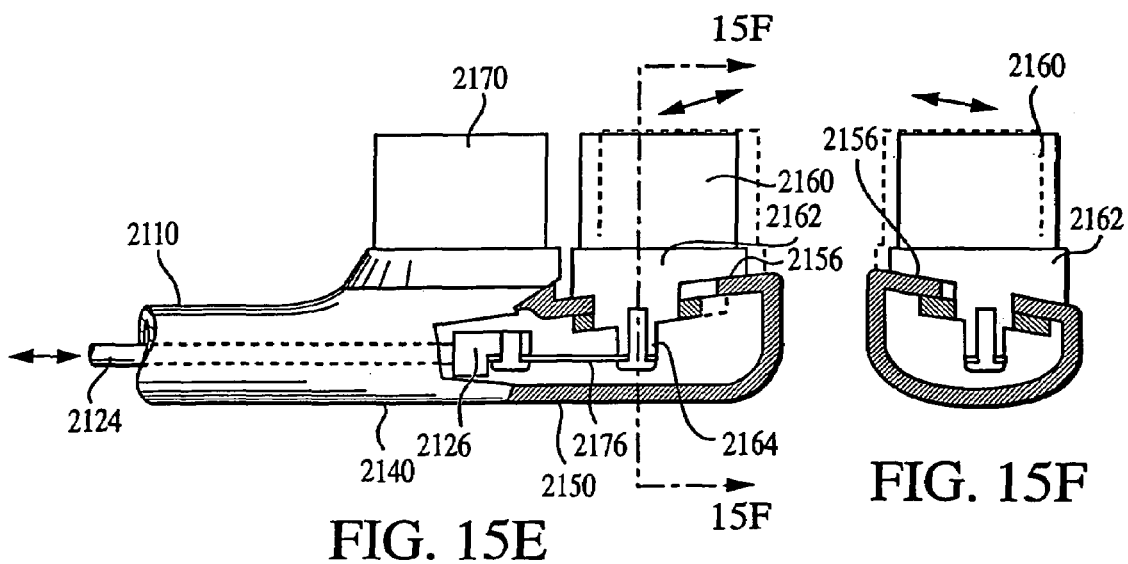
FIG. 15E
FIG. 15F

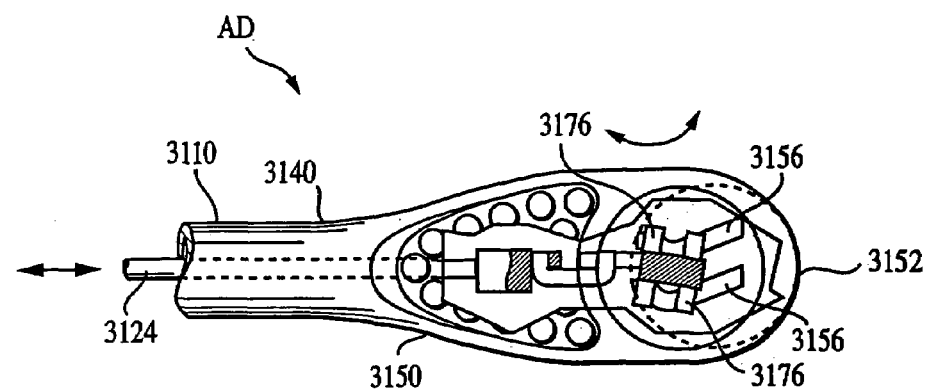
FIG. 21A
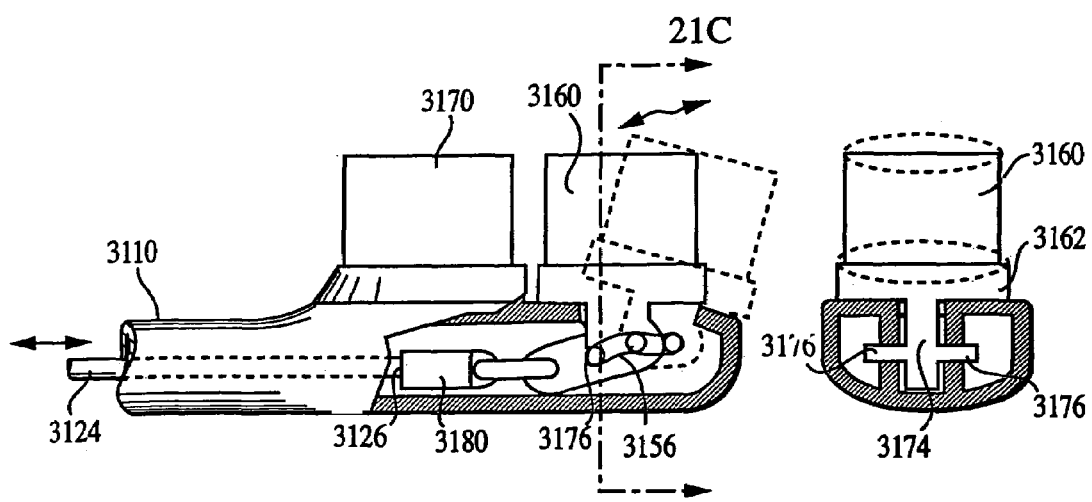 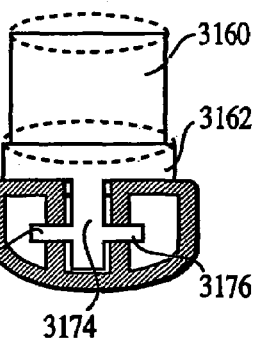
FIG. 21B          FIG. 21C though this

MULTI-MOTION TOOTHBRUSH

CROSS REFERENCES TO RELATED APPLICATIONS

This application is a continuation of U.S. application Ser. No. 11/252,442, filed Oct. 18, 2005, abandoned, which is a continuation of U.S. application Ser. No. 10/128,018, filed Apr. 22, 2002, abandoned, which is a continuation-in-part of U.S. application Ser. No. 10/114,780, U.S. Publication No. 2003-0084526, filed Apr. 3, 2002, abandoned, which is a continuation-in-part of U.S. application Ser. No. 10/027,594, filed Dec. 21, 2001, now abandoned, which is a continuation-in-part of U.S. application Ser. No. 09/993,167 filed Nov. 6, 2001, now U.S. Pat. No. 6,725,490, and U.S. application Ser. No. 10/036,613, U.S. Publication No. 2003-0084525, filed on Nov. 7, 2001, abandoned, the substances of which are incorporated herein by reference.

FIELD OF THE INVENTION

The present invention relates to the field of toothbrushes, and more particularly, the invention relates to the field of electrically powered toothbrushes.

BACKGROUND OF THE INVENTION

Most known electric toothbrushes utilize a single bristle carrier that is powered or otherwise driven by an electric motor incorporated in the toothbrush. The bristle carriers in these toothbrushes undergo a wide array of motions. For example, bristle carriers undergoing rotary motion are well known. Bristle carriers that reciprocate in a linear fashion within the plane of the brush are also known. And, bristle carriers that reciprocate in a linear fashion perpendicular to the plane of the brush are also known. Although satisfactory in certain respects, a need still exists for an improved powered toothbrush design.

Numerous attempts have been made to improve the design, efficiency, cleaning efficacy, simplicity, and/or commercial viability of electric toothbrushes. One approach has been the provision of multiple powered bristle carriers. Most artisans have grouped multiple sets of bristles along an end of a brush and incorporated a drive mechanism for simultaneously rotating each of the bristle sets, together. Exemplary designs include those disclosed in U.S. Pat. Nos. 3,242,516; 4,156,620; 4,845,795; 5,088,145; 5,020,179; 4,827,550; and 4,545,087, all of which are hereby incorporated by reference.

A related strategy is to group sets of bristles on multiple rotating bristle carriers, as disclosed in U.S. Pat. Nos. 2,140,307 and 5,170,525, both of which are herein incorporated by reference. Rather than rotating each individual bristle set about its center, i.e. the approach adopted in the previously noted patents, the designs described in the '307 and '525 rotate multiple groups of bristle sets about the center of a bristle carrier. Specifically, multiple groups of bristle sets are disposed on a circular bristle carrier and that bristle carrier, typically one of several, is rotated about its own axis.

U.S. Pat. No. 5,070,567, herein incorporated by reference, describes a design combining the two previously noted strategies. A rotating bristle carrier is provided along with multiple individually rotatable bristle sets. Although this design likely provides many of the advantages associated with each of its predecessors, the cleaning efficacy of spinning bristle sets, alone, is somewhat limited.

Yet another design is disclosed in U.S. Pat. No. 5,617,603, herein incorporated by reference. The '603 describes an assembly of "staggered swing" brushes. Apparently, the two bristle carriers move along a complex path within the plane of the toothbrush.

Although dual bristle carriers that undergo various combinations of movement have been disclosed in the prior art, there remains a need to provide an electric toothbrush with multiple bristle carriers that provides additional combinations of motion.

SUMMARY OF THE INVENTION

The present invention satisfies all of the previously noted objectives and provides, in one aspect, an electrically powered toothbrush comprising a body having an end, a head opposite from the end, and a neck extending between the end and the head. The body defines a hollow region within its interior. The toothbrush further includes an electrical motor and power source disposed in the hollow region of the body. The motor provides a rotating or oscillating drive shaft which has a distal end that is offset from a longitudinal axis of the drive shaft. The toothbrush includes a base pivotally secured to the head and positionable with respect to the head by a laterally extending pivot member. The base defines a receiving channel adapted to receive the distal end of the drive shaft. The toothbrush further includes a first bristle carrier and a second bristle carrier disposed on the head of the brush. The first bristle carrier is secured to the base. Upon rotation or oscillation of the drive shaft, the distal end of the drive shaft moves within the receiving channel of the base and causes the base and the first bristle carrier to pivot about the pivot member.

In another aspect, the present invention provides an electrically powered toothbrush comprising a body having a first end, a head opposite therefrom, and a neck extending between the end and the head. The body defines a hollow interior region. The toothbrush further includes an electrical motor and power source disposed in the hollow interior of the body. The motor provides a reciprocating drive shaft. The toothbrush further comprises a base pivotally secured to the head and positionable with respect to the head. The base includes an arm extending from the base which is engaged with the drive shaft. The toothbrush also comprises a first bristle carrier disposed on and secured to the base, and a second bristle carrier disposed on the head. Upon reciprocation of the drive shaft, the distal end of the drive shaft moves the arm of the base and causes the base and the first bristle carrier to pivot.

In yet another aspect, the present invention provides an electrically powered toothbrush comprising a body having a first end, a head opposite that end, and a neck extending between the end and the body. The body defines a hollow interior region within the body. The head defines a second hollow interior region within the head. And, the head has an inclined ramp surface along an outer surface of the head. The electrically powered toothbrush also comprises an electrical motor and power source disposed in the hollow region of the body. The motor provides a rotating or oscillating drive shaft. The shaft has a distal end and is offset from a longitudinal axis of the shaft. The toothbrush also comprises a positionable base moveably disposed on the head and in contact with the ramp surface. The base includes an outwardly extending arm that extends into the second hollow interior region of the head. The arm provides a channel within which is disposed the distal end of the drive shaft. The toothbrush also comprises first and second bristle carriers in which the first bristle carrier is secured to the positionable base. Upon rotation or oscillation of the drive shaft, the distal end of the drive shaft moves within the channel provided in the arm of the base. That movement causes the base and the first bristle carrier to move along the ramp surface.

In still another aspect, the present invention provides an electrically powered toothbrush comprising a body having a first end and a head opposite from that end and a neck extending between the end and the head. The body defines a hollow interior region within the body. The head defines a second hollow interior region within the head. The head includes an inclined ramp surface along an outer surface of the head. The toothbrush also comprises an electrical motor and power source disposed in the hollow interior region within the body. The motor provides a reciprocating drive shaft which has a distal end that is offset from a longitudinal axis of the shaft. The toothbrush also comprises a positionable base movably disposed on the head and in contact with the ramp surface. The base includes an outwardly extending arm that extends into the second hollow interior region of the head. The arm defines an aperture within which is disposed the distal end of the shaft. The toothbrush also comprises a first bristle carrier disposed on and secured to the base, and a second bristle carrier disposed on the head. Upon reciprocation of the drive shaft, the distal end of the drive shaft moves the arm of the base and causes the base and the first bristle carrier to move along the ramp surface.

In yet another aspect, the present invention provides an electrically powered toothbrush comprising a body having a first end, a head opposite from that end, and a neck extending between the end and the head. The body defines a hollow interior region. The head defines a second hollow interior region within the head. The head also includes an elongated aperture along an outer surface of the head. The toothbrush also comprises an electrical motor and power source disposed in the hollow region of the body. The motor provides a rotating or oscillating drive shaft which has a distal end. The toothbrush also comprises a screw gear engaged to the distal end of the drive shaft. The screw gear defines a channel along an outer surface of the screw gear. The toothbrush also comprises a positionable base movably disposed on the head and positioned over the elongated aperture defined in the head. The base includes an outwardly extending guide member disposed in and contacting the channel of the screw gear. The guide member extends through the elongated aperture defined along the head. The toothbrush additionally comprises a first bristle carrier disposed on and secured to the base. And, the toothbrush also includes a second bristle carrier disposed on the head. Upon rotation or oscillation of the drive shaft, the screw gear is rotated thereby causing displacement of the guide member, the base, and the first bristle carrier along the outer surface of the head.

In still another aspect, the present invention provides an electrically powered toothbrush comprising a body having an end, a head opposite from that end, and a neck extending between the end and the head. The body defines a hollow interior region within the body. And the head defines a second hollow interior region within the head. The head also provides an elongated aperture along an outer surface of the head. The toothbrush also comprises an electrical motor and power source disposed in the hollow interior region within the body. The motor provides a reciprocating drive shaft which has a distal end. The toothbrush also comprises a positionable base movably disposed on the head and positioned over the elongated aperture defined in the head. The base includes an outwardly extending guide member projecting through the elongated aperture in the head. The guide member engages the distal end of the drive shaft. The toothbrush also comprises a first bristle carrier disposed on and secured to the base. And, the toothbrush includes a second bristle carrier disposed on the head. Upon reciprocation of the drive shaft, the distal end of the drive shaft moves the base and the first bristle carrier along the head.

In yet another aspect, the present invention provides an electrically powered toothbrush comprising a body having a first end, a head opposite that end, and a neck extending between the first end and the head. The body defines a hollow interior region within the body. The head defines a second hollow interior region within the head. The head also defines an elongated aperture along an outer surface of the head. The toothbrush additionally comprises an electrical motor and power source disposed in the hollow interior region within the body. The motor provides a rotating or oscillating drive shaft. The toothbrush also comprises a screw gear engaged with the drive shaft. The screw gear provides a channel along its outer surface. The toothbrush also comprises a base movably disposed on the head and positionable with respect to the head. The base includes an outwardly extending guide member projecting through the elongated aperture and into the second hollow interior region within the head. The guide member is disposed in and contacts the screw gear channel. The toothbrush also comprises first and second bristle carriers disposed on the head. The second bristle carrier is secured to the base. Upon rotation or oscillation of the drive shaft, the screw gear is rotated which causes displacement of the guide member, the base, and the second bristle carrier.

In yet another aspect, the present invention provides an electrically powered toothbrush comprising a body having a first end, a head opposite that end, and a neck extending between the end and the head. The body defines a hollow interior region and the head defines a second hollow interior region. The head also provides an elongated aperture along its outer surface. The toothbrush additionally comprises an electrical motor and power source disposed in the hollow region of the body. The motor provides a reciprocating drive shaft. A toothbrush additionally comprises a positionable base movably disposed on the head. The base includes an outwardly extending guide member that projects through the elongated aperture defined along the head. The guide member extends into the second hollow interior region of the head. The guide member engages the drive shaft. The toothbrush also comprises a first bristle carrier disposed on the head and a second bristle carrier disposed on and secured to the base. Upon reciprocation of the drive shaft, the drive shaft moves the guide member of the base and causes the base and the second bristle carrier to move.

In another aspect, the present invention provides an electrically powered toothbrush comprising a body having a first end, a head opposite that end, and a neck extending between the first end and the head. The body defines a hollow interior region, and the head defines a second hollow interior region and includes internal support members that define a camming aperture within the second hollow interior region of the head. The toothbrush also comprises an electrical motor and power source disposed in the hollow interior region of the body. The motor provides a rotating or oscillating drive shaft. The toothbrush also comprises a screw gear engaged to the distal end of the drive shaft. The screw gear defines a channel along its outer surface. The toothbrush also comprises a positionable base movably disposed on the head. The base includes an outwardly extending arm projecting into the second hollow interior region of the head. The arm includes a laterally extending guide member disposed in and engaging the camming aperture defined in the internal support members of the head. The toothbrush also comprises a linkage assembly having a guide member disposed in the channel of the screw gear. The linkage assembly engages the screw gear to the arm of the base. The toothbrush also comprises a first bristle carrier disposed on and secured to the base. And, the toothbrush comprises a second bristle carrier disposed on the head and between the first bristle carrier and the first end of the body. Upon rotation or oscillation of the drive shaft, the screw gear is rotated thereby causing displacement of the guide member, the linkage assembly, the base, and the first bristle carrier.

In yet another aspect, the present invention provides an electrically powered toothbrush comprising a body having an end, a head opposite that end, and a neck extending between the end and the head. The body defines a hollow interior region within the body, and the head defines a second hollow interior region within the head. The head also includes internal support members that define a camming aperture within the head. The toothbrush additionally comprises an electrical motor and power source disposed in the hollow interior region within the body. The motor provides a reciprocating drive shaft. The shaft has a distal end. The toothbrush also comprises a positionable base movably disposed on the head and including an outwardly extending arm projecting into the second hollow interior region of the head. The arm includes a laterally extending guide member disposed in and engaging the camming aperture defined in the internal support members of the head. The toothbrush also comprises a linkage assembly engaging the end of the drive shaft to the arm of the base. The toothbrush also comprises first and second bristle carriers disposed on the head. The first bristle carrier is secured to the base. Upon reciprocation of the drive shaft, the distal end of the drive shaft moves the arm of the base and causes the base and the first bristle carrier to move.

In yet another aspect, the present invention provides an electrically powered toothbrush comprising a body having an end, a head opposite the end, and a neck extending between the end and the head. The body defines a hollow interior region within the body, and the head defines a second hollow interior region within the head. The head additionally includes internal support members that define a camming aperture within the second interior region of the head. The toothbrush also comprises an electrical motor and power source disposed in the hollow interior region within the body. The motor provides a reciprocating drive shaft. The toothbrush also comprises a positionable base movably disposed on the head. The base includes an outwardly extending arm projecting into the second hollow interior region of the head. The arm includes a laterally extending guide member disposed in and engaging the camming aperture defined in the internal support members of the head. The toothbrush also comprises a linkage assembly engaging the drive shaft to the arm of the base. The toothbrush also comprises first and second bristle carriers disposed on the head. The second bristle carrier is secured to the base. Upon reciprocation of the drive shaft, the drive shaft moves the arm of the base and causes the base and the second bristle carrier to move.

In a still further aspect, the present invention provides an electrically powered toothbrush comprising a body having an end, a head opposite from that end, and a neck extending between the end and the head. The body defines a hollow interior region, and the head defines a second hollow interior region. The head also includes an elongated aperture extending along an outer surface of the head. The toothbrush additionally comprises an electrical motor and power source disposed in the hollow region within the body. The motor provides a rotating or oscillating drive shaft. The toothbrush also comprises a screw gear engaged to the drive shaft. The screw gear defines a channel along its outer surface. The toothbrush also comprises a positionable base movably disposed on the head and positioned over the elongated aperture defined in the head. The base includes an outwardly extending guide member extending through the elongated aperture defined in the head and disposed in the second hollow region of the head. The toothbrush also comprises a linkage assembly disposed in the second hollow region within the head. The linkage assembly has a first end disposed in and contacting the channel of the screw gear, and a second end engaged to the guide member of the base. The toothbrush also comprises first and second bristle carriers disposed on the head. The first bristle carrier is secured to the base. Upon rotation or oscillation of the drive shaft, the screw gear is rotated which causes displacement of the linkage assembly, the guide member, the base and the first bristle carrier along the outer surface of the head.

In yet another aspect, the present invention provides an electrically powered toothbrush comprising a body having a head, an end opposite from the head, and a neck extending between the head and end. The body defines a first hollow interior region, and the head defines a second hollow interior region. The head also provides an outwardly directed surface. The toothbrush also comprises a motor and power source disposed in the first interior region. The motor provides a powered drive shaft. The toothbrush also comprises a plurality of bristle carriers disposed on the outwardly directed surface of the head. The toothbrush additionally comprises a base movably disposed on the outwardly directed surface of the head and engaged to the drive shaft of the motor. At least one of the bristle carriers is engaged with the base. Upon operation of the motor, the base and at least one of the bristle carriers engaged therewith are moved along the head. The head defines an elongated aperture in the outwardly directed surface of the head. The orientation or shape of this aperture governs the movement of the base and the bristle carriers engaged therewith.

In another aspect, the present invention provides an electrically powered toothbrush comprising a body with a head, an end opposite the head, and a neck extending between the head and end. The body defines a first hollow interior region, and the head defines a second hollow interior region. The head also provides an outwardly directed surface. The toothbrush also comprises a motor and power source disposed in the first interior region, the motor providing a powered drive shaft. The toothbrush additionally comprises a plurality of bristle carriers disposed on the outwardly directed surface of the head. The toothbrush further comprises a base movably disposed on the outwardly directed surface of the head and engaged to the drive shaft. At least one of the collection of bristle carriers is engaged with the base. Upon operation of the motor, the base and at least one of the plurality of the bristle carriers engaged therewith are moved along the head. The head defines an inclined ramp surface within the outwardly directed surface of the head which governs the movement of the base and at least one of the bristle carriers of the collection engaged with the base.

BRIEF DESCRIPTION OF THE DRAWINGS

The present invention may take form in various components and arrangements of components, and in various techniques, methods, or procedures and arrangements of steps. The referenced drawings are only for purposes of illustrating preferred embodiments, they are not necessarily to scale, and are not to be construed as limiting the present invention.

It is believed that the present invention will be better understood from the following description taken in conjunction with the accompanying drawings in which:

FIG. 4 is a front elevational view of a preferred embodiment toothbrush in accordance with the present invention;

FIG. 4A is a detail of a first bristle carrier of the toothbrush shown in FIG. 4 illustrating the bristle carrier undergoing a certain type of motion;

FIG. 4B is a detail of a second bristle carrier of the toothbrush shown in FIG. 4 illustrating the bristle carrier undergoing a certain type of motion;

FIG. 4C is a detail of a second bristle carrier of the toothbrush shown in FIG. 4 illustrating the bristle carrier undergoing a certain type of motion;

FIG. 4D is a detail of a second bristle carrier of the toothbrush shown in FIG. 4 illustrating the bristle carrier undergoing a certain type of motion;

FIG. 4E is a detail of a second bristle carrier of the toothbrush shown in FIG. 4 illustrating the bristle carrier undergoing a certain type of motion;

FIG. 6 is a front elevational view of a preferred embodiment toothbrush in accordance with the present invention;

FIG. 6A is a detail of a first bristle carrier of the toothbrush shown in FIG. 6 illustrating the bristle carrier undergoing a certain type of motion;

FIG. 6B is a detail of a second bristle carrier of the toothbrush shown in FIG. 6 illustrating the bristle carrier undergoing a certain type of motion;

FIG. 6C is a detail of a second bristle carrier of the toothbrush shown in FIG. 6 illustrating the bristle carrier undergoing a certain type of motion;

FIG. 6D is a detail of a second bristle carrier of the toothbrush shown in FIG. 6 illustrating the bristle carrier undergoing a certain type of motion;

FIG. 6E is a detail of a second bristle carrier of the toothbrush shown in FIG. 6 illustrating the bristle carrier undergoing a certain type of motion;

FIG. 1G is a cross-section taken along line 11G in FIG. 11F;

FIG. 15D is a schematic view of a preferred embodiment toothbrush in accordance with the present invention illustrating another mechanism for imparting motion to a bristle carrier;

FIG. 15E is a schematic cross-sectional view of the mechanism shown in FIG. 15D;

FIG. 15F is a cross-sectional view taken along line 15F in FIG. 15E;

FIG. 21A is a schematic view of a preferred embodiment toothbrush in accordance with the present invention illustrating another mechanism for imparting motion to a bristle carrier;

FIG. 21B is a schematic cross-sectional view of the mechanism illustrated in FIG. 21A;

FIG. 21C is a cross-sectional view taken along line 21C in FIG. 21B;

DETAILED DESCRIPTION OF THE PREFERRED EMBODIMENTS

As will be appreciated, the present invention is directed to electric toothbrushes, including electric toothbrushes having replaceable brush head ends, replaceable bristle carriers and electric toothbrushes having multiple bristle carriers. In particular, the present invention is directed to an electric toothbrush with two bristle carriers, each of which is driven by an electric motor incorporated within the toothbrush body. As described in greater detail herein, it is contemplated that two or more electric motors could be utilized in the present invention toothbrush.

Specifically, the present invention can be used in conjunction with electric toothbrushes, brush heads, and bristle carriers that include shafts that rotate, oscillate, or reciprocate (as well as combinations thereof) to impart motion to the first and second bristle carriers. In addition, the present invention can be used in combination with electric toothbrushes, brush heads, and bristle carriers where the shaft is operatively connected to both the first and second bristle carriers or only one of the bristle carriers. In the latter instance, the bristle carriers are themselves interconnected so that a motion is imparted to the bristle carrier that is not directly coupled to the shaft.

Before describing the various preferred embodiment toothbrushes and associated drive mechanisms, it is instructive to define the various types of motions referenced herein. As used herein, the term "angular motion" refers to any angular displacement. "Linear motion" is movement along a straight or substantially straight, line or direction. "Primarily linear motion" is described below. "Curvilinear motion" is movement that is neither completely linear nor completely angular but is a combination of the two (e.g., curvilinear). These motions can be constant or periodic. Constant motion refers to motion that does not change direction or path (i.e., is unidirectional). Periodic motion refers to motion that reverses direction or path. Constant angular motion (i.e., motion that extends through 360 degrees or more) that is substantially in the form of a circle is referred to as rotary motion. Periodic angular motion is motion that extends through less than 360 degrees and is referred to as oscillating motion. Curvilinear motions can also be either constant (i.e., unidirectional) or periodic (i.e., reverses direction). Periodic linear motion is referred to as "reciprocation".

Figure 1:
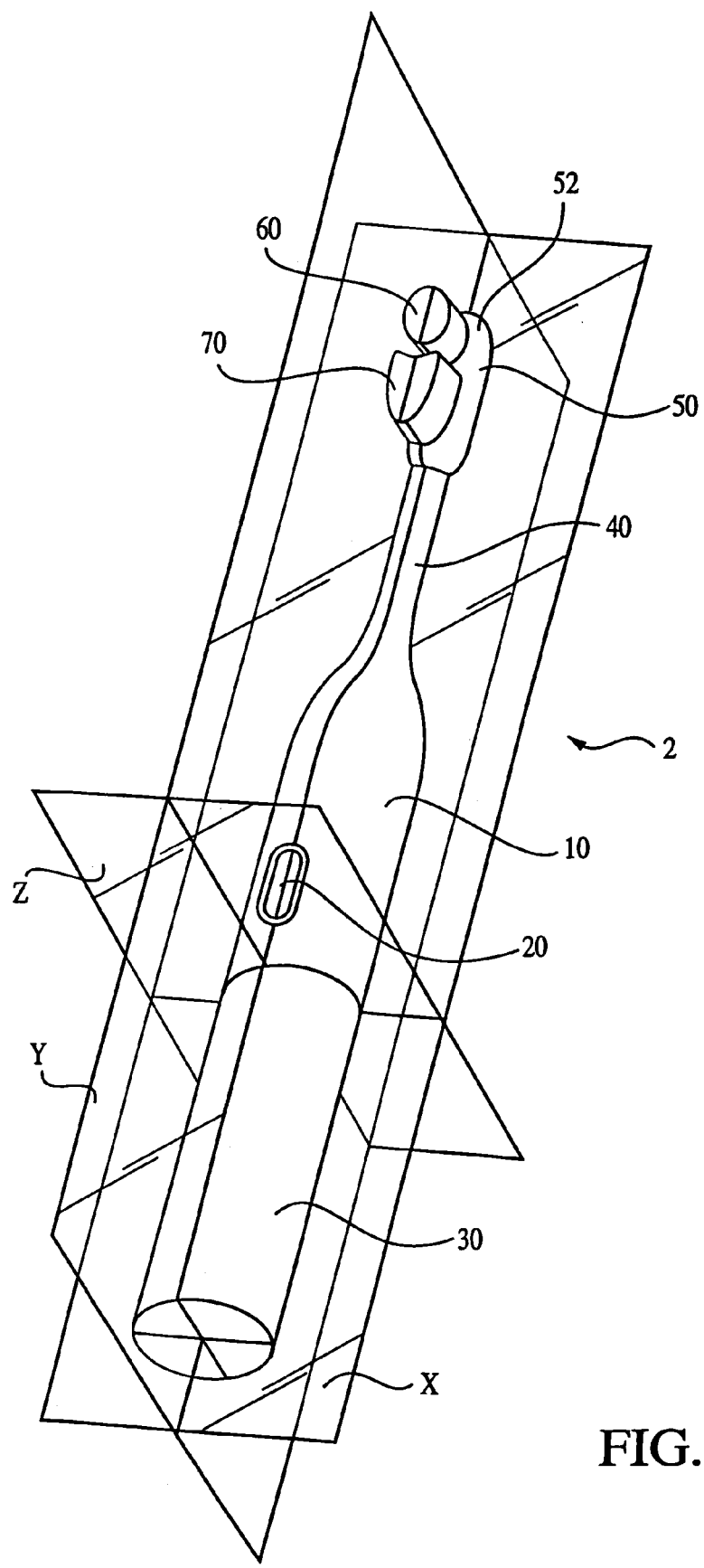
FIG. 1 is a perspective view of a preferred embodiment toothbrush in accordance with the present invention illustrating various planes and their orientation with respect to the toothbrush.

The above-described motions can also occur along one or more axes of a bristle carrier. Accordingly, motion is described herein as being either one, two, or three dimensional motion depending upon the number of axial coordinates required to describe the position of a bristle carrier during its movement. The axes, X, Y, and Z, are shown in FIG. 1. One dimensional motion is motion that can be described by a single coordinate (e.g., X, Y, or Z coordinates). Typically, only linear motion can be one dimensional. For example, periodic linear motion substantially along only the Y axis is one dimensional motion (referred to herein as a "pulsing motion"). Two dimensional motion is movement by a bristle carrier that requires two coordinates (e.g., X and Y coordinates) to describe the path of travel of the bristle carrier. Angular motion that occurs in a single plane is two dimensional motion. Three dimensional motion is movement by a bristle carrier that requires three coordinates (e.g., X, Y, and Z coordinates) to describe the path of travel of the bristle carrier. An example of three dimensional motion is movement by a bristle carrier in the path of a helix.

FIG. 1 is a perspective view of a preferred embodiment toothbrush 2 in accordance with the present invention. The toothbrush 2 comprises an elongated body 10 having a handle 30, a head 50, and a neck 40 extending between the handle 30 and the head 50. A switch 20 is provided or made accessible along the outer region of the body 10. As will be appreciated, the switch 20 actuates an electrical motor contained within the body 10 of toothbrush 2. The motor (not shown) and a drive mechanism as described herein (not shown) provide a powered drive for one or more bristle carriers disposed near a distal end of the toothbrush. Specifically, the toothbrush 2 further includes a first bristle carrier 60 and a second bristle carrier 70 located adjacent a distal-most end 52. As described in greater detail herein, upon activation of the drive mechanism, the first and second bristle carriers undergo a particular combination of motions. The motions are best described in terms of the axes X, Y, and Z and the planes which contain these axes.

The X axis is generally referred to herein as the longitudinal axis and generally extends along a longitudinal or lengthwise dimension (as seen from the top planar view of the toothbrush) of the toothbrush head or the bristle carrier. The longitudinal axis of the toothbrush head or bristle carrier may coincide with the longitudinal axes of the toothbrush neck and/or handle, although it need not do so as for example where the toothbrush head is angled with respect to either the toothbrush neck or handle. For example, a longitudinal axis is an axis passing through the longest dimension of the toothbrush head. The Y axis is transverse to the X axis and generally bisects the toothbrush head into its left and right halves. The Z axis is orthogonal or perpendicular to the X and Y axes.

Plane X contains the X axis and is generally referred to herein as the plane of the toothbrush or the plane of the toothbrush head. This plane generally extends along the longitudinal dimension of the toothbrush or the toothbrush head. The Y plane contains the Y axis and extends through the toothbrush and is perpendicular to the X plane. The Y plane either bisects the toothbrush or is parallel to a plane that does. The Z plane is perpendicular to both the X plane and the Y plane.

Furthermore, it is useful to address the terminology used in describing the preferred embodiment toothbrushes, bristle carriers, and the various drive mechanisms. As used herein, the term "forward" refers to the direction from the handle to the head while the term "rearward" refers to the direction from the head to the handle. A longitudinal direction is a direction that generally corresponds to a longitudinal or X axis but which may not lie in the same plane as the axis. For example, the longitudinal axes of a shaft and a bristle carrier may not extend in the same plane but generally extend in the same direction from a top planar view. Similarly, a neck and head that are angled with respect to each other may not have longitudinal axes that extend in the same plane, but do have axes which extend in the same general longitudinal direction from a top planar view. Many of the preferred embodiment electric toothbrushes typically have an elongated head with a longitudinal axis passing through the longest dimension thereof. This axis typically extends in the same general direction as the longitudinal axes of the toothbrush neck and/or shaft. This axis is generally referred to as the longitudinal axis of the toothbrush. By the phrase "same general direction," some angular deviation is contemplated between the axes. Various references are also made herein to the "plane of the toothbrush." As will be understood, this is generally the plane within which extends the longitudinal axis of the toothbrush head.

And, as described herein, the first bristle carrier is the bristle carrier that is located at the distal-most end of the toothbrush. The second bristle carrier is the next bristle carrier positioned alongside or proximate to the first bristle carrier and rearward therefrom. A third bristle carrier is proximate the second bristle carrier and is positioned rearward of the second bristle carrier. A fourth bristle carrier is rearward of the third and so on.

Generally, the preferred embodiment toothbrushes according to the present invention comprise an elongated hollow body that retains an electrically powered motor and drive mechanism that is used to drive two or more moveable bristle carriers. The elongated hollow body also includes an interior chamber for containing one or more batteries for powering the motor. And, one or more switches are provided along the outer region of the body for activating the motor and drive mechanism. As will be appreciated, a removable end cap is provided to enclose the interior chamber and provide a seal against external agents for the components inside the toothbrush body. As described in detail herein, the preferred embodiment toothbrushes comprise two or more movable bristle carriers. Each of the bristle carriers undergoes particular types of motion and the resulting combinations of movements provide unique cleaning efficacy.

As noted, the preferred embodiment electric toothbrushes comprise a plurality of bristle carriers that are driven by an electric motor and drive mechanism incorporated in the toothbrush. Preferably, these toothbrushes utilize two bristle carriers, each undergoing motion different than the motion of the other bristle carrier. Specifically, there are numerous categories of combinations of movements of the two bristle carriers which are encompassed by the present invention. Each of these categories involves various specific types of combinations of movement as follows.

A first category of combinations of movements of the two bristle carriers is that in which the first or distal-most bristle carrier moves in a linear fashion, and the second bristle carrier moves in a primarily linear fashion. Specifically, this category involves motion in which the first bristle carrier undergoes one dimensional periodic, i.e. repeated, linear movement in combination with two or three dimensional periodic primarily linear movement by the second bristle carrier. It will be appreciated that the reference to "primarily linear" refers to movement that is in two or three dimensions and not entirely linear in nature. Movement that is primarily linear is movement that is best characterized as non-linear movement, however movement that is substantially along a single axis, line or direction. That is, primarily linear motion is movement that is generally along a single line or direction. This motion may include deviation from the line or direction of movement, however such motion is substantially linear.

This combination of movements may be further defined as involving one of the following specific types of movement by the first bristle carrier and one of the following specific types of movement by the second bristle carrier.

The first bristle carrier may reciprocate along a single axis or line in the X plane of the toothbrush head or a plane that is generally parallel to the plane of the toothbrush head, and in a direction parallel to the longitudinal axis of the toothbrush head. Or, the first bristle carrier may reciprocate along a single axis or line in the X plane of the toothbrush head or a plane generally parallel to the plane of the toothbrush head, and in a direction perpendicular to the longitudinal axis of the toothbrush head (and so the first bristle carrier moves in a "side-to-side" fashion). Alternately, the first bristle carrier may reciprocate along a single axis in the X plane of the toothbrush head or a plane generally parallel to the X plane of the toothbrush head, and in a direction other than parallel or perpendicular to the longitudinal axis of the toothbrush head. That is, the first bristle carrier may reciprocate along an axis that extends at an acute angle with respect to the longitudinal axis of the toothbrush head. Instead, the first bristle carrier may reciprocate along a single axis in a plane perpendicular to the X plane of the toothbrush head (and so, moving in an "up and down" or "pulsing" fashion). In other words, the first bristle carrier may move in a direction aligned with the Y axis of the toothbrush head. Yet another motion is that in which the first bristle carrier may reciprocate along a single axis in a plane other than one that is parallel or perpendicular to the X plane of the toothbrush head. All of these motions of the first bristle carrier are one dimensional or linear.

The second bristle carrier may undergo repeated motion that is primarily linear within the X plane of the toothbrush head or a plane generally parallel to the X plane of the toothbrush head. Or, the second bristle carrier may undergo repeated motion that is primarily linear and in a plane that is perpendicular to the X plane of the toothbrush head (and so, the second bristle carrier would resemble a "pulsing" type motion). Or, the second bristle carrier may undergo repeated motion that is primarily linear in a plane other than one that is parallel or perpendicular to the plane of the toothbrush head. Alternatively, the second bristle carrier may undergo repeated motion that is primarily linear and non-planar (hence, the designation that motion of the second bristle carrier is in three dimensions). This motion of the second bristle carrier, although non-planar, can be characterized by primarily extending within a plane that is: (i) within the plane of the toothbrush head or a plane that is generally parallel to the plane of the toothbrush head; (ii) perpendicular to the plane of the toothbrush head; or (iii) different than either the plane of the toothbrush head or a plane perpendicular thereto.

It will be understood that in this category of movement combinations, any of the previously described movements of the first bristle carrier may be utilized in conjunction with any of the previously described movements of the second bristle carrier.

Figure 2A:
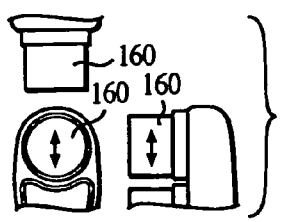
FIG. 2A is a detail of a first bristle carrier of the toothbrush shown in FIG. 2 illustrating the bristle carrier undergoing a certain type of motion.
Figure 2B:
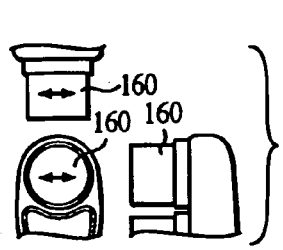
FIG. 2B is a detail of a first bristle carrier of the toothbrush shown in FIG. 2 illustrating the bristle carrier undergoing a certain type of motion.
Figure 2C:
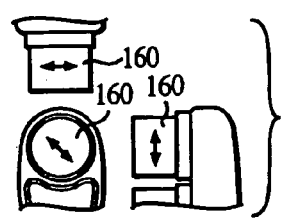
FIG. 2C is a detail of a first bristle carrier of the toothbrush shown in FIG. 2 illustrating the bristle carrier undergoing a certain type of motion.
Figure 2D:
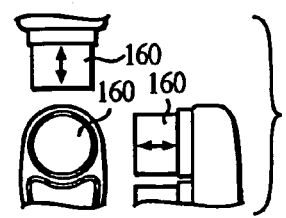
FIG. 2D is a detail of a first bristle carrier of the toothbrush shown in FIG. 2 illustrating the bristle carrier undergoing a certain type of motion.
Figure 2E:
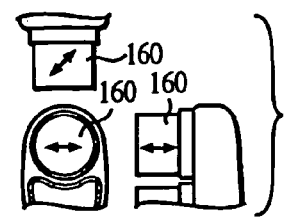
FIG. 2E is a detail of a first bristle carrier of the toothbrush shown in FIG. 2 illustrating the bristle carrier undergoing a certain type of motion.
Figure 2:
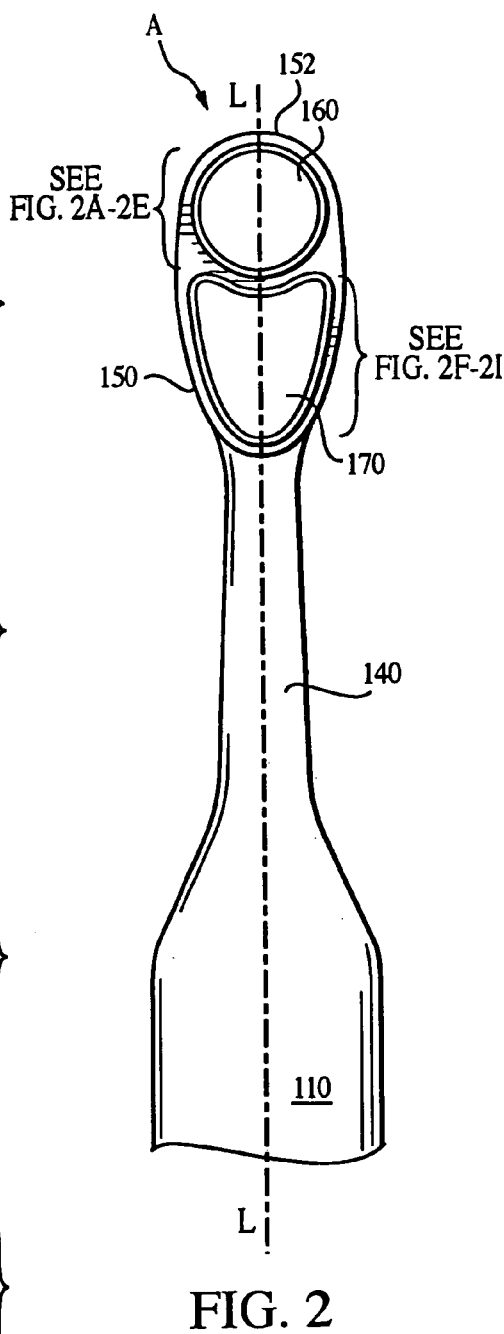
FIG. 2 is a front elevational view illustrating the bristle carriers of a preferred embodiment toothbrush in accordance with the present invention.

FIG. 2 illustrates a preferred embodiment toothbrush A having a pair of bristle carriers as previously described. FIGS. 2A to 2I illustrate the various combinations of movements of these bristle carriers as previously described. Specifically, FIG. 2 illustrates a preferred embodiment toothbrush A including a body 110 having a neck 140 and a head 150. The toothbrush A further includes a first bristle carrier 160 and a second bristle carrier 170 disposed proximate to a distal-most end 152 of the head 150. The first bristle carrier 160 may be configured to move in a variety of fashions as previously noted. Specifically, referring to FIGS. 2A to 2E these motions are as follows.

FIG. 2A illustrates that the first bristle carrier 160 may reciprocate along a single axis or line in the plane of the toothbrush head such as plane X as shown in FIG. 1, or a plane that is generally parallel to the plane of the toothbrush head, and in a direction parallel to the longitudinal axis L of the toothbrush. FIG. 2B illustrates another motion in which the first bristle carrier 160 reciprocates along a single axis or line in the plane of the toothbrush head or a plane generally parallel to the plane of the toothbrush head, and in a direction perpendicular to the longitudinal axis of the toothbrush. FIG. 2B illustrates the first bristle carrier 160 moving in a "side-to-side" fashion. FIG. 2C illustrates the first bristle carrier 160 reciprocating along a single axis in the plane of the toothbrush head or a plane generally parallel to the plane of the toothbrush head, and in a direction other than parallel or perpendicular to the longitudinal axis of the toothbrush. That is, FIG. 2C illustrates the first bristle carrier 160 reciprocating along an axis that extends at an acute angle with respect to the longitudinal axis of the toothbrush. FIG. 2D illustrates the first bristle carrier 160 reciprocating along a single axis in a plane perpendicular to the plane of the toothbrush head, such as plane Y as shown in FIG. 1, and generally perpendicular to the longitudinal axis of the toothbrush, and so moving in an up and down or pulsing fashion. FIG. 2E illustrates the first bristle carrier 160 moving or reciprocating along a single axis in a plane other than one that is parallel or perpendicular to the plane of the toothbrush head. All of these motions of the first bristle carrier 160 are one dimensional or linear.

Figure 2F:
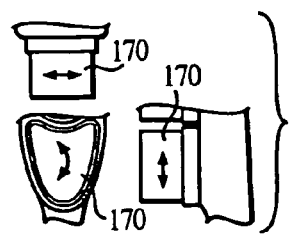
FIG. 2F is a detail of a second bristle carrier of the toothbrush shown in FIG. 2 illustrating the bristle carrier undergoing a certain type of motion.
Figure 2G:
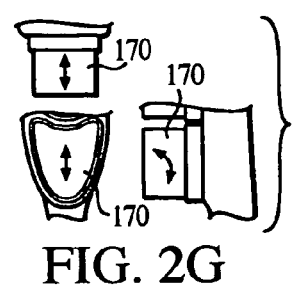
FIG. 2G is a detail of a second bristle carrier of the toothbrush shown in FIG. 2 illustrating the bristle carrier undergoing a certain type of motion.
Figure 2H:
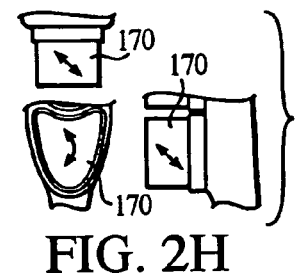
FIG. 2H is a detail of a second bristle carrier of the toothbrush shown in FIG. 2 illustrating the bristle carrier undergoing a certain type of motion.
Figure 2I:
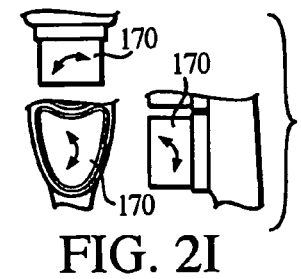
FIG. 2I is a detail of a second bristle carrier of the toothbrush shown in FIG. 2 illustrating the bristle carrier undergoing a certain type of motion.

FIGS. 2F to 2I illustrate various motions that the second bristle carrier 170 may undergo. FIG. 2F illustrates the second bristle carrier 170 undergoing motion that is primarily linear and so, not one dimensional, within the plane of the toothbrush head or a plane generally parallel to the plane of the toothbrush head. FIG. 2G illustrates the second bristle carrier 170 undergoing repeated motion that is primarily linear and in a plane that is perpendicular to the plane of the toothbrush head, such as plane Y shown in FIG. 1. And so, the second bristle carrier 170 is moving in a motion that resembles a pulsing type motion. FIG. 2H illustrates the second bristle carrier 170 undergoing repeated motion that is primarily linear in a plane other than one that is parallel or perpendicular to the plane of the toothbrush head. FIG. 2I illustrates the second bristle carrier 170 undergoing repeated motion that is primarily linear, however, non-planar, and hence three dimensional.

The preferred embodiment toothbrush A may be configured such that the first bristle carrier 160 may undergo any of the motions depicted in FIGS. 2A to 2E, in combination with the second bristle carrier 170 undergoing any of the motions depicted in FIGS. 2F to 2I.

Figure 14A:
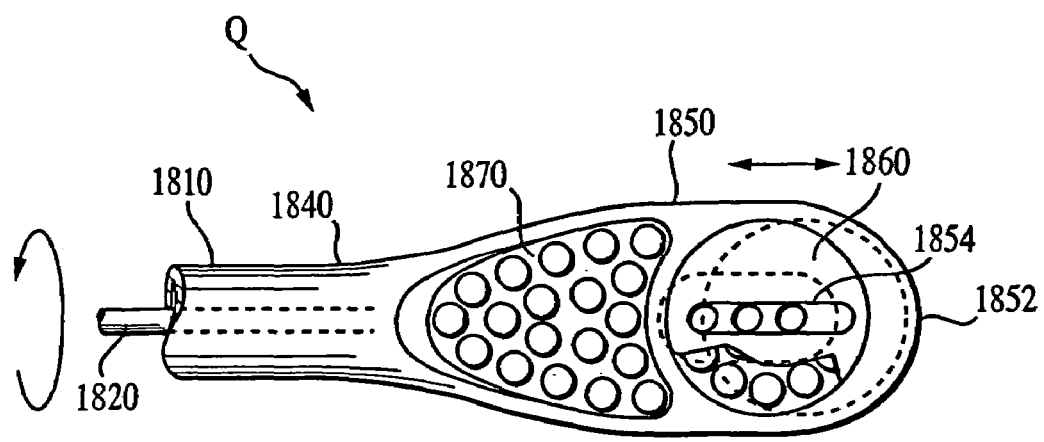
FIG. 14A is a schematic view of a preferred embodiment toothbrush in accordance with the present invention illustrating another mechanism for imparting motion to a bristle carrier.
Figure 14B:
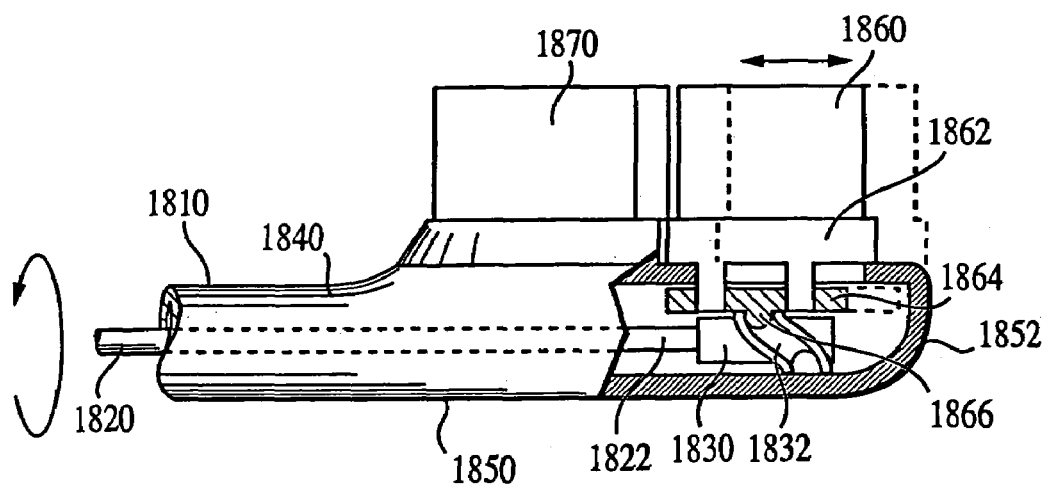
FIG. 14B is a schematic cross-sectional view of the mechanism shown in FIG. 14A.
Figure 14C:
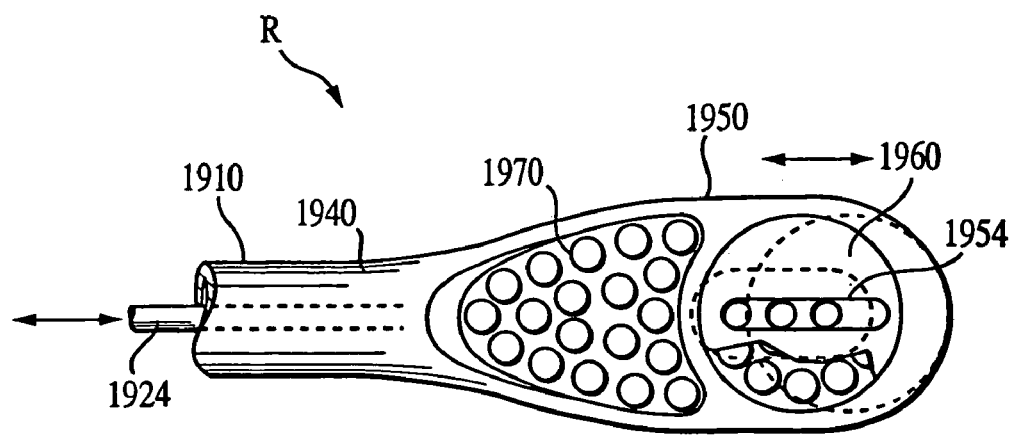
FIG. 14C is a schematic view of a preferred embodiment toothbrush in accordance with the present invention illustrating another mechanism for imparting motion to a bristle carrier.
Figure 14D:
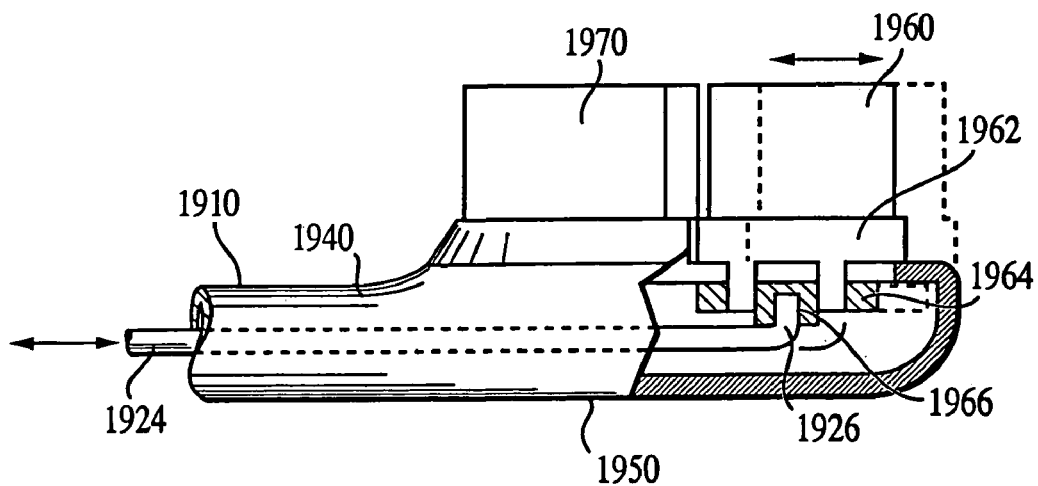
FIG. 14D is a schematic cross-sectional view of the mechanism shown in FIG. 14C.

FIGS. 14A to 14D illustrate two preferred embodiment mechanisms for achieving the motion illustrated in FIG. 2A. FIGS. 14A and 14B illustrate a mechanism utilizing a rotating or oscillating drive shaft, such as from a motor or drive output. FIG. 14C and FIG. 14D illustrate drive mechanisms for use with a reciprocating powered drive shaft. Specifically, FIGS. 14A and 14B illustrate a preferred embodiment toothbrush Q having a body 1810, a neck 1840, and a head 1850. Disposed along the head 1850 is a first bristle carrier 1860 and a second bristle carrier 1870. The body 1810 houses a rotating or oscillating drive shaft 1820 having a distal end 1822. A gear member 1830 is engaged or otherwise secured to the distal end 1822 of the shaft 1820. The gear member 1830 defines a channel 1832 within which a tracking or guide member 1866 is positioned. The first bristle carrier 1860 includes a base 1862, a plate 1864, and the tracking member 1866 extending from the plate 1864. The base may be unitary and not utilize a plate component. Accordingly, the base would include the tracking or guide member. The tracking member 1866 is generally disposed within the channel 1832 of the gear member 1830. The head 1850 defines a guide channel or elongated aperture 1854 along an upwardly directed surface of the head 1850. Upon rotation or oscillation of the shaft 1820, the gear member 1830 is similarly moved. As the gear member 1830 is rotated or oscillated, the tracking member 1866 is linearly displaced as it moves within the channel 1832. Thus, the plate 1864 and the base 1862 of the first bristle carrier 1860 are laterally displaced within the head 1850. This in turn moves the first bristle carrier 1860. The guide channel 1854 defined along an upwardly directed surface of the head 1850 further governs the path of motion of the first bristle carrier 1860.

FIGS. 14C and 14D illustrate a preferred embodiment toothbrush R in accordance with the present invention. This toothbrush R achieves the motion depicted in FIG. 2A. FIGS. 14C and 14D illustrate the toothbrush R having a body 1910, including a neck 1940, and a head 1950. Disposed along the head 1950 is a distal-most or first bristle carrier 1960 and a second bristle carrier 1970. The body 1910 encloses a reciprocating shaft 1924 having a distal end 1926. The first bristle carrier 1960 includes a base component 1962, a plate 1964, and a retention member 1966 disposed along the underside of the plate 1964. The distal end 1926 of the shaft 1924 is engaged with the retention member 1966. Defined along an upwardly directed surface of the head 1950, is a guide channel or elongated aperture 1954. The base is positionable and moveably disposed on the head. The base is positioned over the guide channel. The base may be of a unitary construction and not utilize a separate retention member component. Upon operation or reciprocation of the shaft 1924, the first bristle carrier 1960 is linearly displaced due to motion by the retention member 1966, the plate 1964, and the base 1962. The guide channel 1954 ensures or facilitates linear movement in the desired direction.

Figure 8A:
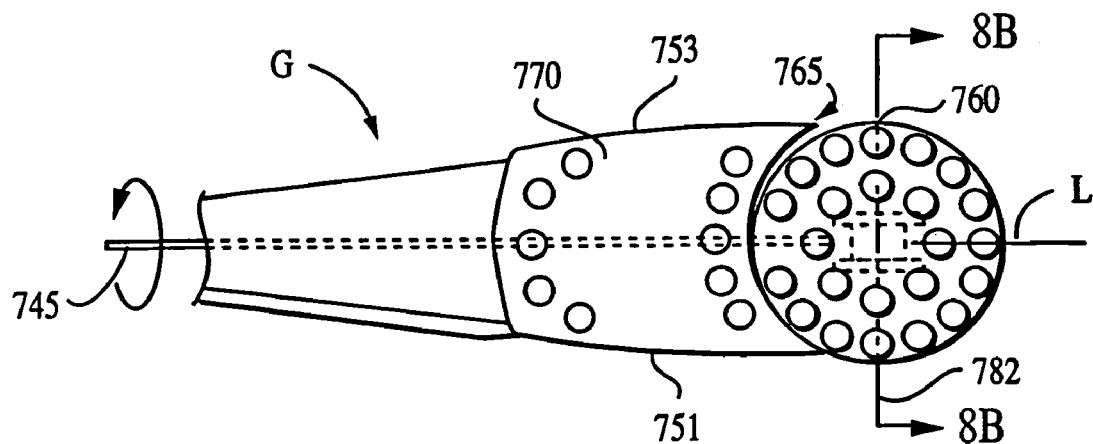
FIG. 8A is a schematic view of a preferred embodiment toothbrush in accordance with the present invention, illustrating another mechanism for imparting motion to a bristle carrier.
Figure 8B:
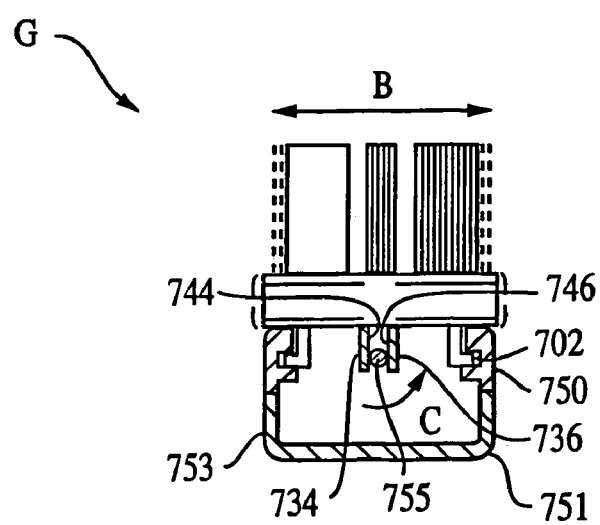
FIG. 8B is a schematic cross-sectional view taken along line 8B—8B in FIG. 8A.

FIGS. 8A–8B illustrate a mechanism for achieving motion shown in FIG. 2B. As previously noted, that motion is the first bristle carrier moving in a "side-to-side" fashion. The mechanism of FIG. 8A–8B is described in greater detail herein.

Figure 15A:
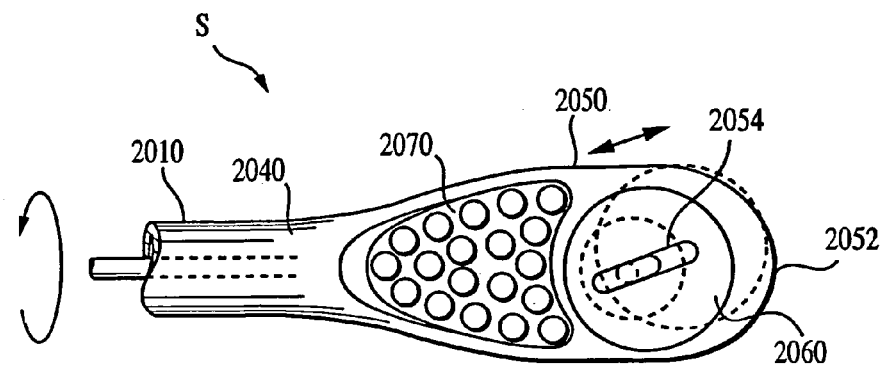
FIG. 15A is a schematic view of a preferred embodiment toothbrush in accordance with the present invention illustrating another mechanism for imparting motion to a bristle carrier.
Figures 15B, 15C:
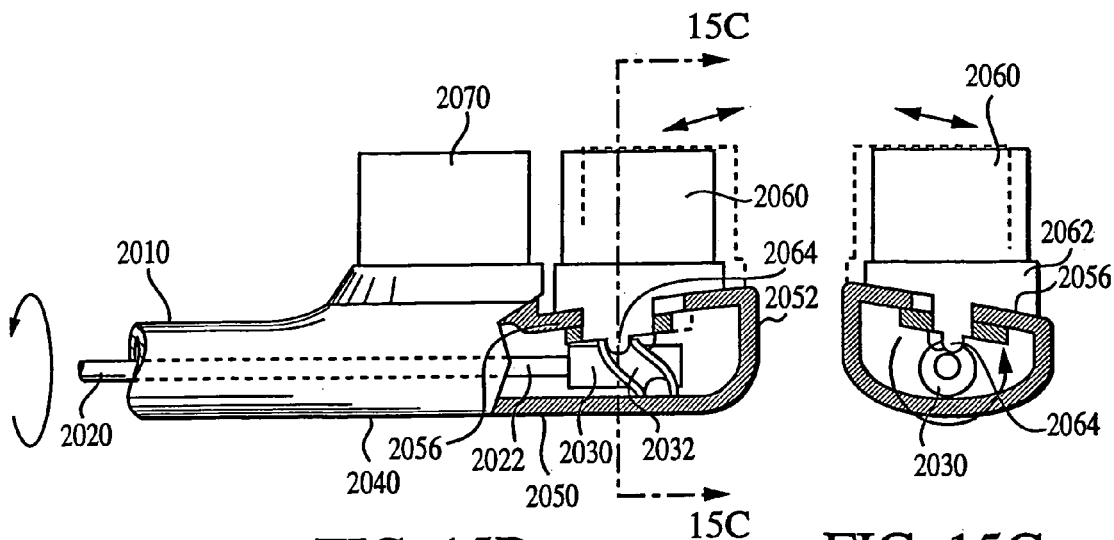
FIG. 15B is a schematic cross-sectional view of the mechanism shown in FIG. 15A.
FIG. 15C is a cross-sectional view taken along line 15C in 15B.

FIGS. 15A to 15F illustrate two mechanisms for achieving the motion shown in FIG. 2C. FIGS. 15A to 15C illustrate a mechanism for achieving motion using a rotating or oscillating drive shaft. FIGS. 15D to 15F illustrate a mechanism for achieving the noted motion by using a reciprocating shaft. Specifically, FIGS. 15A to 15C illustrate a preferred embodiment toothbrush S having a body 2010, a neck 2040, and a head 2050. Disposed along the head 2050 is a distal-most or first bristle carrier 2060 and a second bristle carrier 2070. The distal-most first bristle carrier 2060 is located near a distal-most end 2052 of the head 2050. The body 2010 encloses a rotating or oscillating shaft 2020 having a distal end 2022. Engaged or otherwise secured to the distal end 2022 of the shaft 2020 is a gear member 2030. The gear member 2030 includes a channel 2032 within which is disposed a tracking member described below. The first bristle carrier 2060 includes a base 2062 and a downwardly extending tracking or guide member 2064. As noted with reference to FIGS. 12A–12C, the base may be of a unitary construction and not utilize a separate plate component. As noted, the tracking member 2064 is retained or otherwise disposed in the channel 2032 of the gear member 2030. The head 2050 provides an inclined ramp surface 2056 along which is defined a guide channel or elongated aperture 2054. During operation and oscillation or rotation of the shaft 2020, the gear member 2030 is also similarly moved. This in turn causes linear displacement of the base 2062 by tracking member 2064 moving within the channel 2032. Linear displacement of the base 2062 in turn causes linear displacement of the first bristle carrier 2060. A vertical component to this motion is imparted to the bristle carrier 2060 by the inclined ramp surface 2056. Further modification to the direction of travel motion of the first bristle carrier 2060 is imparted by the orientation of the guide channel 2054.

FIGS. 15D to 15F illustrate a preferred embodiment drive mechanism for achieving the noted motion shown in FIG. 2C using a reciprocating powered shaft. FIGS. 15D to 15F illustrate a preferred embodiment toothbrush T having a body 2110, including a neck 2140, and a head 2150. Disposed along the head 2150 is a first bristle carrier 2160 and a second bristle carrier 2170. The first bristle carrier 2160 is disposed near the distal-most end 2152 of the head 2150. The body encloses a reciprocating shaft 2124 having a distal end 2126. The first bristle carrier 2160 includes a base 2162 and a retention member 2164. The retention member 2164 is engaged or otherwise affixed to the distal end 2126 of the shaft 2124. Alternatively, a link member 2176 may be used to secure or engage the distal end 2126 of the shaft 2124 to the retention member 2164. The head 2150 includes an inclined ramp surface 2156 within which is defined a guide channel or elongated aperture 2154. The base is positionable and moveably disposed on the head. The base is positioned over the guide channel. The base may be of a unitary construction and not utilize a separate retention member component. Upon operation, the shaft 2124 reciprocates and causes linear displacement of the base 2162 by the connection between the retention member 2164 and the distal end 2126 of the shaft 2124. A vertical component of motion is imparted to the movement of the first bristle carrier 2160 by the inclined ramp surface 2156. Furthermore, a desired direction of travel of the first bristle carrier 2160 is achieved by the guide channel 2154, or rather its orientation along the upwardly directed surface of the head 2150.

FIGS. 7A–7D illustrate a mechanism for achieving motion shown in FIG. 2D. As noted, that motion is the first bristle carrier moving in a "pulsing" fashion. The mechanism of FIGS. 7A–7D is described in greater detail herein.

Figure 11D:
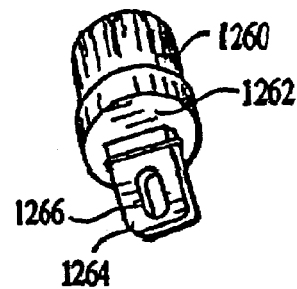
FIG. 11D is a perspective view of a first bristle carrier of the mechanism shown in FIGS. 11A to 11C.
Figure 11A:
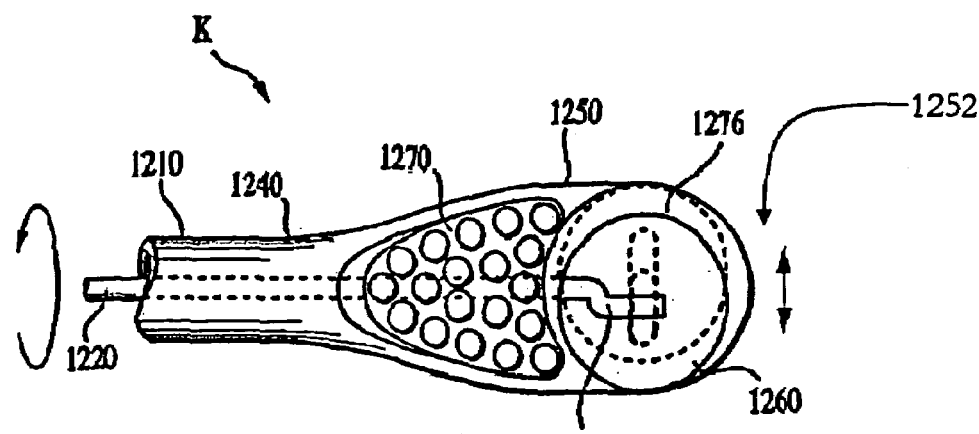
FIG. 11A is a schematic view of a preferred embodiment toothbrush in accordance with the present invention illustrating another mechanism for imparting motion to a bristle carrier.
Figures 11B, 11C:
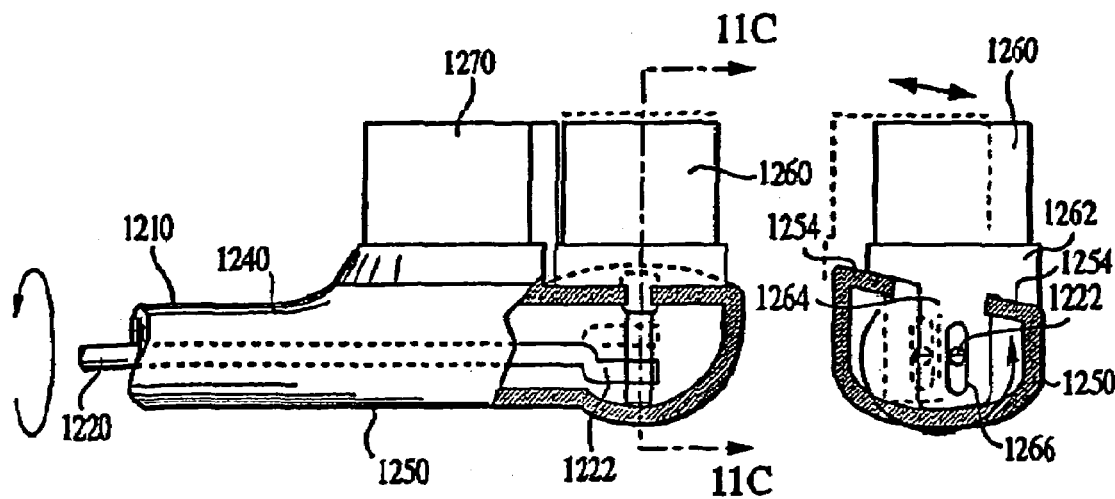
FIG. 11B is a schematic cross-section of the mechanism illustrated in FIG. 1A.
FIG. 11C is a cross-section taken along line 11C in FIG. 11B.
Figure 11E:
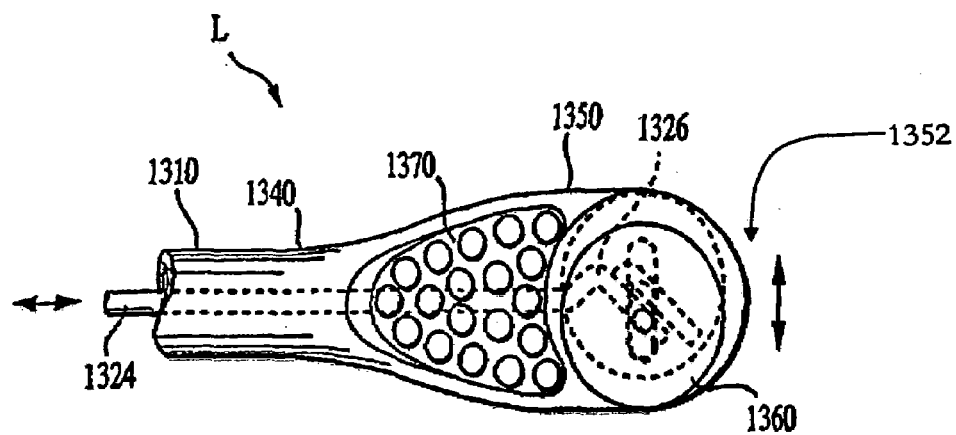
FIG. 11E is a schematic view of a preferred embodiment toothbrush in accordance with the present invention illustrating another mechanism for imparting motion to a bristle carrier.
Figures 11F, 11G:
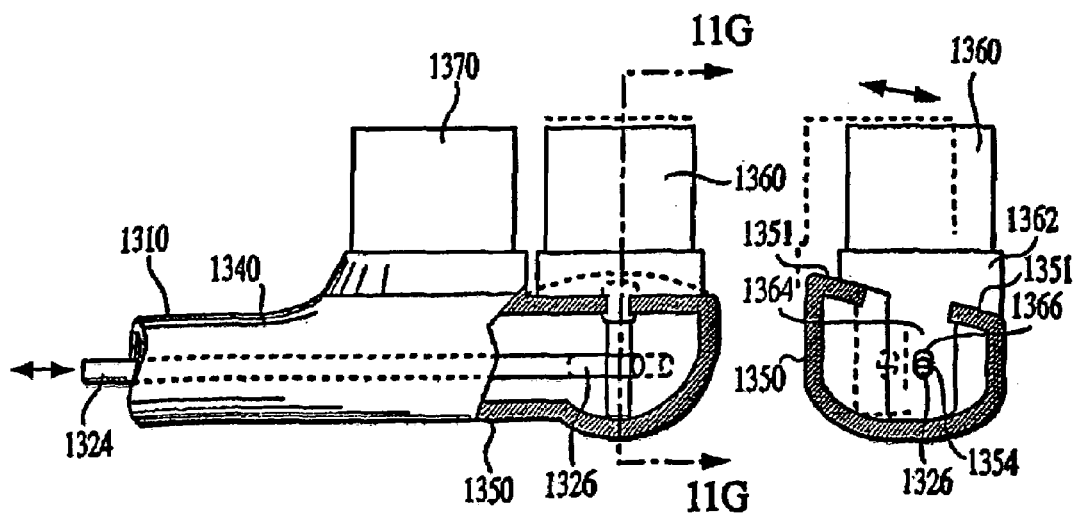
FIG. 11F is a schematic cross-sectional view of the mechanism illustrated in FIG. 11E.

FIGS. 11A to 11G illustrate two preferred mechanisms for achieving the motion illustrated in FIG. 2E. FIGS. 11A to 11D illustrate a mechanism powered by a rotating or oscillating shaft. FIGS. 11E to 11G illustrate a mechanism powered by a reciprocating shaft. Specifically, FIGS. 11A to 11D illustrate a preferred embodiment toothbrush K having a body 1210 including a neck 1240 and a head 1250. Provided along the head 1250 is a distal-most or first bristle carrier 1260 and a second bristle carrier 1270. The first bristle carrier 1260 is located near the distal-most end 1252 of the head 1250. The body 1210 encloses a rotating shaft 1220 having an offset end 1222. The first bristle carrier 1260 has a base 1262 with an outwardly extending arm 1264 that defines a receiving channel 1266. The offset end 1222 of the shaft 1220 is engaged with and generally disposed within the receiving channel 1266 of the base 1262 of the first bristle carrier 1260. Upon rotation of the shaft 1220, the offset end 1222 causes lateral displacement of the first bristle carrier 1260. Specifically, the resulting motion of the first bristle carrier is perpendicular to the longitudinal axis of the toothbrush head 1250. A clearance 1276 is provided within the head 1250 to allow for movement of the first bristle carrier 1260. It will be appreciated that as the shaft 1220 rotates, the first bristle carrier 1260 is laterally displaced in a side-to-side type motion. Motion in a direction that is oriented at some angle to the plane of the toothbrush head may be achieved by providing a ramp surface 1254 along the upwardly directed surface of the head 1250. This is best shown in FIG. 11C. Thus, as the shaft 1220 rotates, the side-to-side movement of the bristle carrier 1260 is further translated along an incline from the ramp surface 1254. Preferably, the base is positionable and movably disposed on the head and in contact with the ramp surface.

Referring to FIGS. 11E to 11G, a second mechanism is illustrated for achieving a motion corresponding to that illustrated in FIG. 2E. Specifically, FIGS. 11E to 11G illustrate a preferred embodiment toothbrush L having a body 1310 including a neck 1340 and a head 1350. A first bristle carrier 1360 is disposed near a distal-most end 1352 of the head 1350. And, a second bristle carrier 1370 is provided next to the first bristle carrier 1360. The body 1310 encloses a reciprocating shaft 1324 having an offset end 1326. The first bristle carrier 1360 includes a base 1362 having a downwardly extending arm 1364 which defines a receiving channel 1366. The offset end 1326 of the shaft 1324 is engaged with and generally disposed within the channel 1366. The head 1350 defines an upwardly directed ramp surface 1351. Preferably, the base is positionable and moveably disposed on the head and in contact with ramp surface. In operation, as the shaft 1324 reciprocates, the first bristle carrier 1360 is translated or reciprocated along the head 1350 and in a direction generally parallel to the inclination of the ramp surface 1351.

Figure 16A:
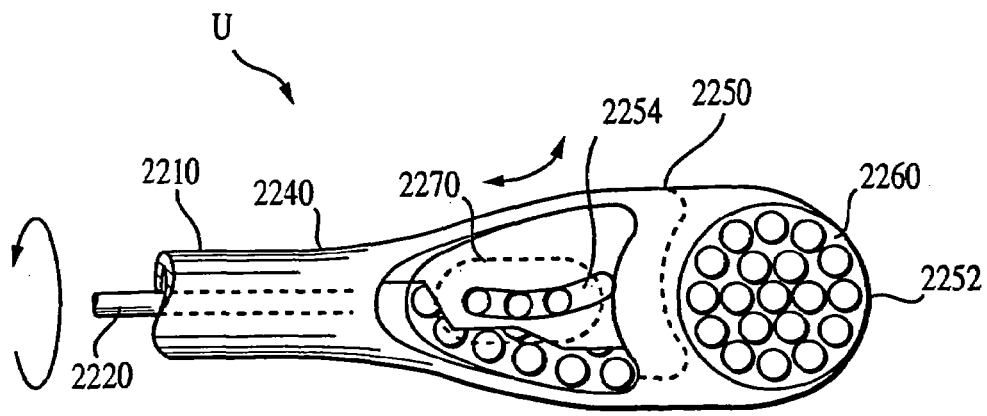
FIG. 16A is a schematic view of a preferred embodiment toothbrush in accordance with the present invention illustrating another mechanism for imparting motion to a bristle carrier.
Figure 16B:
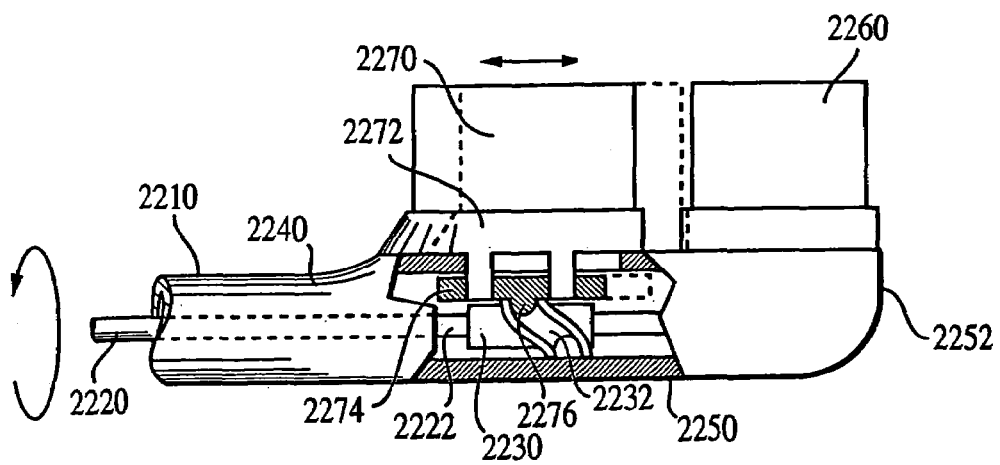
FIG. 16B is a schematic cross-sectional view of the mechanism illustrated in FIG. 16A.
Figure 16C:
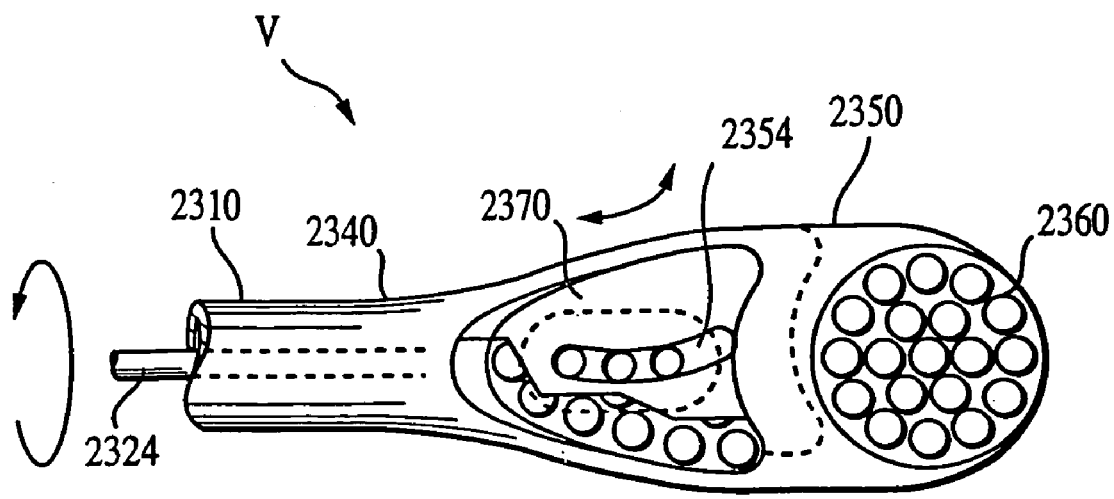
FIG. 16C is a schematic view of a preferred embodiment toothbrush in accordance with the present invention illustrating another mechanism for imparting motion to a bristle carrier.
Figure 16D:
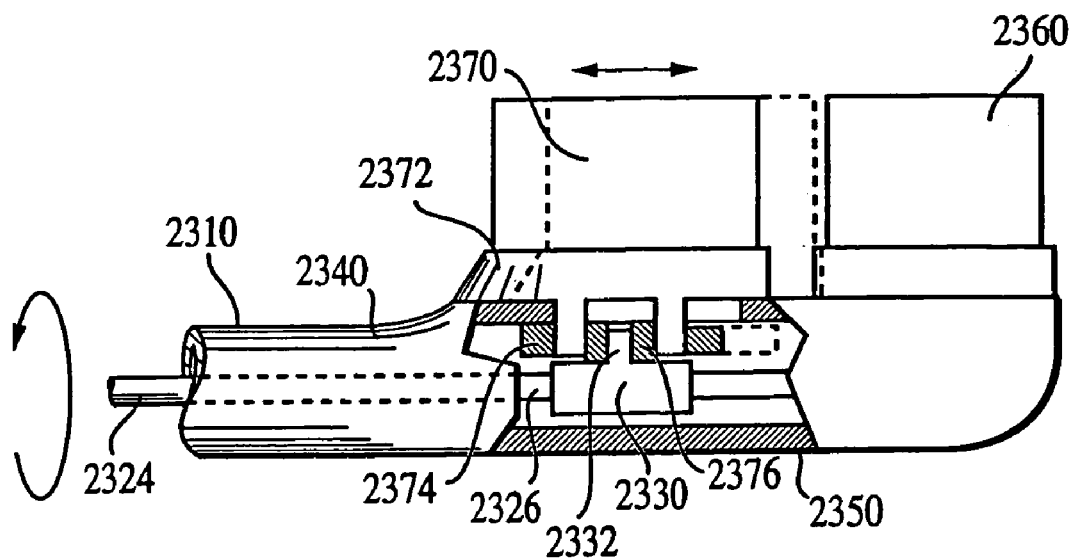
FIG. 16D is a schematic cross-sectional view of the mechanism shown in FIG. 16C.

FIGS. 16A to 16D illustrate mechanisms for achieving the motion illustrated in FIG. 2F. FIGS. 16A and 16B demonstrate a mechanism using a rotating or oscillating powered shaft to achieve the noted motion. And, FIGS. 16C and 16D illustrate a mechanism using a reciprocating shaft to achieve the noted motion. Specifically, FIGS. 16A and 16B illustrate a preferred embodiment toothbrush U having a body 2210, including a neck 2240, and a head 2250. Disposed along the head 2250 is a distal-most or first bristle carrier 2260 and a second bristle carrier 2270. The first bristle carrier 2260 is located near the distal-most end 2252 of the head 2250. The body 2210 encloses a rotating or oscillating shaft 2220 having a distal end 2222. A gear member 2230 is engaged or otherwise secured to the distal end 2222 of the shaft 2220. The gear member 2230 defines a channel 2232 along its outer surface. The second bristle carrier 2270 includes a base 2272 and a plate 2274 having a downwardly extending tracking or guide member 2276. The base is movably disposed on the head and positionable with respect to the head. The tracking member 2276 is disposed or otherwise engaged within the channel 2232 of the gear member 2230. The head 2250 includes a guide channel or elongated aperture 2254 defined along an upwardly directed surface generally underneath the second bristle carrier 2270. Upon operation, the shaft 2220 is rotated or oscillated which in turn causes similar movement of the gear member 2230. As the gear member 2230 undergoes that motion, the tracking member 2276 is linearly displaced within the channel 2232. Linear displacement of the tracking member 2276 causes similar linear displacement of the plate 2274 and base 2272 of the second bristle carrier 2270. The guide channel 2254 defined along the head 2250 imparts a further component to the motion of the second bristle carrier 2270. In the illustration shown in FIG. 16A, since the guide channel 2254 is curvilinear then so, too, is the travel path of the second bristle carrier 2270.

FIGS. 16C and 16D illustrate another preferred embodiment mechanism utilized to achieve the noted motion of FIG. 2F by use of a reciprocating shaft. FIGS. 16C and 16D illustrate a preferred embodiment toothbrush V, having a body 2310, a neck 2340, and a head 2350. Disposed along the head 2350 is a distal-most first bristle carrier 2360 and a second bristle carrier 2370. The second bristle carrier has a base 2372 and a plate 2374 having a downwardly extending guide member 2376. The base is movably disposed on the head and positionable with respect to the head. The guide member 2376 is affixed or otherwise engaged with an engagement member 2332 which extends from a coupler 2330 affixed to the distal end 2326 of the shaft 2324. The head 2350 defines a guide channel or elongated aperture 2354 generally underneath the second bristle carrier 2370. The guide channel imparts a particular desired path of travel for the second bristle carrier 2370. During operation, the shaft 2324 reciprocates, thus causing linear displacement of the coupler 2330. The coupler 2330 imparts this motion to the plate 2374 and base 2372 of the second bristle carrier 2370. This reciprocating motion is further modified by the orientation and shape of the guide channel 2354 defined in the head 2350.

FIGS. 20A to 20D illustrate a mechanism for achieving the motion noted in FIG. 2G. Specifically, these figures illustrate a preferred embodiment toothbrush AC having a body 3010, including a neck 3040, and a head 3050. Defined within the interior of the head 3050 are a plurality of internal guide members 3054. These guide members 3054 define one or more camming apertures 3056. The brush AC further includes a first bristle carrier 3060 and a second bristle carrier 3070. The first bristle carrier 3060 is disposed near a distal-most end 3052 of the head 3050 of the brush AC. The body 3010 generally encloses a reciprocating shaft 3024 having a distal end 3026. The second bristle carrier 3070 includes a base 3072 and a downward extension member 3074. The base is positionable and moveably disposed on the head. Extending laterally outward from the downward extension member 3074 are a plurality of lateral extension members 3076. Disposed at a lower-most region of the downward extension member 3074 is a drive tab 3078. A linkage assembly preferably in the form of a connector 3080 engages the distal end 3026 of the reciprocating shaft 3024 to the downward extension member 3074 of the second bristle carrier 3070. Specifically, the connector 3080 is engaged with the distal end 3026 of the shaft 3024 and provides an engagement aperture 3082. The drive tab 3078 of the downward extension member 3074 extends and is generally engaged and disposed in the engagement aperture 3082 of the connector 3080. During operation, as the reciprocating shaft 3024 reciprocates within the neck 3040 of the body 3010, that reciprocating motion is imparted to the connector 3080. The connector 3080 in turn is engaged to the second bristle carrier 3070 and generally engages that component in a similar manner. The aperture, or rather the orientation of the aperture 3056, further guides and modifies the motion of the second bristle carrier 3070. The lateral extension members 3076 of the downward extension member 3074 are generally received in and by the aperture 3056.

Figure 17A:
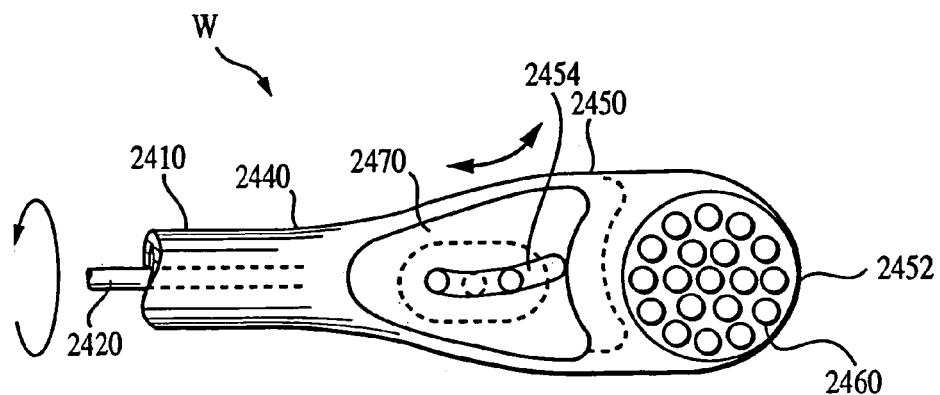
FIG. 17A is a schematic view of a preferred embodiment toothbrush in accordance with the present invention illustrating another mechanism for imparting motion to a bristle carrier.
Figures 17B, 17C:
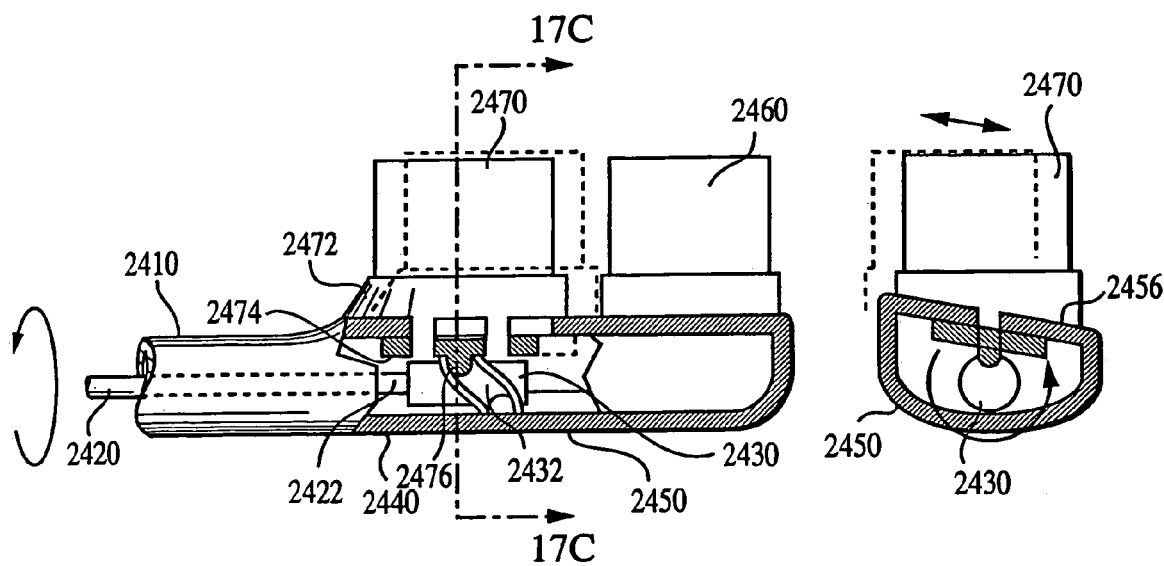
FIG. 17B is a schematic cross-sectional view of the mechanism shown in FIG. 17A.
FIG. 17C is a cross-sectional view taken along line 17C in FIG. 17B.
Figure 17D:
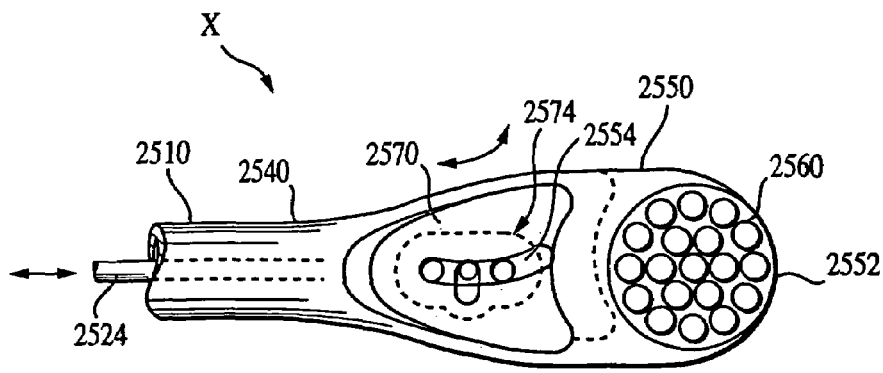
FIG. 17D is a schematic view of a preferred embodiment toothbrush in accordance with the present invention illustrating another mechanism for imparting motion to a bristle carrier.
Figure 17E:
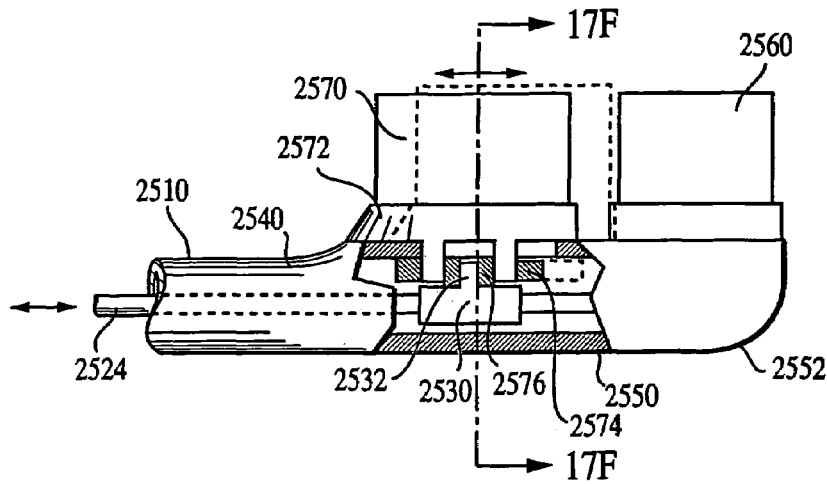
FIG. 17E is a schematic cross-sectional view of the mechanism shown in FIG. 17D.
Figure 17F:
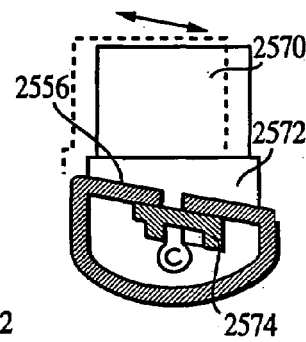
FIG. 17F is a cross-sectional view taken along line 17F in FIG. 17E.

FIGS. 17A to 17G illustrate two mechanisms used to achieve motion noted in FIG. 2H. Specifically, FIGS. 17A to 17C illustrate a mechanism used to achieve the noted motion from a rotating or oscillating shaft. FIGS. 17D to 17G illustrate a mechanism used to achieve the noted motion from a powered reciprocating shaft. Specifically, FIGS. 17A to 17C illustrate a preferred embodiment toothbrush W, having a body 2410, including a neck 2440, and a head 2450. Disposed along the head 2450 is a distal-most or first bristle carrier 2460 and a second bristle carrier 2470. The first bristle carrier 2460 is disposed next to or near the distal-most end 2452 of the head 2450. The body 2410 encloses a rotating shaft 2420. The shaft 2420 has a distal end 2422 to which is engaged a screw member 2430. The screw member 2430 defines a channel 2432. The second bristle carrier 2470 includes a base 2472 and a plate 2474. The base is moveably disposed on the head and positionable with respect to the head. Extending downwardly from the plate 2474 is a guide member 2476. It will be understood that the base may be of a unitary construction and not utilize a separate plate component. That is, the base itself may provide a downwardly extending guide member. The guide member 2476 extends into the channel 2432 defined by the screw member 2430. The head 2450 includes an inclined ramp surface 2456 generally underneath the second bristle carrier 2470 and further defines a guide channel or elongated aperture 2454. During operation, the rotating or oscillating shaft 2420 imparts a similar motion to the screw member 2430. That, in turn, causes linear displacement of the plate 2474 and the base 2472 of the second bristle carrier 2470. A vertical component is imparted to this motion from the inclined ramp surface 2456 defined along the head 2450. A further curvature or other component of motion is imparted by the orientation of the guide channel 2454.

Figure 17G:
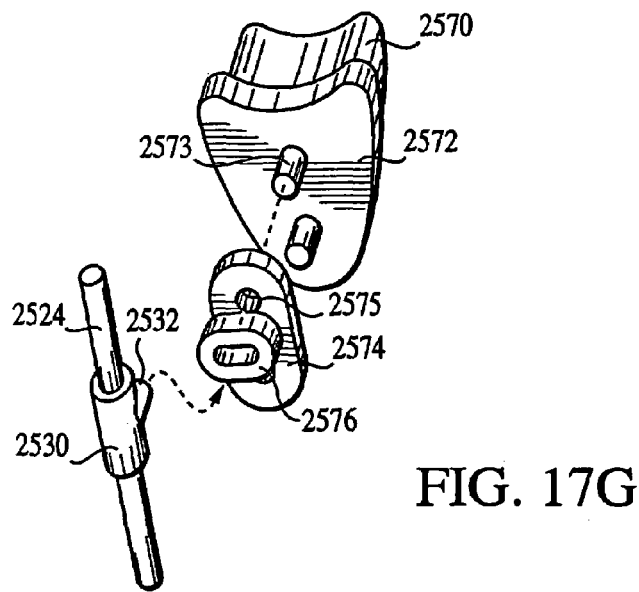
FIG. 17G is an exploded view of the second bristle carrier and certain components of the drive train illustrated in FIGS. 17D to 17F.

FIGS. 17D to 17G illustrate another preferred embodiment mechanism used to achieve the noted motion of FIG. 2H. This drive train utilizes a reciprocating shaft to drive the second bristle carrier. Specifically, FIGS. 17D to 17G illustrate a preferred embodiment toothbrush X, including a body 2510, having a neck 2540, and a head 2550. Disposed along the head 2550 are a distal-most first bristle carrier 2560 and a second bristle carrier 2570. The second bristle carrier includes a base 2572 and a plate 2574 having a downwardly extending guide member 2576. The base is positionable and movably disposed on the head. The base may be unitary and not utilize a separate plate component. That is, the base may provide the downwardly extending guide member. The head 2550 includes an inclined ramp surface 2556 and a guide channel or elongated aperture 2554 defined along its upwardly directed surface generally underneath the second bristle carrier 2570. Engaged or otherwise attached to the shaft 2524, is a coupler 2530. The coupler includes an engagement member 2532 extending therefrom. The engagement member 2532 is received and generally engaged with the guide member 2576 extending from the plate 2574 of the second bristle carrier 2570. As shown in FIG. 17G, it is preferred that the base 2572 is engaged with the plate 2574 by one or more downwardly extending projections 2573 that are received and disposed in apertures 2575 defined in the plate 2574. During operation, the shaft 2524 reciprocates and causes similar reciprocation of the coupler 2530. That, in turn, linearly displaces the plate 2574 and the base 2572 of the second bristle carrier 2570. A vertical component to this motion is imparted by the inclined ramp surface 2556. Further motion or change in path is obtained by use of the guide channel 2554.

Figure 22A:
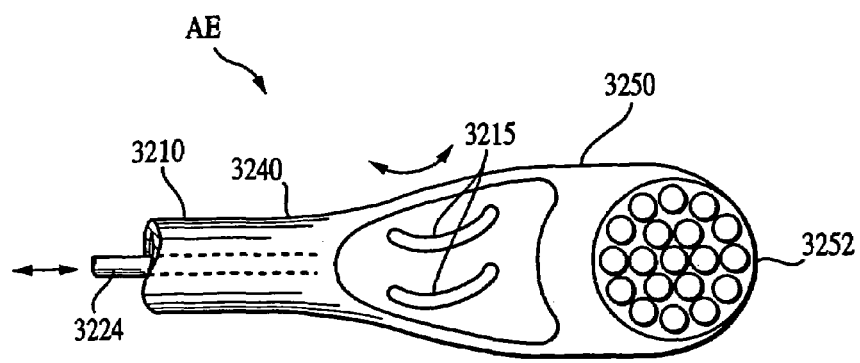
FIG. 22A is a schematic view of a preferred embodiment toothbrush in accordance with the present invention illustrating another mechanism for imparting motion to a bristle carrier.
Figures 22B, 22C:
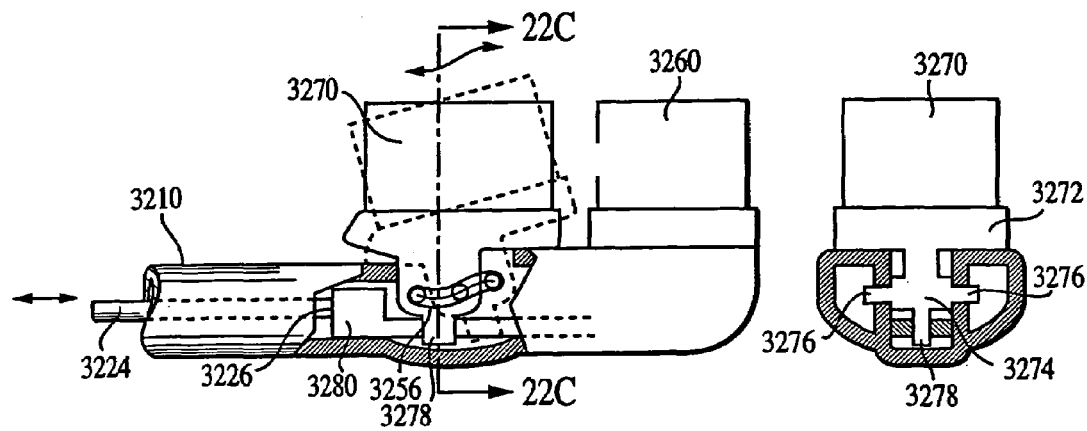
FIG. 22B is a schematic cross-sectional view of the mechanism shown in FIG. 22A.
FIG. 22C is a cross-sectional view taken along line 22C in FIG. 22B.

A mechanism for achieving the motion depicted in FIG. 2I is described later herein. That motion is of the second bristle carrier undergoing repeated motion that is primarily linear, however, non-planar, and hence three dimensional. FIGS. 22A–22C illustrate an exemplary mechanism.

Another category of combinations of movements of the two bristle carriers is that in which the first bristle carrier undergoes two dimensional periodic movement that is primarily linear in combination with two or three dimensional periodic movement that is also primarily linear by the second bristle carrier.

The first bristle carrier may undergo any type of repeated motion that is primarily linear and within the plane of the toothbrush head or within a plane that is generally parallel to the plane of the toothbrush head. Or, the first bristle carrier may undergo repeated motion that is primarily linear and within a plane that is perpendicular to the plane of the toothbrush head (and so, approach a "pulsing" type motion). Or, the first bristle carrier may undergo repeated motion that is primarily linear in a plane other than one that is parallel or perpendicular to the plane of the toothbrush head. Instead, the first bristle carrier may undergo repeated motion that is primarily linear and non-planar. This motion of the first bristle carrier, although non-planar and thus three dimensional, can be characterized by primarily extending within a plane that is (i) within the plane of the toothbrush head or a plane generally parallel thereto; (ii) perpendicular to the plane of the toothbrush head; or (iii) different than either the plane of the toothbrush head or a plane perpendicular thereto.

The second bristle carrier may undergo repeated motion that is primarily linear within the plane of the toothbrush head or a plane that is generally parallel to the plane of the toothbrush head. Or, the second bristle carrier may undergo repeated motion that is primarily linear in a plane that is perpendicular to the plane of the toothbrush head (and so, approach a "pulsing" type motion). Alternately, the second bristle carrier may undergo repeated motion that is primarily linear in a plane other than one that is parallel or perpendicular to the plane of the toothbrush head. Or, the second bristle carrier may undergo repeated motion that is primarily linear and non-planar. This motion of the second bristle carrier, although non-planar and thus three dimensional, can be characterized by primarily extending within a plane that is (i) within the plane of the toothbrush head or a plane parallel thereto; (ii) perpendicular to the plane of the toothbrush head; or (iii) different than either the plane of the toothbrush head or a plane perpendicular thereto.

Again, it will be appreciated that in this category of movement combinations, any of the movements of the first bristle carrier may be utilized in combination with any of the movements of the second bristle carrier.

Figure 3A:
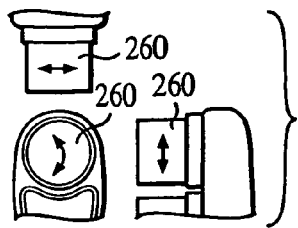
FIG. 3A is a detail of a first bristle carrier of the toothbrush shown in FIG. 3 illustrating the bristle carrier undergoing a certain type of motion.
Figure 3B:
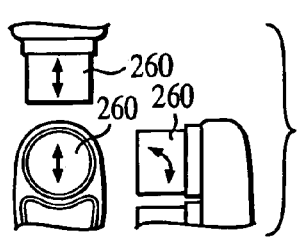
FIG. 3B is a detail of a first bristle carrier of the toothbrush shown in FIG. 3 illustrating the bristle carrier undergoing a certain type of motion.
Figure 3C:
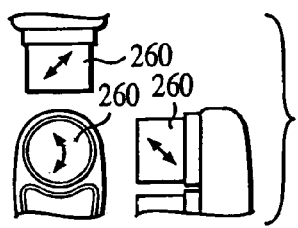
FIG. 3C is a detail of a first bristle carrier of the toothbrush shown in FIG. 3 illustrating the bristle carrier undergoing a certain type of motion.
Figure 3D:
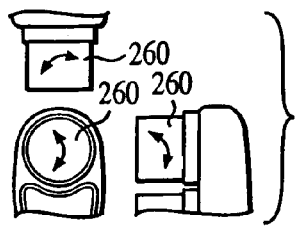
FIG. 3D is a detail of a first bristle carrier of the toothbrush shown in FIG. 3 illustrating the bristle carrier undergoing a certain type of motion.
Figure 3:
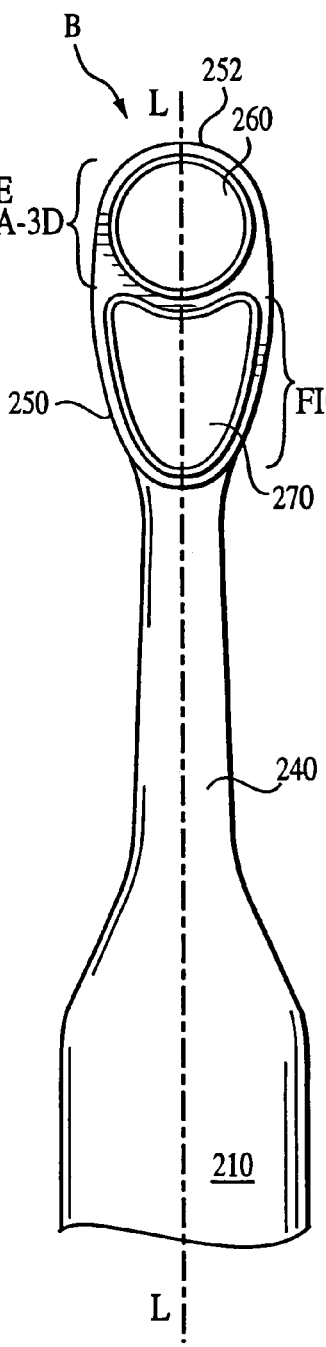
FIG. 3 is a front elevational view illustrating the bristle carriers of a preferred embodiment toothbrush in accordance with the present invention.

FIG. 3 is a front elevational view illustrating another preferred embodiment toothbrush in accordance with the present invention and providing the previously noted combinations of bristle carrier motions. FIG. 3 illustrates toothbrush B having a body 210 with a neck 240 and a head 250. Disposed on the head 250 are a first bristle carrier 260 and a second bristle carrier 270. As will be noted, the first bristle carrier 260 is proximate the distal-most end 252 of the head 250. The first bristle carrier 260 and second bristle carrier 270 of the preferred embodiment toothbrush B are configured to undergo various types of specific motion as follows.

FIGS. 3A to 3D illustrate various types of motion that the first bristle carrier 260 may undergo. FIG. 3A illustrates the first bristle carrier 260 undergoing motion that is primarily linear and within the plane of the toothbrush head or within a plane that is generally parallel to the plane of the toothbrush head. FIG. 3B illustrates the first bristle carrier 260 undergoing repeated motion that is primarily linear and within a plane that is perpendicular to the plane of the toothbrush head, such as plane Y depicted in FIG. 1. And so, FIG. 3B illustrates the pulsing type motion described herein. FIG. 3C illustrates another motion by the first bristle carrier 260 in which its motion is primarily linear and in a plane other than one that is parallel or perpendicular to the plane of the toothbrush head. And, FIG. 3D illustrates another motion of the first bristle carrier 260 in which it undergoes repeated motion that is primarily linear and non-planar, and thus three dimensional.

Figure 3E:
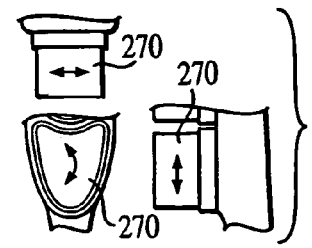
FIG. 3E is a detail of a second bristle carrier of the toothbrush shown in FIG. 3 illustrating the bristle carrier undergoing a certain type of motion.
Figure 3F:
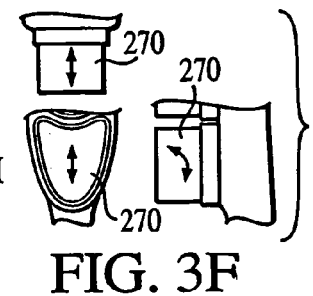
FIG. 3F is a detail of a second bristle carrier of the toothbrush shown in FIG. 3 illustrating the bristle carrier undergoing a certain type of motion.
Figure 3G:
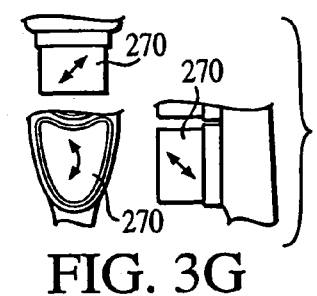
FIG. 3G is a detail of a second bristle carrier of the toothbrush shown in FIG. 3 illustrating the bristle carrier undergoing a certain type of motion.
Figure 3H:
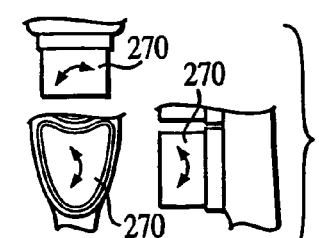
FIG. 3H is a detail of a second bristle carrier of the toothbrush shown in FIG. 3 illustrating the bristle carrier undergoing a certain type of motion.

FIGS. 3E to 3H illustrate additional types of motion that the second bristle carrier 270 of the preferred embodiment toothbrush B may undergo. Specifically, FIG. 3E illustrates repeated motion that the second bristle carrier 270 may undergo that is primarily linear within the plane of the toothbrush head or a plane that is generally parallel to the plane of the toothbrush head. FIG. 3F illustrates the second bristle carrier undergoing repeated motion that is primarily linear in a plane that is perpendicular to the plane of the toothbrush head, such as plane Y shown in FIG. 1, and so approaching a pulsing type motion. FIG. 3G illustrates the second bristle carrier 270 undergoing repeated motion that is primarily linear in a plane other than one that is parallel or perpendicular to the plane of the toothbrush head. FIG. 3H illustrates the second bristle carrier 270 undergoing repeated motion that is primarily linear and non-planar. This motion of the bristle carrier 270 is three dimensional.

The preferred embodiment toothbrush B may be configured such that the first bristle carrier 260 may undergo any of the motions depicted in FIGS. 3A to 3E, in combination with the second bristle carrier 270 undergoing any of the motions depicted in FIGS. 3E to 3H.

Figure 12A:
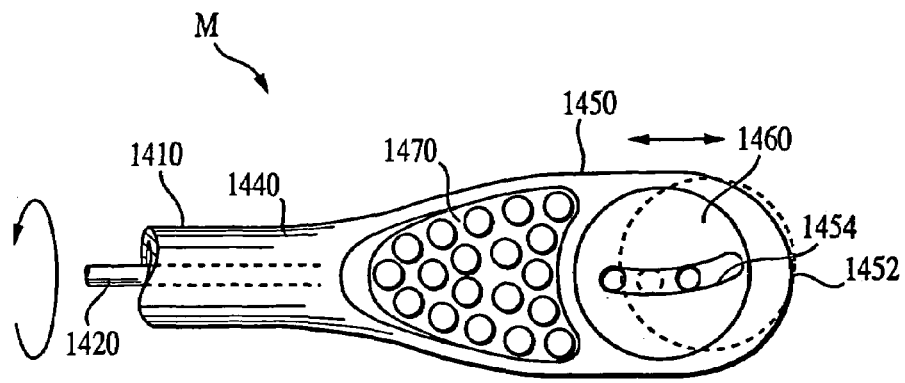
FIG. 12A is a schematic view of a preferred embodiment toothbrush in accordance with the present invention illustrating another mechanism for imparting motion to a bristle carrier.
Figure 12B:
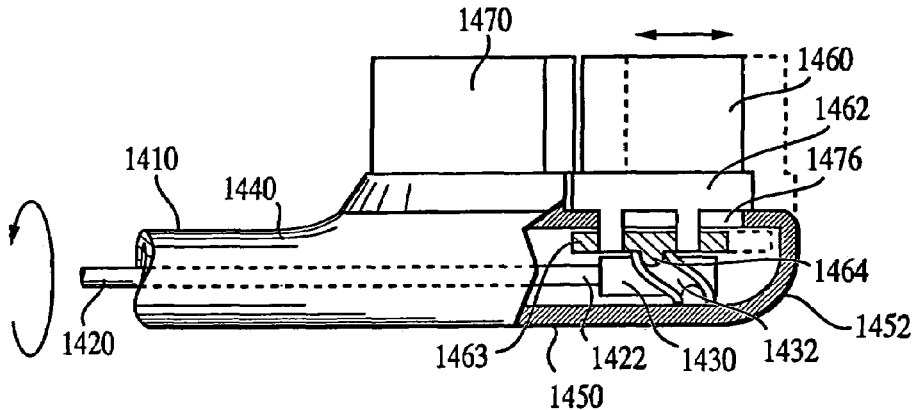
FIG. 12B is a schematic cross-section of the mechanism illustrated in FIG. 12A.
Figure 12C:
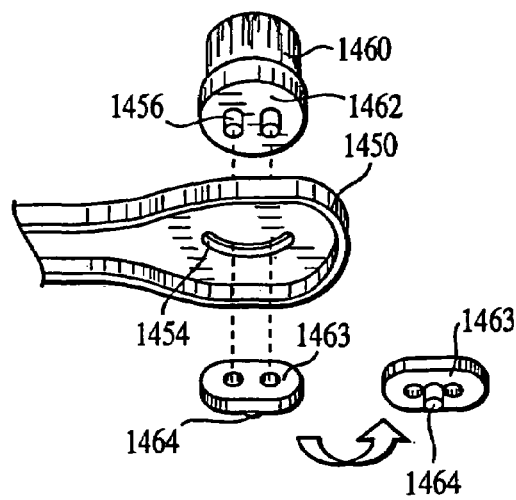
FIG. 12C is a partial exploded view of the first bristle carrier and its engagement with the brush head as shown in FIGS. 12A to 12B.
Figure 12D:
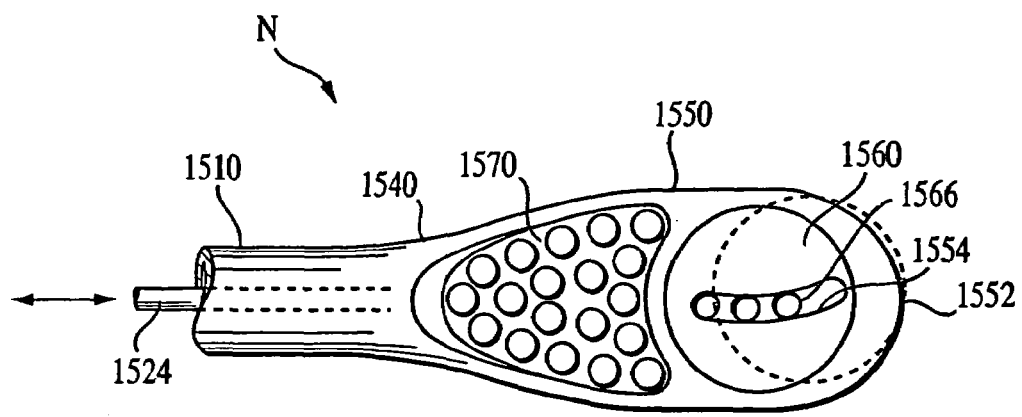
FIG. 12D is a schematic view of a preferred embodiment toothbrush in accordance with the present invention illustrating another mechanism for imparting motion to a bristle carrier.
Figure 12E:
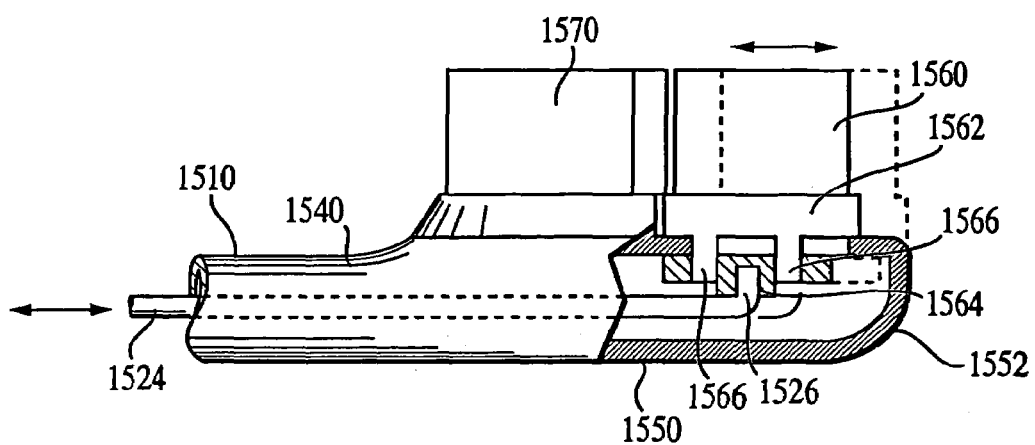
FIG. 12E is a schematic cross-sectional view of the mechanism shown in FIG. 12D.

FIGS. 12A to 12E illustrate two preferred embodiment mechanisms for achieving the motion noted in FIG. 3A. Specifically, FIGS. 12A to 12C illustrate a mechanism for achieving this noted motion by use of a rotating or oscillating powered shaft. And, FIGS. 12D to 12E illustrate a mechanism for achieving this motion using a reciprocating shaft. Specifically, FIGS. 12A to 12C illustrate a preferred embodiment toothbrush M having a body 1410, a neck 1440, and a head 1450. Disposed along the head 1450 is a distal-most first bristle carrier 1460 and a second bristle carrier 1470. The body 1410 encloses or houses a rotating shaft 1420 having a distal end 1422. Engaged along the distal end 1422 is a screw gear 1430. The screw gear 1430 defines a channel 1432. The distal-most bristle carrier includes a base 1462, a carrier plate 1463, and a tracking or guide member 1464 extending from the carrier plate 1463. The screw gear 1430, engaged to the distal end 1422 of the shaft 1420, is positioned such that it is located below or generally underneath the carrier plate 1463 of the first bristle carrier 1460. Specifically, the tracking member 1464 of the carrier plate 1463 is disposed within the channel 1432 defined by the screw gear 1430. It will be appreciated that the base may be a unitary component and include an integral tracking or guide member without a carrier plate 1463. Upon rotation or oscillation of the shaft 1420, the tracking member 1464 is linearly displaced as it moves through the channel 1432 defined along screw gear 1430. The linear displacement of the tracking member 1464 causes linear displacement of the carrier plate 1463 and thus of the base 1462. As the base 1462 is linearly reciprocated along the end or head 1450 of the toothbrush M, the first bristle carrier 1460 is translated. A guide channel or elongated aperture 1454 defined along an upwardly directed surface of the head 1450 further modifies movement of the first bristle carrier 1460. Thus, depending upon the shape or configuration of the guide channel 1454, the first bristle carrier 1460 may be moved in a curvilinear fashion or any other desired path.

FIGS. 12D to 12E illustrate a preferred embodiment mechanism for providing the noted motion shown in FIG. 3A based upon a reciprocating powered shaft 1524. FIGS. 12D to 12E illustrate a preferred embodiment toothbrush N having a body 1510, a neck 1540, and a head 1550. Disposed along the head 1550 is a distal-most first bristle carrier 1560 and a second bristle carrier 1570. The body 1510 encloses a reciprocating shaft 1524 having an offset end 1526. The first bristle carrier 1560 has a base 1562 which provides a downwardly extending retention or guide member 1564. The base is positionable and movably disposed on the head. The retention member 1564 is engaged with one or more secondary guide members 1566 that extend from the base 1562. The guide members 1566 extend through a guide channel or elongated aperture 1554 defined in the upwardly facing surface of the head 1550. It will be appreciated that the base may be of a unitary construction and not utilize a separate retention member 1564. That is, the base itself may include an outwardly extending guide member projecting through the aperture 1554 defined in the head. Upon motion or reciprocation of the shaft 1524, the retention member 1564 which is engaged to the offset end 1526 of the shaft 1524, is linearly displaced within the interior of the head 1550. Linear displacement of the retention member 1564 causes linear displacement of the base 1562 since the one or more guide members 1566 are engaged with the retention member 1564. The shape of the guide channel 1554 defined along the head 1550 further modifies or affects the travel path of the first bristle carrier 1560.

Figure 19A:
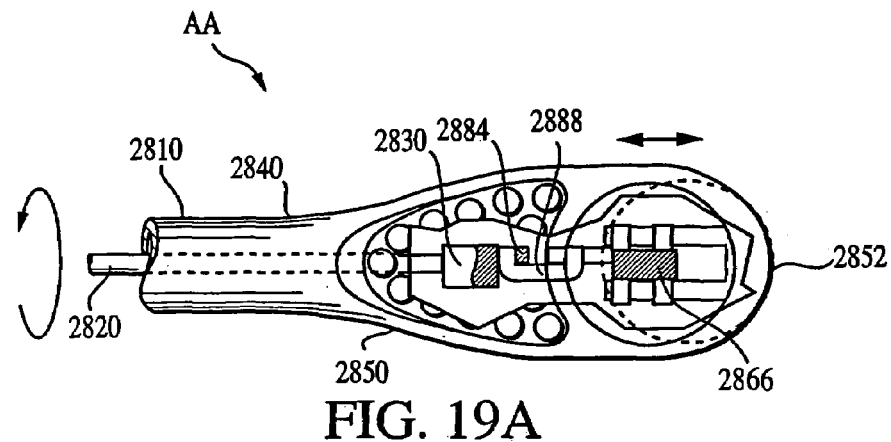
FIG. 19A is a schematic view of a preferred embodiment toothbrush in accordance with the present invention illustrating another mechanism for imparting motion to a bristle carrier.
Figures 19B, 19C:
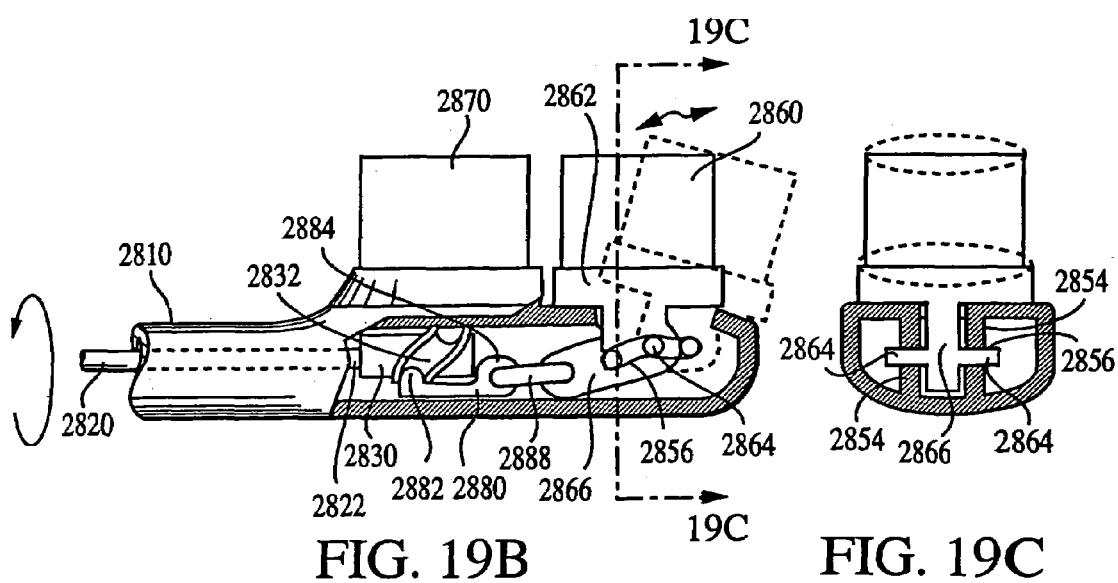
FIG. 19B is a schematic cross-sectional view of the mechanism shown in FIG. 19A.
FIG. 19C is a cross-sectional view taken along line 19C in FIG. 19B.
Figure 19D:
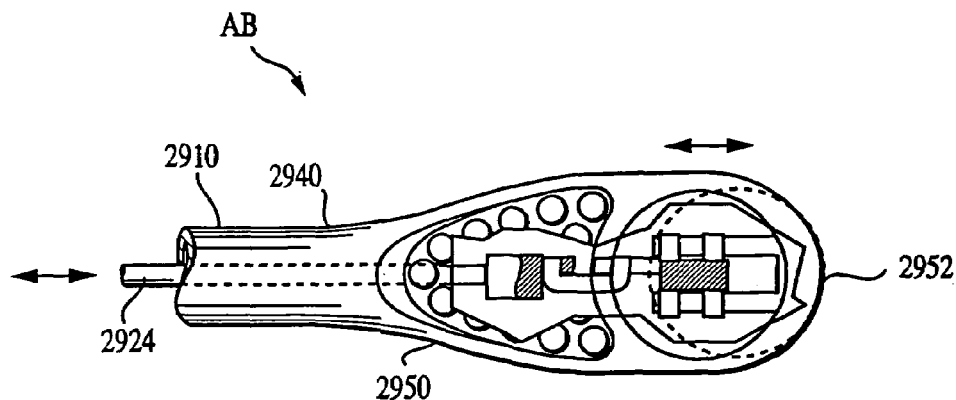
FIG. 19D is a schematic view of a preferred embodiment toothbrush in accordance with the present invention illustrating another mechanism for imparting motion to a bristle carrier.
Figures 19E, 19F:
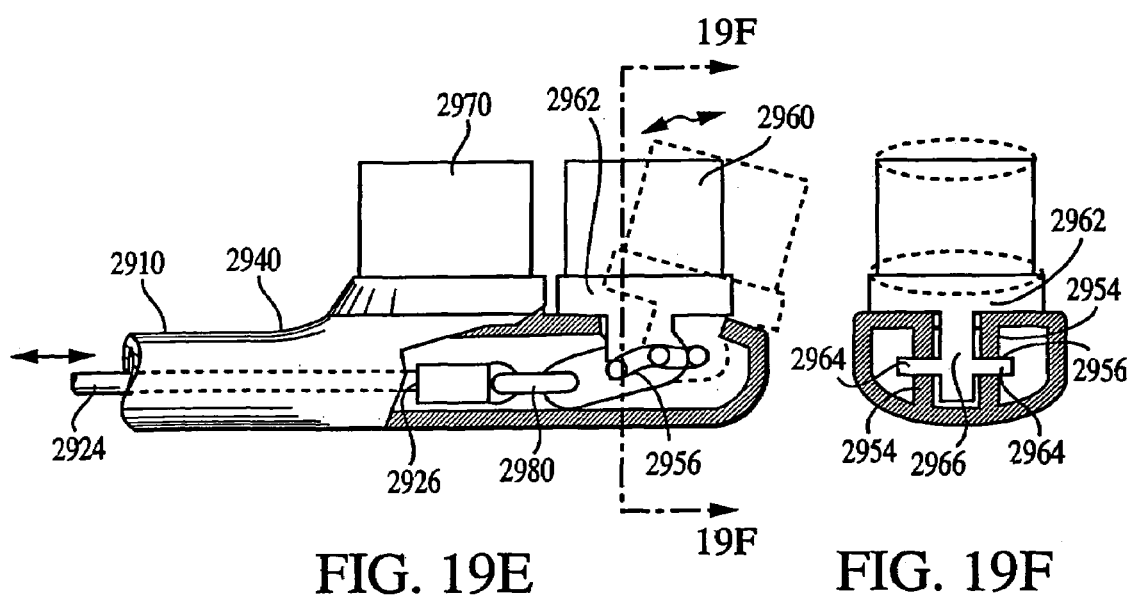
FIG. 19E is a schematic cross-sectional view of the mechanism illustrated in FIG. 19D.
FIG. 19F is a cross-sectional view taken along line 19F in FIG. 19E.
Figure 19G:
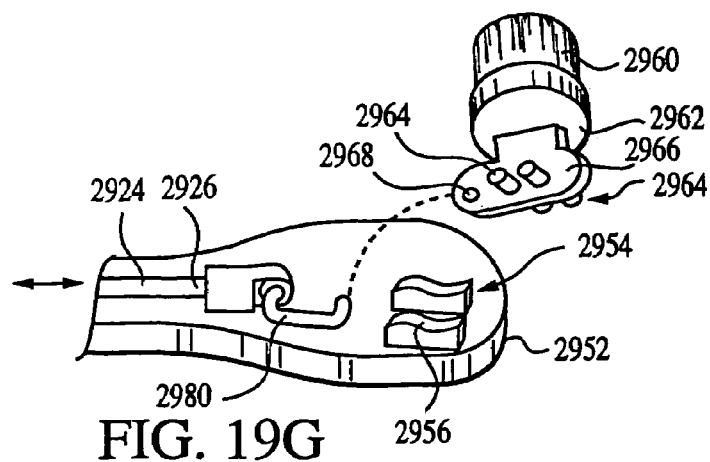
FIG. 19G is a partial exploded view of the mechanism illustrated in FIGS. 19D to 19F.
Figure 20A:
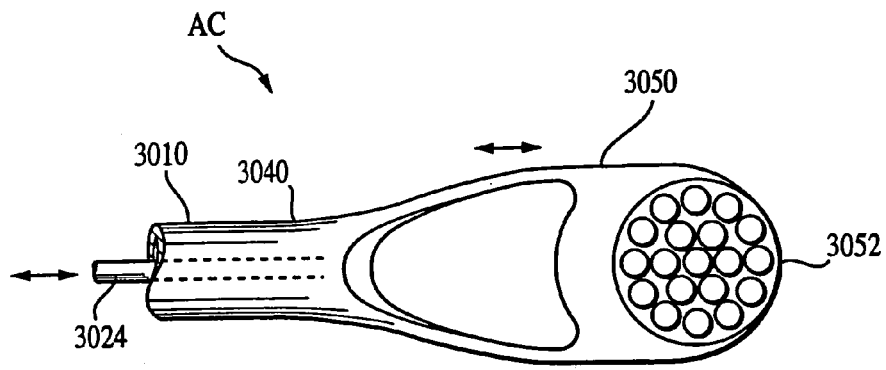
FIG. 20A is a schematic view of a preferred embodiment toothbrush in accordance with the present invention illustrating another mechanism for imparting motion to a bristle carrier.
Figures 20B, 20C:
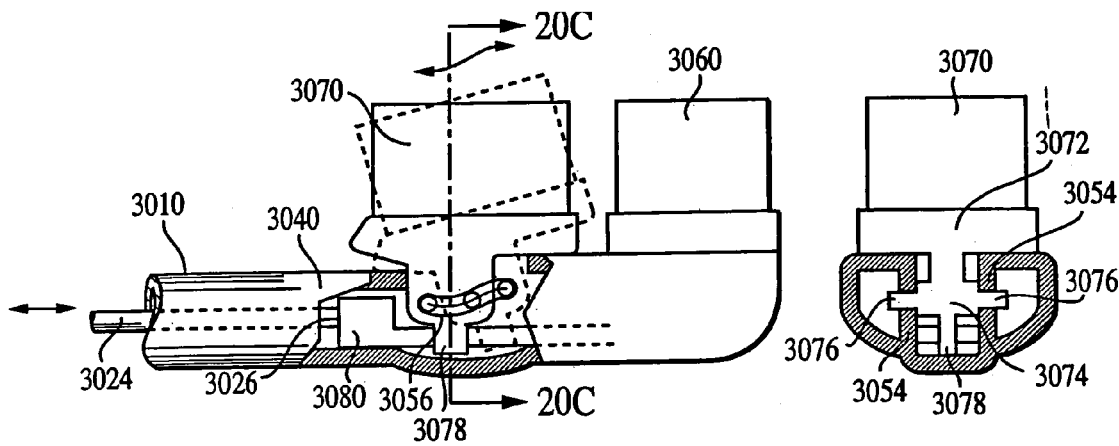
FIG. 20B is a schematic cross-sectional view of the mechanism shown in FIG. 20A.
FIG. 20C is a cross-sectional view taken along line 20C in FIG. 20B.
Figure 20D:
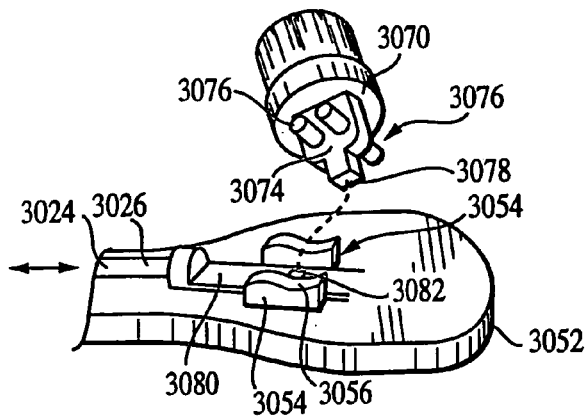
FIG. 20D is a partial exploded view of the mechanism depicted in FIGS. 20A to 20C.

FIGS. 19A to 19G illustrate two preferred embodiment mechanisms for imparting the motion illustrated in FIG. 3B. FIGS. 19A to 19C illustrate a mechanism using a rotating or oscillating powered shaft to achieve the noted motion. And, FIGS. 19D to 19G illustrate a mechanism for achieving such motion using a reciprocating shaft. Specifically, FIGS. 19A to 19C illustrate a preferred embodiment toothbrush AA having a body 2810, a neck 2840, and a head 2850. Disposed along the head 2850 is a first distal-most bristle carrier 2860 and a second bristle carrier 2870. The first bristle carrier 2860 is proximate a distal-most end 2852 of the head 2850. The body 2810 encloses or houses a rotating or oscillating shaft 2820 having a distal end 2822. Engaged at the distal end 2822 is a screw gear 2830 defining a channel 2832. The first bristle carrier 2860 includes a base 2862 and a downwardly extending member 2866. The base is positionable and movably disposed on the head. Extending laterally outward from the downward extension member 2866 are a plurality of lateral extension members 2864. The interior of the head 2850 includes one or more internal guide members 2854 that define an internal guide or camming aperture 2856. The one or more lateral extension members 2864 preferably extend in and are guided by the guide or camming aperture 2856 defined in the guide members 2854. A linkage assembly including a linking member 2880 and a connector 2888 engage the screw gear 2830 to the downward extension member 2866 of the first bristle carrier 2860. Specifically, the linking member 2880 includes a follower 2882 that is received within the channel 2832 of the screw gear 2830. The linking member 2880 also includes an opposite trailing member 2884 located opposite from the follower 2882. A connector 2888 is engaged with the trailing member 2884 of the linking member 2880. And, as seen from the illustrations, the connector 2888 is engaged with the downward extension member 2866 of the first bristle carrier 2860. In operation, as the rotating shaft 2820 rotates or oscillates, so, too, does the screw gear 2830. The channel 2832 imparts a reciprocating motion to the linking member 2880 and connector 2888. This in turn is imparted to the downward extension member 2866 of the first bristle carrier 2860. The guide aperture 2856 defined within the internal region of the head 2850 further governs the movement of the first bristle carrier 2860.

FIGS. 19D to 19G illustrate another preferred embodiment mechanism for achieving the noted motion illustrated in FIG. 3B from a reciprocating shaft. Specifically, these figures illustrate a preferred embodiment toothbrush AB having a body 2910, including a neck 2940, and a head 2950. Disposed along the head 2950 is a distal-most first bristle carrier 2960 and a second bristle carrier 2970. The first bristle carrier 2960 is disposed adjacent and proximate a distal-most end 2952 of the head 2950. The body 2910 encloses a reciprocating shaft 2924 having a distal end 2926. The first bristle carrier 2960 includes a base 2962 having a downwardly extending member 2966. The base is positionable and movably disposed on the head. Extending laterally from the downwardly extending member 2966 are a plurality of lateral extension members 2964. Defined within the head 2950 are a plurality of internal guide members 2954. These internal guide members define a camming aperture 2956 for guiding movement of the first bristle carrier 2960. Specifically, it will be seen that the one or more lateral extension members 2964 extend within and engage the aperture 2956. A linkage assembly preferably in the form of a connector 2980 engages the distal end of the reciprocating shaft 2924 to the downwardly extending member 2966. One end of the connector 2980 is affixed to an engagement aperture 2968 defined in the downwardly extending member 2966. In operation, upon reciprocation of the shaft 2924, the connector 2980 and thus the downwardly extending member 2966 of the first bristle carrier 2960 are reciprocated within the head 2950. This motion is further modified by the configuration of the aperture 2956 defined in the guide members 2954.

Figure 13A:
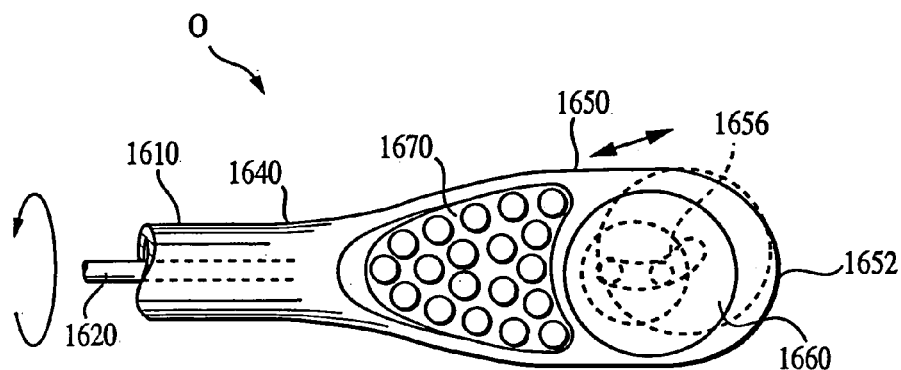
FIG. 13A is a schematic view of a preferred embodiment toothbrush in accordance with the present invention illustrating another mechanism for imparting motion to a bristle carrier.
Figures 13B, 13C:
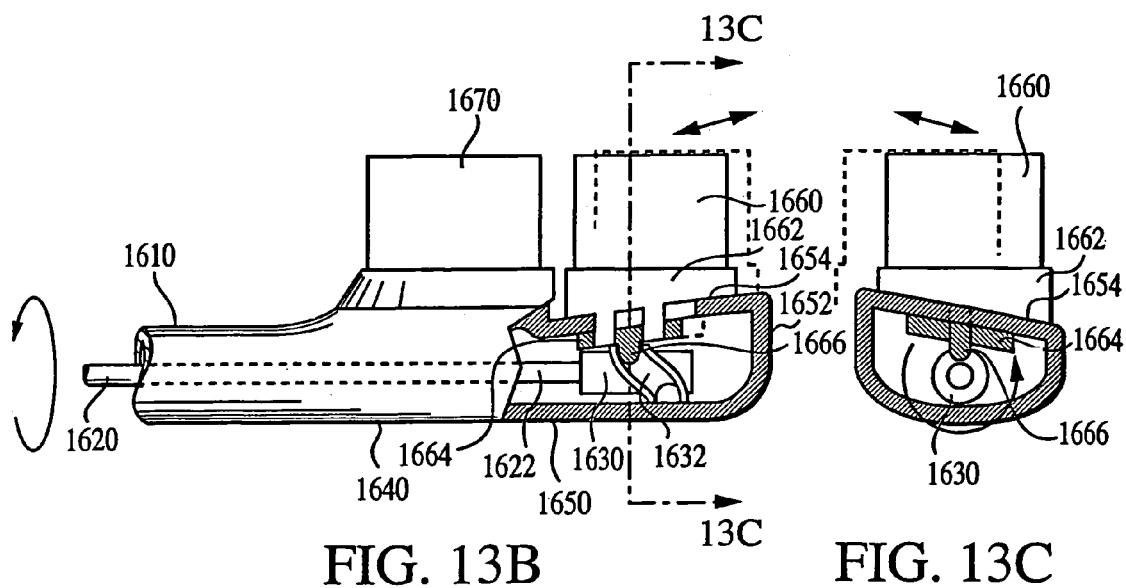
FIG. 13B is a schematic cross-section of the mechanism shown in FIG. 13A.
FIG. 13C is a cross-sectional view taken along line 13C in FIG. 13B.
Figure 13D:
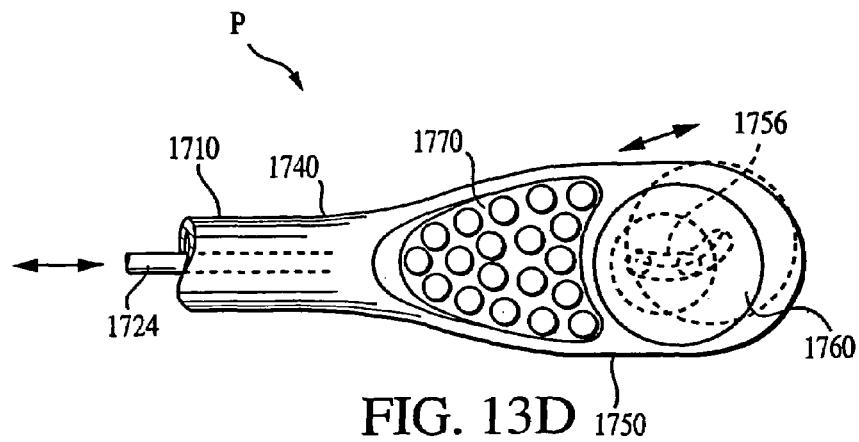
FIG. 13D is a schematic view of a preferred embodiment toothbrush in accordance with the present invention illustrating another mechanism for imparting motion to a bristle carrier.
Figure 13E:
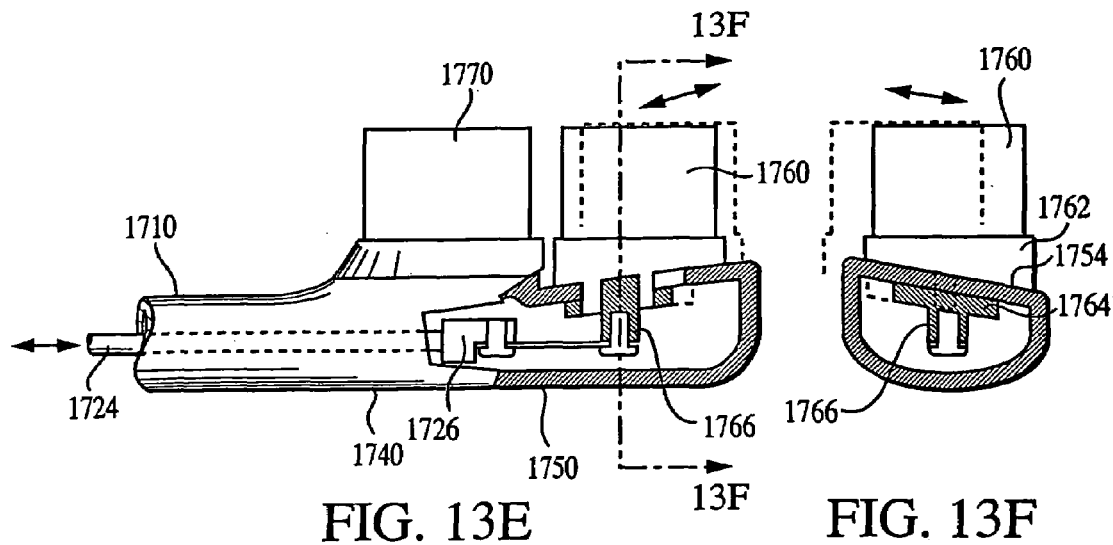
FIG. 13E is a schematic cross-sectional view of the mechanism shown in FIG. 13D.
Figure 13F:
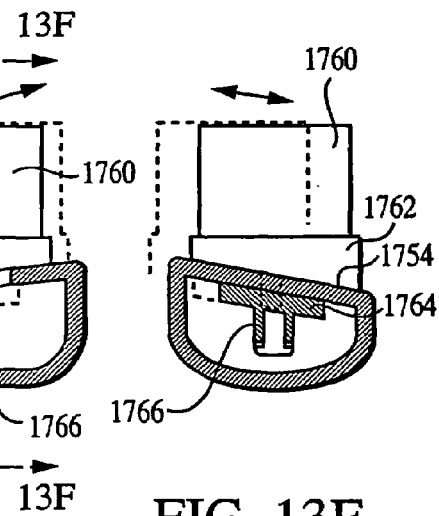
FIG. 13F is a cross-sectional view taken along line 13F in FIG. 13E.

FIGS. 13A to 13F illustrate two preferred embodiment mechanisms for imparting motion as illustrated in FIG. 3C. FIGS. 13A to 13C illustrate a drive train for imparting this motion based upon a rotating or oscillating shaft. FIGS. 13D to 13F illustrate a mechanism for achieving the noted motion from a reciprocating powered shaft. Specifically, FIGS. 13A to 13C illustrate a preferred embodiment toothbrush O having a body 1610, a neck 1640, and a head 1650. Disposed along the head 1650 is a distal-most or first bristle carrier 1660 and a second bristle carrier 1670. The first bristle carrier 1660 is proximate a distal-most end 1652 of the head 1650. The body 1610 encloses a rotating or oscillating shaft 1620 having a distal end 1622. Engaged or otherwise affixed to the distal end 1622 of the shaft 1620 is a gear member 1630. The gear member 1630 provides a channel 1632 which is adapted to receive a tracking or guide member 1666, described in greater detail herein. The first bristle carrier 1660 includes a base 1662 and a plate 1664 engaged to the base 1662. Extending from the bottom of the plate 1664 is a tracking or guide member 1666. As noted, the tracking member 1666 is received within and generally engages the channel 1632 of the gear member 1630. As previously noted with regard to FIGS. 12A–12C, the base may be a unitary component and not utilize a plate member. Also provided along an upwardly facing surface of the head 1650 is a ramp surface 1654. Upon rotation or oscillation of the shaft 1620, the gear member 1630 is similarly rotated or oscillated. This movement causes linear displacement of the tracking member 1666 and thus of the plate 1664. That, in turn, causes linear displacement of the base 1662 of the first bristle carrier 1660. The ramp surface 1654 defined along the upwardly facing surface of the head 1650 imparts a vertical component to the motion of the first bristle carrier 1660. And, providing a guide channel or elongated aperture 1656 may further impart various motion characteristics to the bristle carrier 1660. For example, if the guide channel 1656 is curvilinear or arcuate in shape, that will be the corresponding path of travel for the first bristle carrier 1660.

FIGS. 13D to 13F illustrate a preferred embodiment toothbrush P according to the present invention. The preferred embodiment toothbrush P includes a drive mechanism using a reciprocating powered shaft for imparting motion as noted above in FIG. 3C to the first bristle carrier. The toothbrush P includes a body 1710, having a neck 1740, and a head 1750. Disposed along the head 1750 is a first or distal-most bristle carrier 1760 and a second bristle carrier 1770. The body 1710 encloses a reciprocating shaft 1724 having a distal end 1726. The first bristle carrier 1760 includes a base 1762 and a plate 1764. The plate includes a coupler component 1766 to which is engaged the distal end 1726 of the shaft 1724. It will be understood that the base may be of a unitary construction and thus not utilize a separate plate component. The upwardly facing surface of the head 1750 provides a ramp surface 1754 and further defines a guide channel or elongated aperture 1756 which may be in nearly any desired shape. The base is positionable and movably disposed on the head. The base is positioned over the guide channel 1756. The guide channel 1756 is illustrated in these figures as having a curvilinear shape. Upon motion or reciprocation of the shaft 1724, the coupler 1766 and thus the plate 1764 are linearly displaced within the head 1750 of the toothbrush P. Movement of the plate 1764 in turn causes linear displacement of the base 1762 and thus of the bristle carrier 1760. The ramp surface 1754 provides a vertical component to the motion of the first bristle carrier 1760 and, the shape of the guide channel 1756 further modifies the travel path of the first bristle carrier 1760.

A mechanism for achieving the motion depicted in FIG. 3D is described later herein. That motion is of the first bristle carrier in which it undergoes repeated motion that is primarily linear and non-planar, and thus three dimensional. FIGS. 21A–21C illustrate an exemplary mechanism.

Previously described FIGS. 16A–16D illustrate mechanisms for achieving the motion depicted in FIG. 3E. That motion is of the second bristle carrier and is primarily linear within the plane of the toothbrush head or a plane that is generally parallel thereto.

Previously described FIGS. 20A–20D illustrate mechanisms for achieving the motion depicted in FIG. 3F. That motion is of the second bristle carrier undergoing repeated motion that is primarily linear in a plane that is perpendicular to the plane of the toothbrush head, and so, approaching a pulsing type motion.

Previously described FIGS. 17A–17G illustrate mechanisms for achieving the motion depicted in FIG. 3G. That motion is of the second bristle carrier undergoing repeated motion that is primarily linear in a plane other than one that is parallel or perpendicular to the plane of the toothbrush head.

A mechanism for achieving the motion depicted in FIG. 3H is described later herein. That motion is of the second bristle carrier undergoing repeated motion that is primarily linear and non-planar. This motion is three dimensional. FIGS. 22A–22C illustrate an exemplary mechanism.

Yet another category of combination of movements of the two bristle carriers is that in which the first bristle carrier undergoes three dimensional periodic primarily linear movement in combination with two or three dimensional periodic primarily linear movement by the second bristle carrier.

The first bristle carrier may undergo repeated motion that is primarily linear and non-planar. The motion of the first bristle carrier, although non-planar and thus three dimensional, can be characterized by primarily extending in a plane that is (i) within the plane of the toothbrush head or a plane parallel thereto; (ii) perpendicular to the plane of the toothbrush head; or (iii) different than either the plane of the toothbrush head or a plane perpendicular to the plane of the toothbrush head.

The second bristle carrier may undergo repeated motion that is primarily linear within the plane of the toothbrush head or a plane that is generally parallel thereto. Or, the second bristle carrier may undergo repeated motion that is primarily linear in a plane that is perpendicular to the plane of the toothbrush head (and so, approach a "pulsing" type motion). Or, the second bristle carrier may undergo repeated motion that is primarily linear in a plane other than one that is parallel or perpendicular to the plane of the toothbrush head. Or, the second bristle carrier may undergo repeated motion that is primarily linear and non-planar. This motion of the second bristle carrier, although non-planar and therefore three dimensional, can be characterized by primarily extending within a plane that is (i) within the plane of the toothbrush head or a plane parallel thereto; (ii) perpendicular to the plane of the toothbrush head; or (iii) different than either the plane of the toothbrush head or a plane perpendicular thereto.

Any of the movements of the first bristle carrier may be utilized in combination with any of the movements of the second bristle carrier.

FIG. 4 illustrates another preferred embodiment toothbrush C in accordance with the present invention and providing the previously noted combinations of bristle carrier motions. Toothbrush C comprises a body 310 having a neck 340 and a head 350. Disposed generally on the head 350 are a first bristle carrier 360 and a second bristle carrier 370. It will be noted that the first bristle carrier 360 is proximate a distal-most end 352 of the head 350. The first bristle carrier 360 and the second bristle carrier 370 may undergo a variety of motions and combinations of motions as follows.

FIG. 4A illustrates the first bristle carrier 360 undergoing repeated motion that is primarily linear and non-planar. Restated, the first bristle carrier 360 undergoes a primarily linear and three dimensional motion.

FIGS. 4B to 4E illustrate motions of the second bristle carrier 370. FIG. 4B illustrates the second bristle carrier 370 undergoing repeated motion that is primarily linear and within the plane of the toothbrush head or within a plane that is generally parallel thereto. FIG. 4C illustrates the second bristle carrier 370 undergoing repeated motion that is primarily linear and in a plane that is perpendicular to the plane of the toothbrush head, such as plane Y shown in FIG. 1. FIG. 4C illustrates that motion resembling a pulsing type motion. FIG. 4D illustrates the second bristle carrier 370 undergoing repeated motion that is primarily linear in a plane other than one that is parallel or perpendicular to the plane of the toothbrush head C. FIG. 4E illustrates the second bristle carrier 370 undergoing repeated motion that is primarily linear and non-planar, and thus, motion that is three dimensional.

The preferred embodiment toothbrush C may be configured such that the first bristle carrier 360 may undergo motion such as depicted in FIG. 4A in combination with the second bristle carrier 370 undergoing any of the motions depicted in FIGS. 4B to 4E.

A mechanism for achieving the motion depicted in FIG. 4A is described herein. That motion is of the first bristle carrier undergoing repeated motion that is primarily linear and non-planar. That is, such motion is three dimensional motion. FIGS. 21A–21C illustrate an exemplary mechanism.

Previously described FIGS. 16A–16D illustrate mechanisms for achieving the motion depicted in FIG. 4B. That motion is of the second bristle carrier undergoing repeated motion that is primarily linear and within the plane of the toothbrush head or a plane generally parallel thereto.

Previously described FIGS. 20A–20D illustrate mechanisms for achieving the motion depicted in FIG. 4C. That motion is of the second bristle carrier undergoing repeated motion that is primarily linear and in a plane that is generally perpendicular to the plane of the toothbrush head, and so corresponding to a pulsing type motion.

FIGS. 17A–17G illustrate mechanisms for achieving the motion depicted in FIG. 4D. That motion is of the second bristle carrier undergoing repeated motion that is primarily linear in a plane other than one that is parallel or perpendicular to the plane of the toothbrush head.

A mechanism for achieving the motion depicted in FIG. 4E is described later herein. That motion is of the second bristle carrier undergoing repeated motion that is primarily linear and non-planar, and thus three dimensional. FIGS. 22A–22C illustrate an exemplary mechanism.

Additionally, another category of combinations of movements involves curvilinear movement by the first bristle carrier in combination with movement in two or three dimensions by the second bristle carrier. Specifically, in this category of movements, the first bristle carrier undergoes two dimensional periodic curvilinear movement in combination with two or three dimensional periodic primarily linear movement by the second bristle carrier.

The first bristle carrier may undergo repeated curvilinear motion within the plane of the toothbrush head or a plane parallel to the plane of the toothbrush head. Or, the first bristle carrier may undergo repeated curvilinear motion within a plane perpendicular to the plane of the toothbrush head. Or, the first bristle carrier may undergo repeated curvilinear motion within a plane other than the plane of the toothbrush head or one perpendicular thereto.

The second bristle carrier may undergo repeated motion that is primarily linear within the plane of the toothbrush head or a plane parallel thereto. Or the second bristle carrier may undergo repeated motion that is primarily linear in a plane that is perpendicular to the plane of the toothbrush head (and so, approach a "pulsing" type motion). Or, the second bristle carrier may undergo repeated motion that is primarily linear in a plane other than one that is parallel or perpendicular to the plane of the toothbrush head. Or the second bristle carrier may undergo repeated motion that is primarily linear and non-planar. The motion of the second bristle carrier, although non-planar and therefore three dimensional, can be characterized by primarily extending within a plane that is (i) within the plane of the toothbrush head or a plane parallel thereto; (ii) perpendicular to the plane of the toothbrush head; or (iii) different than either the plane of the toothbrush head or a plane perpendicular thereto.

As previously noted, any and all combinations of movements between the first bristle carrier and second bristle carrier are contemplated.

Figure 5A:
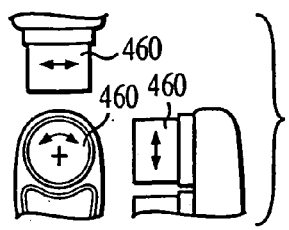
FIG. 5A is a detail of a first bristle carrier of the toothbrush shown in FIG. 5 illustrating the bristle carrier undergoing a certain type of motion.
Figure 5B:
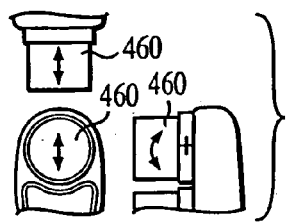
FIG. 5B is a detail of a first bristle carrier of the toothbrush shown in FIG. 5 illustrating the bristle carrier undergoing a certain type of motion.
Figure 5C:
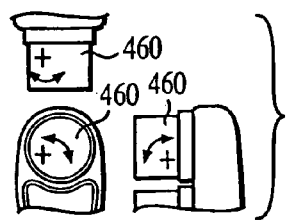
FIG. 5C is a detail of a first bristle carrier of the toothbrush shown in FIG. 5 illustrating the bristle carrier undergoing a certain type of motion.
Figure 5:
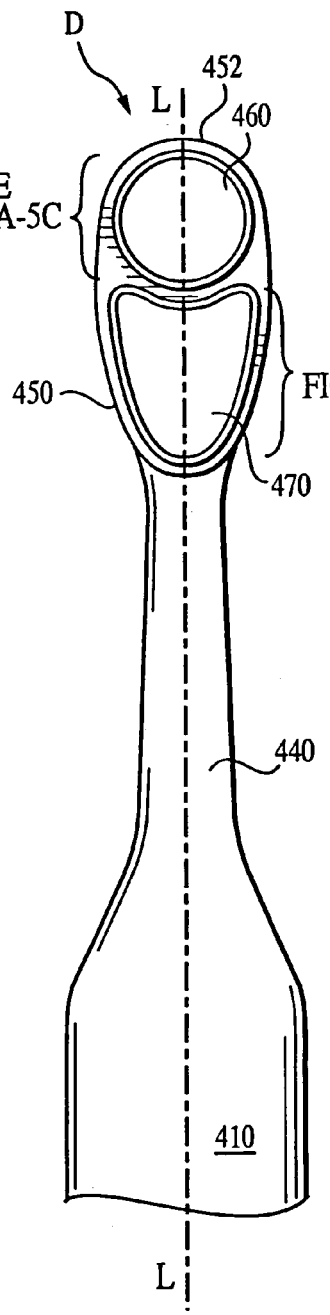
FIG. 5 is a front elevational view of a preferred embodiment toothbrush in accordance with the present invention.

FIG. 5 illustrates another preferred embodiment toothbrush D in accordance with the present invention and providing the previously noted combinations of bristle carrier motions. Toothbrush D comprises a body 410 having a neck 440 and a head 450. Disposed on the head 450 is a first bristle carrier 460 and a second bristle carrier 470. The first bristle carrier 460 is provided proximate to the distal-most end 452 of the toothbrush D. The first bristle carrier 460 and the second bristle carrier 470 of the toothbrush D may undergo a variety of motions as follows.

FIGS. 5A to 5C illustrate specific motions that the first bristle carrier 460 may undergo. Specifically, FIG. 5A illustrates the first bristle carrier 460 undergoing repeated curvilinear motion within the plane of the toothbrush head or a plane parallel to the plane of the toothbrush head. FIG. 5B illustrates the first bristle carrier 460 undergoing repeated curvilinear motion within a plane perpendicular to the plane of the toothbrush head, such as within plane Y illustrated in FIG. 1. FIG. 5C illustrates the first bristle carrier 460 undergoing repeated curvilinear motion within a plane other than the plane of the toothbrush head or one perpendicular thereto.

Figure 5D:
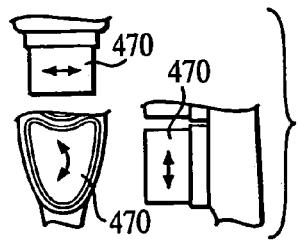
FIG. 5D is a detail of a second bristle carrier of the toothbrush shown in FIG. 5 illustrating the bristle carrier undergoing a certain type of motion.
Figure 5E:
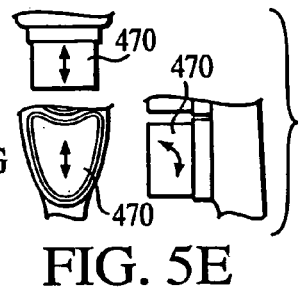
FIG. 5E is a detail of a second bristle carrier of the toothbrush shown in FIG. 5 illustrating the bristle carrier undergoing a certain type of motion.
Figure 5F:
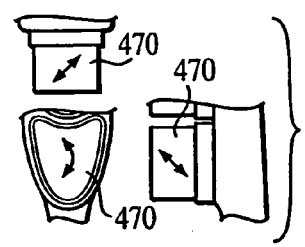
FIG. 5F is a detail of a second bristle carrier of the toothbrush shown in FIG. 5 illustrating the bristle carrier undergoing a certain type of motion.
Figure 5G:
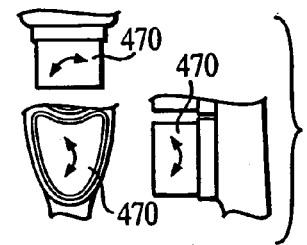
FIG. 5G is a detail of a second bristle carrier of the toothbrush shown in FIG. 5 illustrating the bristle carrier undergoing a certain type of motion.

FIGS. 5D to 5G illustrate various motions that the second bristle carrier 470 may undergo. Specifically, FIG. 5D illustrates the second bristle carrier 470 undergoing repeated motion that is primarily linear within the plane of the toothbrush head or a plane parallel thereto. FIG. 5E illustrates the second bristle carrier 470 undergoing repeated motion that is primarily linear in a plane that is perpendicular to the plane of the toothbrush head, such as within the plane Y illustrated in FIG. 1. FIG. 5E illustrates the motion of the second bristle carrier 470 approaching or resembling a pulsing type motion as described herein. FIG. 5F illustrates the second bristle carrier 470 undergoing repeated motion that is primarily linear in a plane other than one that is parallel or perpendicular to the plane of the toothbrush head. FIG. 5G illustrates the second bristle carrier 470 undergoing three dimensional motion.

The preferred embodiment toothbrush D may be configured such that the first bristle carrier 460 undergoes motion such as shown in any of FIGS. 5A to 5C in combination with the second bristle carrier 470 undergoing motion such as depicted in any of FIGS. 5D to 5G.

Previously described FIGS. 12A–12E illustrate mechanisms for achieving the motion illustrated in FIG. 5A. That motion is of the first bristle carrier undergoing repeated curvilinear motion within the plane of the toothbrush head or a plane parallel thereto.

Figure 10A:
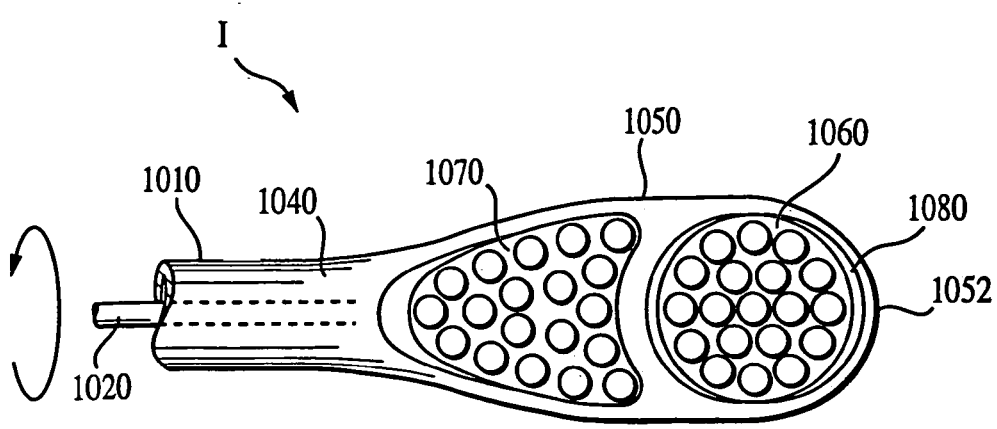
FIG. 10A is a schematic view of a preferred embodiment toothbrush in accordance with the present invention illustrating another mechanism for imparting motion to a bristle carrier.
Figure 10B:
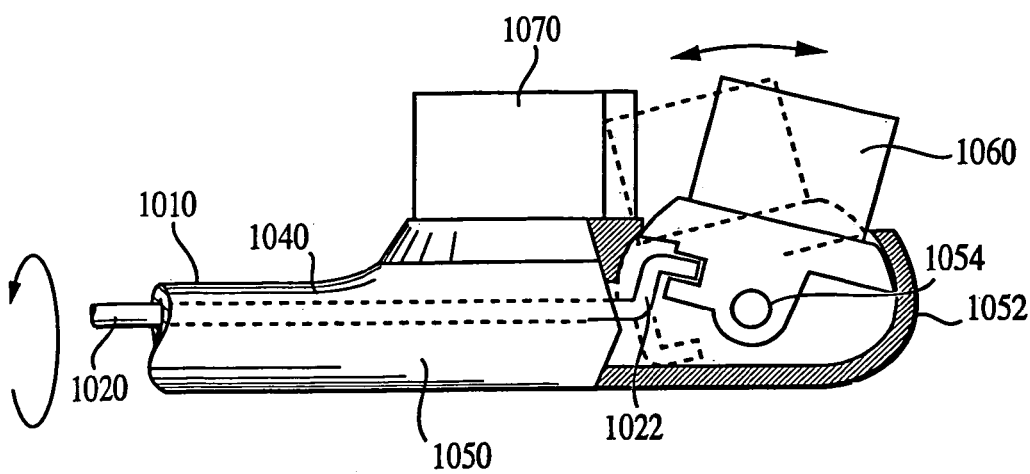
FIG. 10B is a partial cross-section of the preferred embodiment mechanism illustrated in FIG. 10A.
Figure 10C:
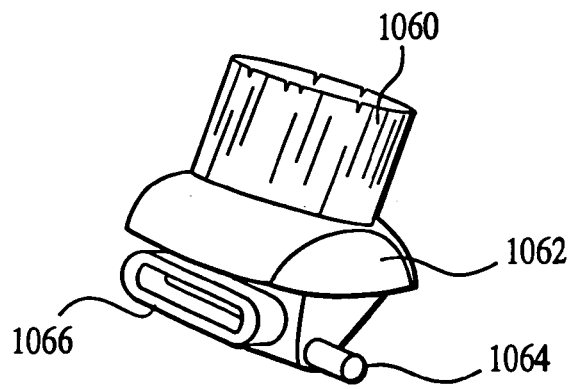
FIG. 10C is a perspective view of a first bristle carrier of the mechanism illustrated in FIGS. 10A and 10B.
Figure 10D:
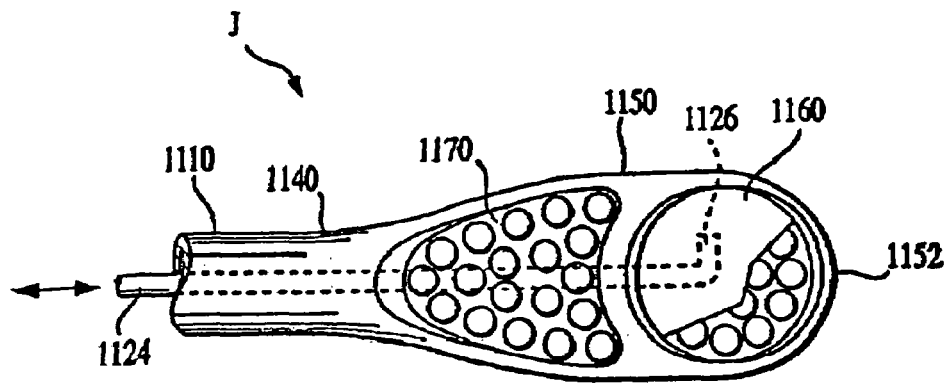
FIG. 10D is a schematic view of a preferred embodiment toothbrush in accordance with the present invention illustrating another mechanism for imparting motion to a bristle carrier.
Figure 10E:
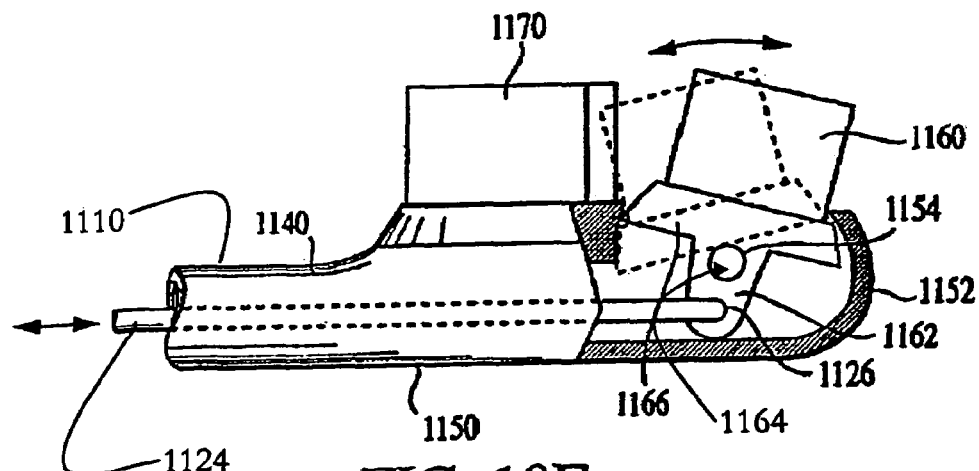
FIG. 10E is a schematic cross-section of the mechanism illustrated in FIG. 10D.

FIGS. 10A to 10E illustrate two preferred embodiment mechanisms utilized to achieve a repeated curvilinear motion for a first bristle carrier within a plane perpendicular to the plane of the toothbrush head as depicted in FIG. 5B. Specifically, FIGS. 10A to 10C illustrate a mechanism for providing such motion from a rotating or oscillating shaft. FIGS. 10D to 10E illustrate a mechanism for providing such motion from a reciprocating shaft. FIGS. 10A to 10C illustrate a preferred embodiment toothbrush I having a body 1010, which includes a neck 1040, and a head 1050. Provided along the head 1050 is a first or distal-most bristle carrier 1060 and a second bristle carrier 1070. As will be understood, the first bristle carrier 1060 is located proximate the distal-most end 1052 of the head 1050. The body 1010 of toothbrush I houses a rotating or oscillating shaft 1020. The shaft 1020 includes an offset end 1022. The first bristle carrier 1060 includes an articulatable base 1062 having two laterally extending pivot members 1064. Preferably, the base is pivotally secured to the head and positionable with respect to the head. The base 1062 also includes a laterally extending receiving channel 1066 that is oriented to receive the offset end 1022 of the shaft 1020. The base 1062 is positioned within the head 1050 such that the pivot members 1064 are each received in an aperture 1054 defined along the sides of the head 1050. And, the offset end 1022 of the shaft 1020 is disposed in and generally engaged with the receiving channel 1066 of the base 1062 of bristle carrier 1060. One or more clearance gaps 1080 are provided around the periphery of the first bristle carrier 1060 to allow movement of the bristle carrier 1060. In operation, upon rotation or oscillation of the shaft 1020, the change in relative position of the offset end 1022 causes displacement of the bristle carrier 1060 about pivot members 1064.

FIGS. 10D to 10E illustrate a preferred embodiment mechanism for providing a repeated curvilinear motion within a plane perpendicular to the plane of the toothbrush head such as shown in FIG. 5B by use of a reciprocating shaft. Specifically, these figures illustrate a preferred embodiment toothbrush J having a body 1110, having a neck 1140, and a head 1150. Provided along the head 1150 is a distal-most or first bristle carrier 1160 and a second bristle carrier 1170. The body 1110 encloses or houses a reciprocating shaft 1124. The shaft 1124 provides an offset end 1126. The first bristle carrier 1160 includes a base 1166 having an arm 1162 that extends downward from the base 1166 into the interior of the head 1150. Preferably, the base is pivotally secured to the head and positionable with respect to the head. Also provided are two laterally extending pivot members 1164 each of which engages an aperture 1154 defined in the head 1150. The first bristle carrier 1160 is generally positioned proximate or near the distal-most end 1152 of the head 1150. During operation and thus reciprocating motion by shaft 1124, the base 1166 of the first bristle carrier 1160 is pivoted about pivot members 1164.

Figure 18A:
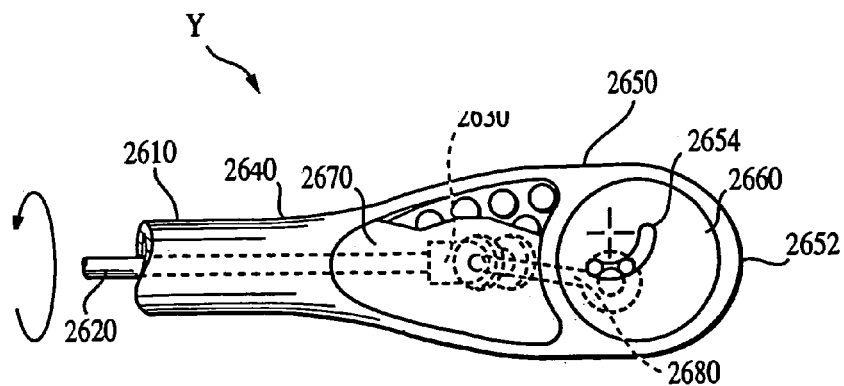
FIG. 18A is a schematic view of a preferred embodiment toothbrush in accordance with the present invention illustrating another mechanism for imparting motion to a bristle carrier.
Figures 18B, 18C:
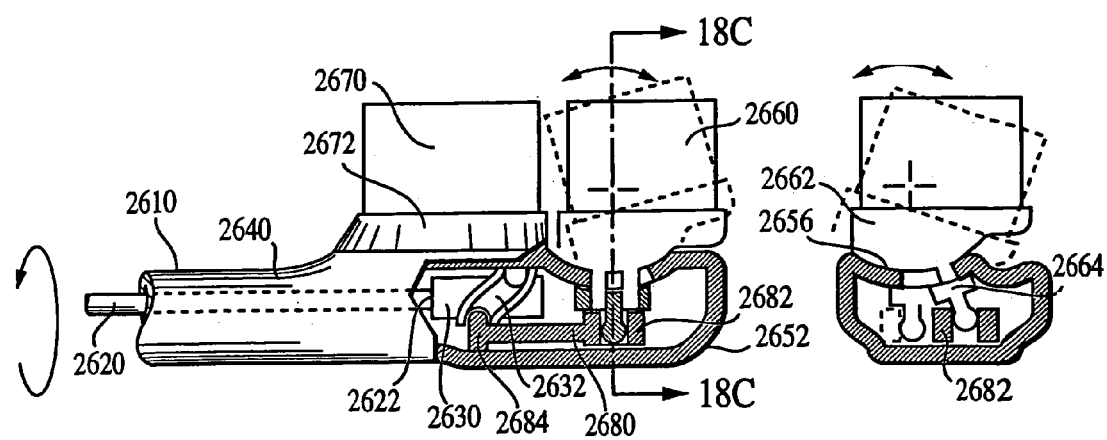
FIG. 18B is a schematic cross-sectional view of the mechanism shown in FIG. 18A.
FIG. 18C is a cross-sectional view taken along line 18C in FIG. 18B.
Figure 18D:
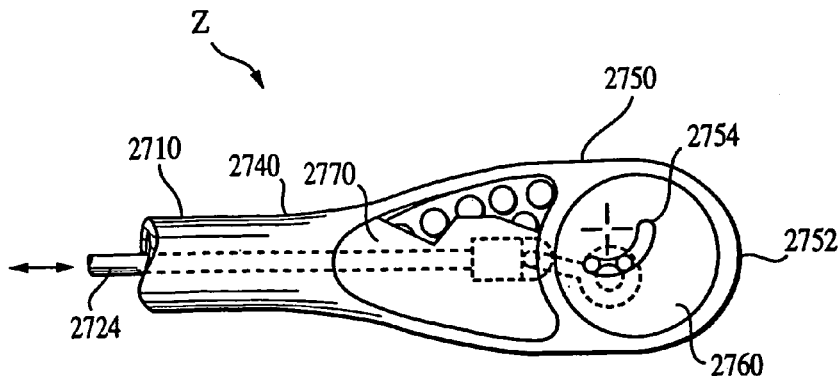
FIG. 18D is a schematic view of a preferred embodiment toothbrush in accordance with the present invention illustrating another mechanism for imparting motion to a bristle carrier.
Figures 18E, 18F:
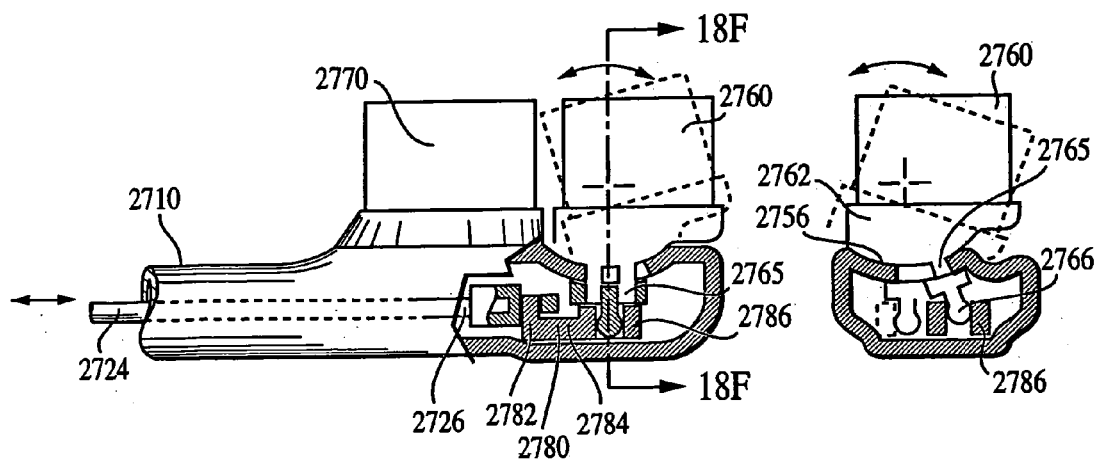
FIG. 18E is a schematic cross-sectional view of the mechanism illustrated in FIG. 18D.
FIG. 18F is a cross-sectional view taken along line 18F in FIG. 18E.
Figure 18G:
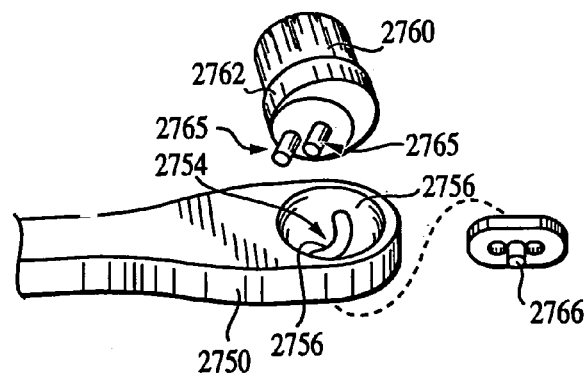
FIG. 18G is an exploded perspective view of the mechanism shown in FIGS. 18D to 18F.

FIGS. 18A to 18G illustrate a preferred mechanism to achieve the motion illustrated in FIG. 5C. Specifically, FIGS. 18A to 18C illustrate a mechanism that achieves such motion from a rotating or oscillating shaft. FIGS. 18D to 18G illustrate a preferred mechanism for achieving such motion using a reciprocating shaft. Specifically, FIGS. 18A to 18C illustrate a preferred embodiment toothbrush Y having a body 2610, having a neck 2640, and a head 2650. Disposed along the distal-most end of the head 2650 is a first distal-most bristle carrier 2660 and a second bristle carrier 2670 disposed alongside. The body 2610 encloses or otherwise houses a rotating or oscillating shaft 2620 having a distal end 2622 to which is attached a screw gear 2630. Defined along an upward facing surface of the head 2650 is a curved and inwardly depressed receiving region or surface 2656. An elongated aperture 2654 is defined within and along the curved receiving surface 2656. The distal-most first bristle carrier 2660 is disposed generally within the curved receiving surface 2656. The first bristle carrier 2660 includes a base 2662 having a downwardly extending guide member 2664 that extends through the aperture 2654. A linkage assembly 2680 connects and provides engagement between the screw gear 2630 and the guide member 2664 of the first bristle carrier 2660. Specifically, the linkage assembly 2680 includes a follower 2684 that is received within a channel 2632 of the screw gear 2630. Disposed at the opposite end of the linkage assembly 2680 is a receiving channel 2682. The receiving channel 2682 receives and engages the guide member 2664 of the base 2662 of the distal-most first bristle carrier 2660. Upon rotation or oscillation of the shaft 2620, the screw gear 2630 rotates or oscillates in a like manner. The orientation of the channel 2632 causes linear displacement of the linkage assembly 2680. The movement of the receiving channel 2682 similarly moves the guide member 2664 of the first bristle carrier 2660. The orientation and shape of the aperture 2654 defined along the head 2650, further imparts the desired motion to the first bristle carrier 2660.

FIGS. 18D to 18G illustrate a preferred embodiment mechanism for imparting this motion, illustrated in FIG. 5C, using a shaft which reciprocates. Specifically, FIGS. 18D to 18G illustrate a preferred embodiment toothbrush Z having a body 2710, with a neck 2740, and a head 2750. Disposed along the head 2750 is a first bristle carrier 2760 and a second bristle carrier 2770. The first bristle carrier 2760 is adjacent or proximate the distal-most end 2752 of the head 2750. The body 2710 encloses or houses a reciprocating shaft 2724 having a distal end 2726. The first bristle carrier 2760 includes a base 2762 with one or more attachment members 2765. The head 2750 includes an inwardly curved receiving region or surface 2756 within which is defined an elongated aperture 2754. The noted attachment members 2765 extend through the aperture 2754 and engage a guide member 2766. The head 2750 also houses a connector 2780 having a first end 2782 and an opposite second end 2784. The first end 2782 is engaged with the distal end 2726 of the shaft 2724. The second end of the connector 2780 includes a receiving channel 2786 which engages the guide member 2766. The base is positionable and movably disposed on the head. The base is positioned over the guide channel. The base may be of a unitary construction and not utilize a separate retention member component. During operation, as the shaft 2724 reciprocates, that motion is imparted to the connector 2780. The reciprocating motion is further imparted to the guide member 2766 due to its engagement with the receiving channel 2786 of the connector 2780. The motion is further modified by the configuration and orientation of the aperture 2754 defined in the receiving surface 2756 of the head 2750. Accordingly, the first bristle carrier 2760 moves in the noted motion.

Previously described FIGS. 16A–16D illustrate mechanisms for achieving the motion illustrated in FIG. 5D. That motion is of the second bristle carrier undergoing repeated motion that is primarily linear within the plane of the toothbrush head or a plane parallel thereto.

Previously described FIGS. 20A–20D depict mechanisms for achieving the motion illustrated in FIG. 5E. That motion is of the second bristle carrier approaching or resembling a pulsing type motion.

Previously described FIGS. 17A–17G show mechanisms for achieving the motion illustrated in FIG. 5F. That motion is of the second bristle carrier undergoing repeated motion that is primarily linear in a plane other than one that is parallel or perpendicular to the plane of the toothbrush head.

A mechanism for achieving the motion depicted in FIG. 5G is described later herein. That motion is of the second bristle carrier undergoing three dimensional motion. FIGS. 22A–22C illustrate an exemplary mechanism.

Another category of combination of movements of the two bristle carriers is that in which the first bristle carrier undergoes three dimensional periodic curvilinear movement in combination with two or three dimensional periodic primarily linear movement by the second bristle carrier.

The first bristle carrier may undergo repeated motion that is curvilinear in nature and non-planar. The motion of the first bristle carrier, although non-planar and thus three dimensional, may be characterized by primarily extending within a plane that is (i) within the plane of the toothbrush head or a plane parallel thereto; (ii) perpendicular to the plane of the toothbrush head; or (iii) different than either the plane of the toothbrush head or a plane perpendicular thereto.

The second bristle carrier may undergo repeated motion that is primarily linear and within the plane of the toothbrush head or within a plane that is generally parallel to the plane of the toothbrush head. The second bristle carrier may undergo repeated motion that is primarily linear in a plane that is perpendicular to the plane of the toothbrush head (and so, the second bristle carrier would approach a "pulsing" type motion). Or, the second bristle carrier may undergo repeated motion that is primarily linear in a plane other than one that is parallel or perpendicular to the plane of the toothbrush head. Alternately, the second bristle carrier may undergo repeated motion that is primarily linear and non-planar (hence, the designation that motion of the second bristle carrier is in three dimensions). This motion of the second bristle carrier, although non-planar, can be characterized by primarily extending within a plane that is (i) within the plane of the toothbrush head or a plane parallel thereto; (ii) perpendicular to the plane of the toothbrush head; or (iii) different than either the plane of the toothbrush head or a plane perpendicular thereto.

Again, any and all combinations of movements between the first bristle carrier and the second bristle carrier are contemplated.

FIG. 6 illustrates a front elevational view of the head portion of a preferred embodiment toothbrush E in accordance with the present invention and providing the previously noted combinations of bristle carrier motions. Toothbrush E comprises a body 510 having a neck 540 and a head 550. Disposed on the head 550 is a first bristle carrier 560 and a second bristle carrier 570. The first bristle carrier 560 is positioned or provided proximate the distal-most end 552 of the head 550. As explained herein, the first bristle carrier 560 and the second bristle carrier 570 may undergo a variety of motions as follows.

FIG. 6A illustrates the first bristle carrier 560 undergoing repeated motion that is curvilinear in nature and non-planar. That is, the motion of the first bristle carrier 560 is three dimensional. FIG. 6B illustrates the second bristle carrier 570 undergoing repeated motion that is primarily linear and within the plane of the toothbrush head or within a plane that is generally parallel to the plane of the toothbrush head. FIG. 6C illustrates the second bristle carrier 570 undergoing repeated motion that is primarily linear in a plane that is perpendicular to the plane of the toothbrush head, such as plane Y shown in FIG. 1. And so, FIG. 6C illustrates the second bristle carrier 570 undergoing motion that resembles a pulsing type motion as described herein. FIG. 6D illustrates the second bristle carrier 570 undergoing repeated motion that is primarily linear in a plane other than one that is parallel or perpendicular to the plane of the toothbrush head. And, FIG. 6E illustrates the second bristle carrier 570 undergoing three dimensional motion.

The preferred embodiment toothbrush E may be configured such that the first bristle carrier 560 undergoes motion such as shown in FIG. 6A in combination with the second bristle carrier 570 undergoing any of the types of motion shown in FIGS. 6B to 6E.

A mechanism for achieving the motion depicted in FIG. 6A is described later herein. That motion is of the first bristle carrier undergoing repeated motion that is curvilinear in nature and non-planar. That is, such motion is three dimensional. FIGS. 21A–21C illustrate an exemplary mechanism.

Previously described FIGS. 16A–16D illustrate mechanisms for achieving the motion depicted in FIG. 6B. That motion is of the second bristle carrier undergoing repeated motion that is primarily linear and within the plane of the toothbrush head or a plane parallel thereto.

Previously described FIGS. 20A–20D illustrate mechanisms for achieving the motion depicted in FIG. 6C. That motion is of the second bristle carrier undergoing repeated motion that is primarily linear in a plane that is perpendicular to the plane of the toothbrush head.

Previously described FIGS. 17A–17G illustrate mechanisms for achieving the motion depicted in FIG. 6D. That motion is of the second bristle carrier undergoing repeated motion that is primarily linear in a plane other than one that is parallel or perpendicular to the plane of the toothbrush head.

A mechanism for achieving the motion shown in FIG. 6E is described later herein. That motion is of the second bristle carrier undergoing three dimensional motion.

Figure 23:
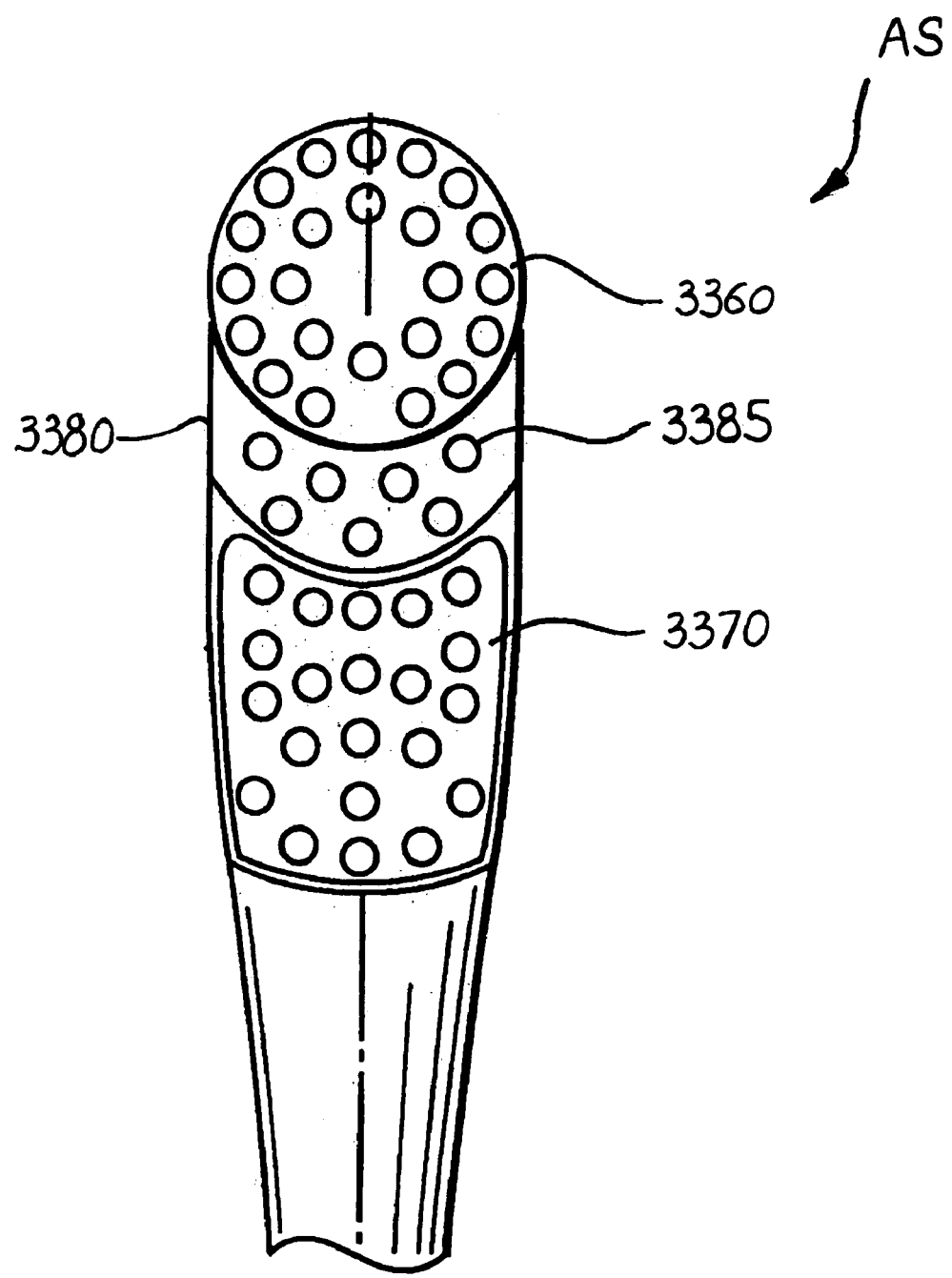
FIG. 23 is a schematic front view showing an embodiment of a bristle carrier having stationary bristles.

Specifically, the preferred structure and arrangement of the moveable and powered bristle carriers is as follows. A second bristle carrier is disposed adjacent the first bristle carrier. While it is desirable to locate the second bristle carrier directly adjacent the first bristle carrier, it is contemplated that a gap may be provided between the first and second bristle carriers. In addition, the gap between the first and second bristle carriers might be filled with stationary bristles which are embedded in a fixed or stationary third bristle carrier which forms part of the toothbrush end. FIG. 23 shows an exemplary embodiment AS comprising a first bristle carrier 3360, a second bristle carrier 3370 and a third, stationary bristle 3380 having stationary bristles 3385 and disposed between the first and second bristle carriers 3360, 3370. Further, while the first bristle carrier has been described as adjacent the distal end of the toothbrush, it is contemplated that the second bristle carrier might be disposed adjacent the distal end of the toothbrush and driven in the same manner as described herein.

While the embodiments of the present invention have been illustrated for simplicity with bristles which extend in a direction substantially perpendicular to the longitudinal axis and the surface of the bristle carriers, it is contemplated that the bristles might be arranged differently to complement or further enhance the motions of the first and/or second bristle carriers. That is, some or all of the bristles might extend in a direction which forms an acute angle to a surface of the bristle carrier and extend in a direction toward or away from the handle. In another embodiment, some of the bristles might extend outwardly away from the head, in another direction, again forming an acute angle with respect to the surface of the bristle carrier. Massaging bristles or bristles of varying height might also be used, such as described in U.S. Pat. Nos. Des. 330,286, Des. 434,563, the substances of which are incorporated herein by reference. Other preferred bristle arrangements suitable for use include those arrangements described in whole or part in U.S. Pat. Nos. 6,006,394; 4,081,876; 5,046,213; 5,335,389; 5,392,483; 5,446,940; 4,894,880; and international publication no. WO 99/23910; the substances of which are incorporated herein by reference.

A variety of drive mechanisms may be utilized in the preferred embodiment toothbrushes described herein. As noted, drive mechanisms that provide a powered rotating output or a reciprocating or oscillating output are preferred. For example, U.S. Pat. Nos. 5,617,603; 5,850,603; 5,974,615; 6,032,313; 5,504,959; 5,524,312; 5,625,916; 5,732,432; 5,070,567; 5,170,525; 5,416,942; 3,588,936; 5,867,856; and 4,397,055, the substances of which are incorporated herein by reference, disclose other motor and rotating or oscillating shaft arrangements that might be suitable. Furthermore, the drive mechanisms disclosed in U.S. Ser. No. 10/027,594, filed Dec. 21, 2001, abandoned; and U.S. Ser. No. 09/993,167, filed Nov. 6, 2001, U.S. Pat. No. 6,725,490, both of which are incorporated herein by reference, may be used. Additionally, any or all of the aspects of U.S. Pat. Nos. 5,617,601 and 5,435,032, both of which are hereby incorporated herein, may be utilized in the toothbrushes described herein.

Figure 7A:
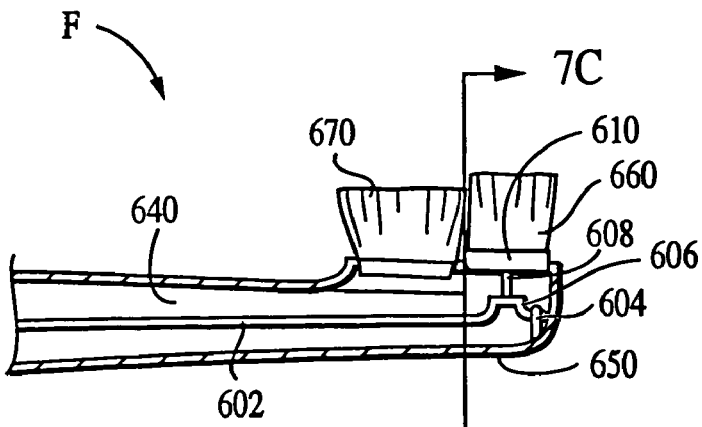
FIG. 7A is a schematic view of a preferred embodiment toothbrush in accordance with the present invention, illustrating a certain mechanism in a first position for imparting motion to a bristle carrier.
Figure 7B:
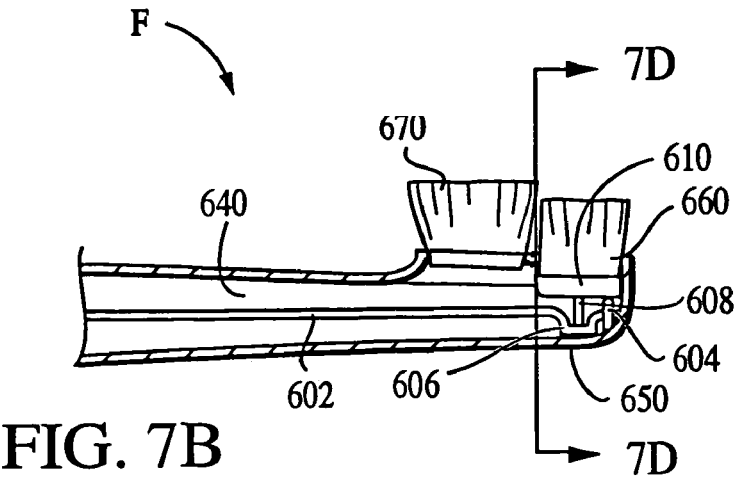
FIG. 7B is a schematic view of the preferred embodiment toothbrush shown in FIG. 7A, illustrating the mechanism in a different position for imparting motion to the bristle carrier.

A preferred mechanism for imparting a pulsing type motion, or referring to FIG. 1, a motion in the Y plane, is illustrated in FIGS. 7A–7D. This mechanism converts a rotary motion, such as from an output of an electric motor, to a reciprocating linear or substantially linear motion in a direction perpendicular to the plane of the toothbrush head. Referring to FIGS. 7A and 7B, a partial view of a preferred embodiment toothbrush F is shown. These figures illustrate a first bristle carrier 660 and a second bristle carrier 670 disposed along a head 650 proximate a neck 640. Extending within the neck 640 is a portion of a drive mechanism including a rotating shaft 602. It will be appreciated that the shaft 602 is powered or driven by an electric motor (not shown) disposed in the body or handle of the toothbrush. The drive mechanism also includes a crank portion 606 that is offset from the longitudinal axis of the shaft 602. The shaft 602 is rotatably supported at the distal end of the toothbrush F by a support 604.

Figure 7C:
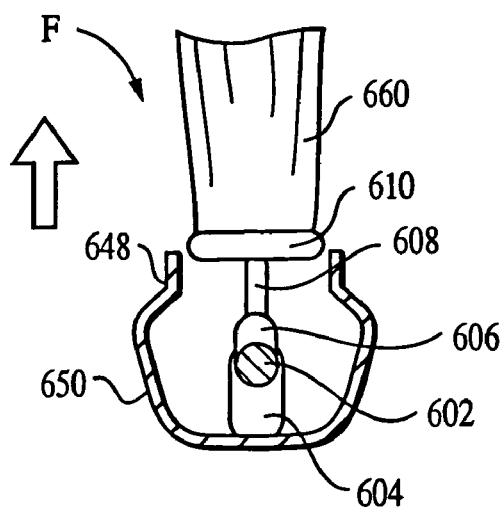
FIG. 7C is a schematic cross-sectional view taken along line 7C—7C in FIG. 7A.
Figure 7D:
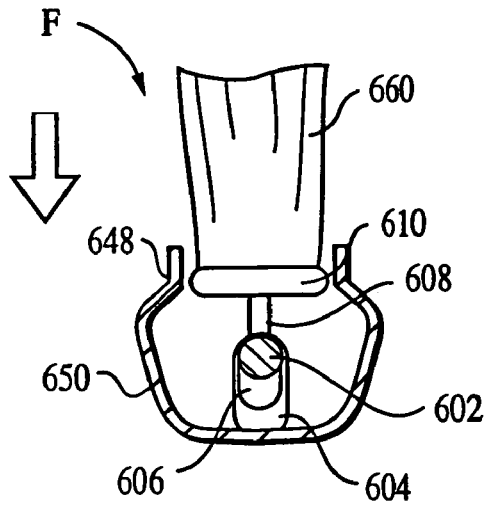
FIG. 7D is a schematic cross-sectional view taken along line 7D—7D in FIG. 7B.

As will be appreciated, either or both of the first or second bristle carriers 660 and 670 may be driven by the mechanism illustrated in FIGS. 7A–7D. However, for purposes of the present discussion, these figures depict only the first bristle carrier 660 being driven. Provided along the base or underside of the bristle carrier 660 is a plate 610. The plate 610 is connected to the crank portion 606 by a linkage member 608. FIG. 7A illustrates the mechanism in one position in which the first bristle carrier 660 is urged outward and generally away from the head 650, and FIG. 7B illustrates another position in which the bristle carrier 660 is drawn towards or partially retracted into the head 650. FIGS. 7C and 7D illustrate cross-sectional views detailing the mechanism and its positions in relation to the bristle carrier 660. FIG. 7C is a cross-sectional view of the head 650 taken along line 7C—7C in FIG. 7A. FIG. 7C illustrates the orientation of the crank portion 606 and base 610 when the first bristle carrier 660 is extended outward from the head 650 of the toothbrush F. FIG. 7D is also a cross-sectional view however, taken along the line 7D—7D in FIG. 7B. FIG. 7D illustrates the orientation of the crank portion 606 and base 610 when the bristle carrier 660 is drawn towards the head 650. It may be desirable to provide a guide member 648 that extends alongside the plate 610 to provide a channel within which the plate 610 and bristle carrier 660 may reciprocate as shaft 602 rotates.

Another preferred mechanism for imparting motion to one or more bristle carriers is described in provisional application Ser. No. 60/361,625, filed Mar. 4, 2002, herein incorporated by reference. That mechanism imparts a "side-to-side" motion to a bristle carrier. Referring to FIG. 1, such motion causes either of both of the bristle carriers 60 and 70 to reciprocate within the plane of the toothbrush head, e.g. within the X plane, or within a plane parallel thereto, and in a direction generally perpendicular to the longitudinal axis of the toothbrush.

Specifically, a representative drive mechanism to achieve a "side-to-side" motion is as follows. Referring to FIGS. 8A and 8B, a preferred embodiment toothbrush G is illustrated. A first bristle carrier 760 is movably mounted in slots 702 in a bristle carrier 750 and driven in a reciprocating or translating, transverse motion within the slots 702 by a cam 755 included on a driving shaft 745. The cam 755 can comprise an appropriately shaped bead placed over or molded and fixedly secured to the shaft 745. For example, the bead is shaped as an eccentric cam. Alternatively, the cam profile may utilize one or more rectilinear, curvilinear or other types of bends. A first cam follower 734 and a second cam follower 736 each extend from a bottom surface of the first bristle carrier 760. The cam followers are, for example, offset from the longitudinal axis L of the first bristle carrier and straddle or capture the cam 755. As the motor (not shown) rotates the shaft 745 in accordance with arrow C, the cam 755 contacts a surface 744 of the first cam follower 734 and drives the first cam follower 734, and therefore, the first bristle carrier 760 away from a first side 751 and toward a second side 753 of the bristle carrier 750 along a transverse axis 782 of the first bristle carrier 760. As the shaft 745 continues to rotate, the cam 755 becomes disengaged with the first cam follower 734. The cam 755 then contacts a surface 746 of the second cam follower 736 and drives the second cam follower 736, and therefore, the first bristle carrier 760 toward the first side 751 and away from the second side 753 of the bristle carrier 750. A clearance 765 is provided between the first and second bristle carriers 760, 770 to accommodate the spacing requirements of this motion. As this back and forth or "side-to-side" motion is repeated (as the shaft 745 continues to rotate), a sweeping motion is provided that provides enhanced cleaning action to the teeth in the direction of arrow B in FIG. 8B.

Figure 9A:
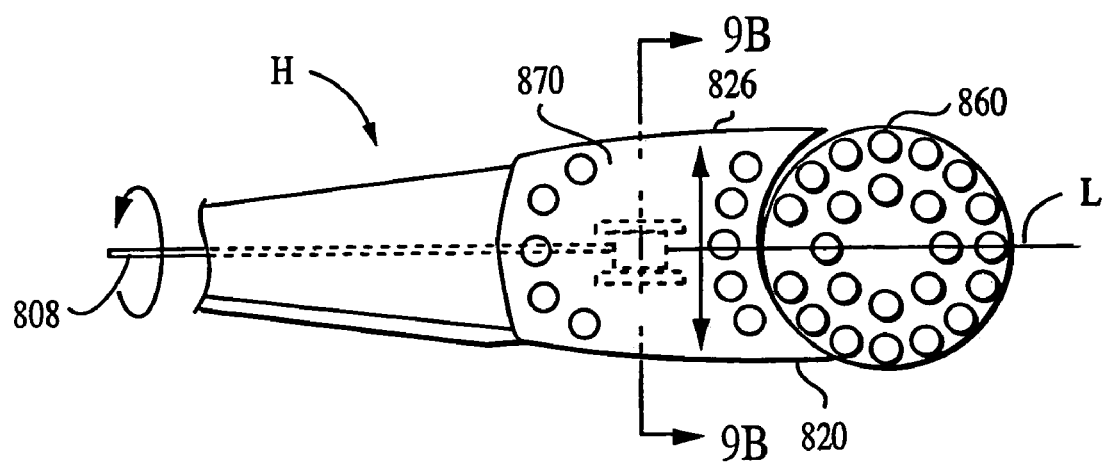
FIG. 9A is a schematic view of a preferred embodiment toothbrush in accordance with the present invention, illustrating another mechanism for imparting motion to a bristle carrier.
Figure 9B:
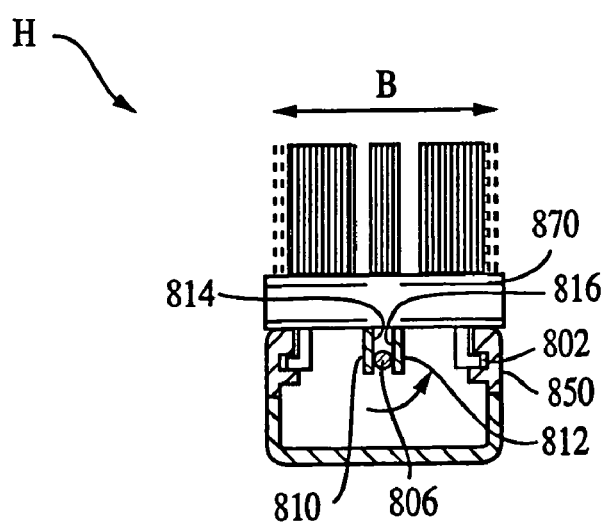
FIG. 9B is a schematic cross-sectional view taken along line 9B—9B in FIG. 9A.

Referring to FIGS. 9A and 9B, in another version of the toothbrush G, referred to herein as toothbrush H, the second bristle carrier 870 is movably mounted in slots 802 in the bristle carrier 850 and separately driven in a reciprocating or translating, transverse motion within the slots 802 by a cam 806 included on a driving shaft 808. The cam 806 can comprise an appropriately shaped bead placed over or molded and fixedly secured to the shaft 808 as in the previously described embodiment for toothbrush G. First 810 and second 812 cam followers depend from a bottom surface of the second bristle carrier 870. The cam followers are, for example, offset from the longitudinal axis L of the second bristle carrier 870 and straddle or capture the cam 806. As the motor (not shown) rotates the shaft 808, the cam 806 comes into contact with a surface 814 of the first cam follower 810 and drives the first cam follower 810, and therefore, the second bristle carrier 870 away from a first side 820 and toward a second side 826 along an axis perpendicular to the longitudinal axis L. As the shaft 808 continues to rotate, the cam 806 becomes disengaged with the first cam follower 810. The cam 806 then comes into contact with a surface 816 of the second cam follower 812 and drives the second cam follower 812, and therefore, the second bristle carrier 870 toward the first side 820 and away from the second side 826 of the bristle carrier portion 850. As this back and forth or side-to-side motion is repeated (as the shaft 808 continues to rotate), the desired sweeping motion in the direction of arrow B is provided.

As previously noted, the first bristle carrier may undergo movement extending in three dimensions. Specifically, this movement is illustrated in FIGS. 3D, 4A, and 6A. And, the second bristle carrier may undergo three dimensional movement, as shown in FIGS. 2I, 3H, 4E, 5G, and 6E. Several of the various mechanisms described herein may be modified to impart such motion to a bristle carrier. For example, a brush head such as shown in FIGS. 20A–20D having internal guide members 3054 that define a camming aperture 3056 could be provided with an upwardly directed elongated aperture defined in the brush head such as aperture 1554 shown in FIG. 12D for example. A bristle carrier undergoing repeated motion along or through these apertures would be non-planar and three dimensional. The exact path desired for the bristle carrier could be obtained by appropriate selection of the shape and orientation of each of the apertures, i.e. the upwardly directed aperture defined along an outer surface of the brush head and a camming aperture defined within the interior of the brush head. It is also contemplated that other components or aspects of mechanisms and tooth brushes described herein could be combined to provide a mechanism or drive train adapted to impart three dimensional motion to a bristle carrier.

FIGS. 21A–21C illustrate a preferred embodiment toothbrush AD comprising a body 3110 having a neck 3140 and a head 3150, which generally houses a reciprocating drive shaft 3124. Disposed on the head 3150 is a first bristle carrier 3160, proximate an end 3152 of the head 3150, and a second bristle carrier 3170. The first bristle carrier 3160 is disposed on a movable base 3162 which includes an extension member 3174 extending within a hollow region defined within the head 3150. The member 3174 includes a plurality of laterally extending guides 3176 that are disposed in a camming aperture 3156 defined within the hollow interior of the head 3150. The extension member 3174 is engaged to a distal end 3126 of the drive shaft 3124 by a linkage assembly 3180. Upon reciprocation of the shaft 3124, the linkage assembly 3180, extension member 3174, base 3162, and first bristle carrier 3160 are displaced. The path of motion of the first bristle carrier 3160 is three dimensional.

FIGS. 22A–22C illustrate a preferred embodiment toothbrush AE comprising a body 3210 having a neck 3240 and a head 3250 with a distal-most end 3252. The body 3210 generally encloses a reciprocating drive shaft 3224. Disposed on the head 3250 is a first bristle carrier 3260 and a second bristle carrier 3270. Specifically, the second bristle carrier 3270 is disposed on a movable base 3272 that includes an arm 3278 that extends into a hollow interior region of the body 3210, neck 3240, or head 3250. The arm 3278 includes one or more laterally extending guide members 3276 that are disposed in and engaged by one or more camming apertures 3256 provided within the hollow interior noted. The arm 3278 of the base 3272 is engaged to a distal end 3226 of the drive shaft 3224 by a linkage assembly 3280 as previously described herein. Preferably, the head 3250 defines one or more elongated apertures 3215 defined along its outer surface. Portions of the base 3272, such as the arm 3278, preferably extend through the apertures 3215. Upon reciprocation of the shaft 3224, the linkage assembly 3280, the arm 3278, the base 3272, and the second bristle carrier 3270 are displaced. Most preferably, the movement of the second bristle carrier 3270 is governed by the shape and orientation of the apertures 3256 and 3215. The resulting motion of the second bristle carrier is three dimensional.

A variety of different mechanisms may be used to provide the noted motions described herein. These mechanisms may utilize either a rotating or oscillating shaft or a linearly reciprocating shaft as a power source. Generally, the various repeating periodic motions are achieved by arrangements of pivoting members and linkage assemblies that have certain predetermined regions of freedom. Accordingly, rotating or reciprocating motion from a powered shaft may be translated to a linear, primarily linear, curvilinear, or a three dimensional motion by particular selection and configuration of components forming the drive mechanism. Furthermore, guide channels may be provided along or within the head or region of the toothbrush body near the bristle carrier(s) for assisting or guiding the movement of the bristle carrier(s).

Additionally, it will be appreciated that any of the mechanisms or drive trains described or illustrated herein may be combined with any of the other mechanisms or drive trains noted herein. And, portions of any of these mechanisms may be combined with portions of any other mechanism noted herein. It is also contemplated that a toothbrush as described herein may employ two of the drive trains noted herein, such that each drive train powers a particular bristle carrier. Accordingly, two electrical motors could also be utilized, one for each drive train.

The present invention has been described with reference to particular embodiments. Modifications and alternations will occur to others upon reading and understanding this specification. For example, while certain cams have been described as comprising bends in a shaft and other cams have been described as including appropriately shaped beads secured to a shaft, the cams are not limited to the suggested form. Indeed, bends may be substituted for beads and beads may be substituted for bends and other shapes, sizes, and configurations can be implemented. Furthermore, it is contemplated that any of the features or aspects of any of the toothbrushes A–AE may be combined with or utilized in conjunction with any of the other features or aspects of any of the toothbrushes A–AE It is intended that all such modifications and alternations are included insofar as they come within the scope of the appended claims or equivalents thereof.

We claim:

1. An electric toothbrush, comprising:
   a handle at a first end of the toothbrush having a motor disposed therein;
   a head at a second end of the toothbrush, the head having a longitudinal axis, the head having a first bristle holder and a second bristle holder; and
   wherein the motor is operatively connected to the second bristle holder to move the second bristle holder in a curvilinear motion along camming apertures, and wherein the motor is operatively connected to the first bristle holder to move the first bristle holder in a non-planar motion.

2. The electric toothbrush of claim 1, wherein the second bristle holder also moves in a non-planar motion.

3. The electric toothbrush of claim 2, wherein the second bristle holder is disposed on a movable base which comprises an extension member extending within a hollow region of the head, wherein the member includes a plurality of laterally extending guides that are disposed in the camming apertures.

4. The electric toothbrush of claim 1, wherein the toothbrush further comprises a reciprocating shaft operatively connected to the motor.

5. The electric toothbrush of claim 1, wherein the first bristle holder is disposed on a movable base which comprises an extension member extending within a hollow region of the head, wherein the member includes a plurality of laterally extending guides that are disposed in the camming apertures.

6. The electric toothbrush of claim 1, wherein a third bristle carrier is disposed between said first and second bristle carriers, and said third bristle carrier is stationary.

* * * * *